(12) United States Patent
Hanna et al.

(10) Patent No.: US 7,029,870 B1
(45) Date of Patent: Apr. 18, 2006

(54) GABAA RECEPTOR EPSILON SUBUNITS

(75) Inventors: Michael C. Hanna, Arlington, VA (US); Ewen F. Kirkness, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/030,832

(22) Filed: Feb. 26, 1998

Related U.S. Application Data

(63) Continuation-in-part of application No. 08/888,012, filed on Jul. 3, 1997, now abandoned.

(51) Int. Cl.
*C12P 21/06* (2006.01)
*C12N 1/20* (2006.01)
*C12N 15/00* (2006.01)
*C12N 15/74* (2006.01)
*C07H 21/04* (2006.01)

(52) U.S. Cl. ............... 435/69.1; 435/252.3; 435/320.1; 435/325; 435/471; 536/23.5

(58) Field of Classification Search ............... 435/69.1, 435/70.1, 71.1, 71.2, 471, 325, 252.3, 320.1; 530/350; 536/23.5
See application file for complete search history.

(56) References Cited

FOREIGN PATENT DOCUMENTS

| WO | WO 94/13799 | 6/1884 |
|---|---|---|
| WO | WO 96/06862 | 3/1996 |
| WO | WO 98/23742 | 6/1998 |

OTHER PUBLICATIONS

Davies et al. Insensitivity to anaesthetic agents conferred by a class of GABA-a receptor subunit. Nature. vol. 385, pp. 820-823, 1997.*
Garret et al. An nRNA encoding a putative GABA-gated chloride channel is expressed in the human cardiac conduction system. J. Neurochem. vol. 68, pp. 1382-1389, 1997.*
Reichmann et al. Activation of an inducible c-fosER fusion protein causes loss of epithelial polarity and triggest epithelial-fibroblastoid cell conversion. Cell. vol. 71, pp. 1103-1116, 1992.*
Adams, M.D. et al., "Initial assessment of human gene diversity and expression patterns based upon 83 million nucleotides of cDNA sequence," *Nature 377(Supp.)*:3-174 (1995).
Adodra, S. and Hales, T.G., "Potentiation, activation and blockade of GABA$_A$ receptors of clonal murine hypothalamic GT1-7 neurones by propofol," *Br. J. Pharmacol. 115(6)*:953-960 (1995).
Amann, E. et al., "Tightly regulated tac promoter vectors useful for the expression of unfused and fused proteins in *Escherichia coli*," *Gene 69(2)*:301-315 (1988).

Bateson, A.N. et al., "γ-Aminobutyric Acid$_A$ Receptor Heterogeneity Is Increased by Alternative Splicing of a Novel β-Subunit Gene Transcript," *J. Neurochem. 56(4)*: 1437-1440 (1991).
Bell, K. et al., "GABAergic Projection From the Ventral, Pallidum and Globus Pallidus to the Subthalamic Nucleus," *Synapse 20(1)*:10-18 (1995).
Bergman, H. et al., "Reversal of Experimental Parkinsonism by Lesions of the Subthalamic Nucleus," *Science 249*:1436-1438 (1990).
Bormann, J. et al., "Mechanism of Anion Permeation through Channels Gated by Glycine and γ-Aminobutyric Acid in Mouse Cultured Spinal Neurones," *J. Physiol. (London) 385*:243-286 (1987).
Buckle, V.J. et al., "Chromosomal Localization of GABA$_A$ Receptor Subunit Genes: Relationship to Human Genetic Disease," *Neuron 3*:647-654 (1989).
Buller, A.L. et al., "Site-Directed Mutagenesis of N-Linked Glycosylation Sites on the γ-Aminobutyric Acid Type A Receptor α1 Subunit," *Mol. Pharmacol. 46(5)*:858-865 (1994).
Davies, P.A. et al., "Insensitivity to anaesthetic agents conferred by a class of GABA$_A$ receptor subunit," *Nature 385*:820-823 (Feb. 1997).
Davies, P.A. et al., "Modulation by general anaesthetics of rat GABA$_A$ receptors comprised of α1β3 and β3 subunits expressed in human embryonic kidney 293 cells," *Br. J. Pharmacol. 120(5)*:899-909 (Mar. 1997).
Gage, P.W. and Chung, S.-H, "Influence of membrane potential on conductance sublevels of chloride channels activated by GABA," *Proc. R. Soc. Lond. B 255(1343)*:167-172 (1994).
Garret, M. et al., "An mRNA Encoding a Putative GABA-Gated Chloride Channel Is Expressed in the Human Cardiac Conduction System," *J. Neurochem. 68*:1382-1389 (Apr. 1997).

(Continued)

*Primary Examiner*—Robert E. Landsman
(74) *Attorney, Agent, or Firm*—Human Genome Sciences, Inc.

(57) ABSTRACT

The present invention relates to a novel GABA$_A$ receptor ε subunit (GABRE) and an alternative transcript thereof (ET2). More specifically, isolated nucleic acid molecules are provided encoding human GABRE and ET2 receptor subunits. ET2 and GABRE polypeptides are also provided, as are vectors, host cells and recombinant methods for producing the same. The invention further relates to screening methods for identifying agonists and antagonists of ET2 and GABRE activities. Also provided are diagnostic methods for detecting aberrant GABRE and ET2 expression, as well as therapeutic methods for treating disorders involving ET2 and GABRE.

39 Claims, 11 Drawing Sheets

OTHER PUBLICATIONS

Goetz, C.G. and Diederich, N.J., "There is a renaissance of interest in pallidotomy for Parkinson's disease," *Nature Med.* 2(5):510-514 (May 1996).

Gray, R. and Johnston, D., "Rectification of Single GABA-Gated Chloride Channels in Adult Hippocampal Neurons," *J. Neurophysiol.* 54(1):134-142 (1985).

Greger, V. et al., "The γ-Aminobutyric Acid Receptor γ3 Subunit Gene (GABRG3) Is Tightly Linked to the α5 Subunit Gene (GABRA5) on Human Chromosome 15q11-q13 and is Transcribed in the Same Orientation," *Genomics* 26:258-264 (1995).

Hedblom, E. and Kirkness, E.F., "A Novel Class of $GABA_A$ Receptor Subunit in Tissues of the Reproductive System," *J. Biol. Chem.* 272(24):15346-15350 (Jun. 1997).

Hicks, A.A. et al., "Further Evidence for Clustering of Human $GABA_A$ Receptor Subunit Genes: Localization of the $α_6$-Subunit Gene (GABRA6) to Distal Chromosome 5q by Linkage Analysis," *Genomics* 20:285-288 (1994).

Kirkness, E.F. et al., "Isolation, Characterization, and Localization of Human Genomic DNA Encoding the β1 Subunit of the $GABA_A$ Receptor (GABRB1)," *Genomics* 10:985-995 (1991).

Knoll, J.H.M. et al., "Fish ordering of reference markers and of the gene for the α5 subunit of the γ-aminobutyric acid receptor (GABRA5) within the Angelman and Prader-Willi syndrome chromosomal regions," *Human Molecular Genetics* 2(2):183-189 (1993).

Korpi, E.R. and Lüddens, H., "Regional γ-Ambinobutyric Acid Sensitivity of t-Butylbicyclophosphoro[$^{35}$S]thionate Binding Depends on γ-Aminobutyric $Acid_A$ Receptor α Subunit," *Mol. Pharmacol.* 44(1):87-92 (1993).

Lasham, A. et al., "Conserved Organization of γ-Aminobutyric $Acid_A$ Receptor Genes: Cloning and Analysis of the Chicken β4-Subunit Gene," *J. Neurochem.* 57(1):352-355 (1991).

Lewohl, J.M. et al., "Expression of the $α_1$, $α_2$ and $α_3$ isoforms of the $GABA_A$ receptor in human alcoholic brain," *Brain Research* 751:102-112 (Mar. 1997).

Macdonald, R.L. and Olsen, R.W., "$GABA_A$ Receptor Channels," *Annu. Rev. Neurosci.* 17:569-602 (1994).

Matsuyama, S. et al., "GABA modulates neurotransmission in sinus node via stimulation of $GABA_A$ receptor," *Am. J. Physiol.* 264(4):H1057-H1061 (1993).

McLean, P.J. et al., "Mapping of the $α_4$ Subunit Gene (GABRA4) to Human Chromosome 4 Defines an $α_2$-$α_4$-$β_1$-$γ_1$ Gene Cluster: Further Evidence That Modern $GABA_A$ Receptor Gene Clusters Are Derived from an Ancestral Cluster," *Genomics* 26:580-586 (1995).

McLemore, G.L. et al., "Cardiac Noradrenergic Mechanisms Mediate GABA-Enhanced Ouabain Cardiotoxicity," *Pharmacology* 49:343-350 (1994).

Peters, J.A. et al., "Modulation of the $GABA_A$ receptor by depressant barbiturates and pregnane steroids," *Br. J. Pharmacol.* 94(4):1257-1269 (1988).

Rogner, U.C. et al., "A YAC clone map spanning 7.5 megabases of human chromosome band Xq28," *Human Molecular Genetics* 3(12):2137-2146 (1994).

Russek, S.J. and Farb, D.H., "Mapping of the $β_2$ Subunit Gene (GABRB2) to Microdissected Human Chromosome 5q34-q35 Defines a Gene Cluster for the Most Abundant $GABA_A$ Receptor Isoform," *Genomics* 23:528-533 (1994).

Sanna, E. et al., "Actions of the General Anesthetic Propofol on Recombinant $GABA_A$ Receptors: Influence of Receptor Subunits," *J. Pharmacol. Exp. Ther.* 274(1):353-360 (1995).

Sargent, P.B., "The Diversity of Neuronal Nicotinic Acetylcholine Receptors," *Annu. Rev. Neurosci.* 16:403-443 (1993).

Saxena, N.C. and Macdonald, R.L., "Assembly of $GABA_A$ Receptor Subunits: Role of the δ Subunit," *J. Neurosci.* 14(11):7077-7086 (1994).

Schmieden, V. et al., "Agonist pharmacology of neonatal and adult glycine receptor α subunits: identification of amino acid residues involved in taurine activation," *EMBO J.* 11(6):2025-2032 (1992).

Segal, M. and Barker, J.L., "Rat Hippocampal Neurons in Culture: Properties of GABA-Activated CL-Ion Condutance," *J. Neurophysiol.* 51(3):500-515 (1984).

Simmons, D. and Seed, B., "Isolation of a cDNA Encoding CD33, a Differentiation Antigen of Myeloid Progenitor Cells," *J. Immunol.* 141(8):2797-2800 (1988).

Smith, T.F. and Waterman, M.S., "Comparison of Biosequences," *Adv. Appl. Math.* 2:482-489 (1981).

Sommer, B. et al., "The Murine $GABA_A$ Receptor δ-Subunit Gene: Structure and Assignment to Human Chromosome 1," *DNA and Cell Biology* 9(8):561-568 (1990).

Stark, M.J.R., "Multicopy expression vectors carrying the *lac* repressor gene for regulated high-level expression of genes in *Escherichia coli*," *Gene* 51(2-3):255-267 (1987).

Verdoorn, T.A. et al., "Functional Properties of Recombinant Rat $GABA_A$ Receptors Depend upon Subunit Composition," *Neuron* 4(6):919-928 (1990).

Wagstaff, J. et al., "Localization of the Gene Encoding the $GABA_A$ Receptor β3 Subunit to the Angelman/Prader-Willi Region of Human Chromosome 15," *Am. J. Hum. Genet.* 49:330-337 (1991).

Whiting, P.J. et al., "Structure and Pharmacology of Vertebrate $GABA_A$ Receptor Subtypes," *Int. Rev. Neurobiol.* 38:95-138 (1995).

Wilcox, A.S. et al., "Human chromosomal Localization of genes encoding the γ1 and γ2 subunits of the γ-aminobutyric acid receptor indicates that members of this gene family are often clustered in the genome," *Proc. Natl. Acad. Sci. USA* 89:5857-5861 (1992).

Wilke, K. et al., "A Gene in Human Chromosome Band Xq28 (GABRE) Defines a Putative New Subunit Class of the $GABA_A$ Neurotransmitter Receptor," *Genomics* 45:1-10 (Oct. 1997).

Wisden, W. et al., "The Distribution of 13 $GABA_A$ Receptor Subunit mRNAs in the Rat Brain. I. Telencephalon, Diencephalon, Mesencephalon," *J. Neurosci.* 12(3):1040-1062 (1992).

Yang, W. et al., "Identification of the $GABA_A$ receptor subtype mRNA in human pancreatic tissue," *FEBS Lett.* 346:257-262 (1994).

Zhu, W.J. et al., "δ Subunit Inhibits Neurosteroid Modulation of $GABA_A$ Receptors," *J. Neurosci.* 16(21):6648-6656 (Nov. 1996).

NCBI Entrez Nucleotide Query, GenBank Report, Hillier, L. et al., Accession No. R07883 (1995), and Revision History.

NCBI Entrez Nucleotide Query, GenBank Report, Hillier, L. et al., Accession No. R07942 (1995), and Revision History.

NCBI Entrez Nucleotide Query, GenBank Report, Fujiwara, T., Accession No. C17228 (Sep. 1996), and Revision History.

NCBI Entrez Nucleotide Query, GenBank Report, Garret, M., Accession No. Y07637 (Dec. 1996), and Revision History.

NCBI Entrez Nucleotide Query, GenBank Report, Davies, P.A. et al., Accession No. U66661 (Mar. 1997), and Revision History.

NCBI Entrez Nucleotide Query, GenBank Report, Hanna, M.C. et al., Accession No. U92281 (Jan. 1998), and Revision History.

NCBI Entrez Nucleotide Query, GenBank Report, Hanna, M.C. et al., Accession No. U92282 (Jan. 1998), and Revision History.

NCBI Entrez Nucleotide Query, GenBank Report, Hanna, M.C. et al., Accession No. U92283 (Jan. 1998), and Revision History.

NCBI Entrez Nucleotide Query, GenBank Report, Hanna, M.C. et al., Accession No. U92284 (Jan. 1998), and Revision History.

NCBI Entrez Nucleotide Query, GenBank Report, Hanna, M.C. et al., Accession No. U92285 (Jan. 1998), and Revision History.

NCBI Entrez Nucleotide Query, GenBank Report, Wilke, K., Accession No. Y09764 (Jul. 1997), and Revision History.

NCBI Entrez Nucleotide Query, GenBank Report, Wilke, K., Accession No. Y09765 (Jul. 1997), and Revision History.

Harvey, R.J. et al., "Molecular cloning reveals the existence of a fourth γ subunit of the vertebrate brain $GABA_A$ receptor," *FEBS Letters 331*:211-216 (Oct. 1993).

* cited by examiner

FIG. 4

```
ε subunit              MLSKVLPVLLGILILQSRVEGPQTESKNEASSRDVVYGPQPQPLENQLLSEETKSTETETGSRVGKLPEASRIL    75
ε subunit                        ─                                                                
Consensus                        S ε subunit              NTILSNYDHKLRPGIGEKPTVTVELAVNSLGPLSILDMEYTIDIIFSQTWYDERLCYNDTFESLVLNGNVVSQL   150
ε subunit                   L   Y  RP G                  S         MY        Q W D RL       L L
Consensus                                                          ◊

ε subunit              WIPDTFFRNSKRTHEHEITMPNQMVRIYKDGKVLYTIRMTIDAGCSLHMLRFPMDSHSCPLSFSSFSYPENEMIY   225
Consensus              W PDT         N     H T N  R   G LY RT   C  L  P D   C L   SY Y
                                                                       ◊

ε subunit              KWENFKLEINEKNSWKLFQFDFTGVSNKTEIITTPVGDFMVMTIFFNVSRRFGYVAFQNYVPSSVTMLSWVSFW   300
Consensus                 W                 L Q            G     F L R G     Q Y P      S VSFW
                                                                       ◊                 M1

ε subunit              IKTESAPARTSLGITSVLIMTILGTFSRKNFPRVSYITALDFYIAICFVFCFCALLEFAVLNFLIYNQTKAHASP   375
Consensus                      AR  G  TTVLIMTT        R  LP       AD   C  FVF ALE
                                     M2                       ◊              M3

ε subunit              KLRHPRINSRAHARTRARSRACARQHQEAFVCQIVTEGSDGEERPSCCSAQQPPSPGSPEGPRSLCSKLACCEWC   450
Consensus ε subunit              KRFKKYFCMVPDCEGSTWQQGRLCIHVYRLDNYSRVVFPVTFFFENVLYWLVCLNL                      506
Consensus                                                   D   R FP F   N   YW  Y
                                                                        ◊
                                                                            M4
```

Fig. 8

1 AAGCTT AAAAAACTGCAAAAAATAG TTGACTA GTTGAGCGGATAAACAAT
                              -35          Operator 1

50 TAAGAT GTACCCAA TTGTGAGCGGATAACAAT TTCACACATTAA
   -10                Operator 2

94 A GAGGAG AAATTA CATATG
        S/D

US 7,029,870 B1

GABAA RECEPTOR EPSILON SUBUNITS

This application is a continuation-in-part of U.S. patent application Ser. No. 08/888,012, filed Jul. 3, 1997 now abandoned, which is herein incorporated by reference.

BACKGROUND OF THE INVENTION

1. Field of the Invention

The present invention relates to a novel $GABA_A$ receptor ε subunit (GABRE) and an alternative transcript thereof (ET2). More specifically, isolated nucleic acid molecules are provided encoding human GABRE and ET2 receptor subunits. ET2 and GABRE polypeptides are also provided, as are vectors, host cells and recombinant methods for producing the same. The invention further relates to screening methods for identifying agonists and antagonists of ET2 and GABRE activities. Also provided are diagnostic methods for detecting aberrant GABRE and ET2 expression, as well as therapeutic methods for treating disorders involving ET2 and GABRE.

2. Related Art

In mammalian brain, synaptic inhibition of neuronal activity is mediated mainly by the action of the neurotransmitter γ-aminobutyric acid (GABA) at GABA-gated chloride ion channels. GABA is an amino acid derivative which is produced in neurons by the decarboxylation of glutamate.

$GABA_A$ receptor complexes are multi-subunit members of a ligand-gated ion channel gene superfamily. The binding of GABA to these complexes results in the opening of channels across the neuronal cell membrane through which anions flow down their concentration gradients. Chloride ions are the main anions conducted through these channels, and channel opening requires the binding of at least two GABA molecules per $GABA_A$ receptor complex. Thus, the binding of GABA to $GABA_A$ receptor complexes induces an increase in chloride ion conductance across the postsynaptic membrane which alters the chloride ion gradient resulting in both hyperpolarization of this membrane and inhibition of neuronal firing. After interaction with the extracellular regions of the $GABA_A$ receptor complexes, GABA is actively "pumped" back into the prejunctional neurons.

Neurotransmitter responsive ligand-gated ion channels are known to be major targets for psychoactive drugs (Sargeant, P., *Annu. Rev. Neurosci.* 16:403–443 (1993)). The $GABA_A$ receptor complex, for example, is the primary site of action for many of the drugs used to treat anxiety and seizure disorders such as the benzodiazepines, barbiturates and tranquilizers (e.g., Valium and Librium). These receptors serve as molecular control elements through which the levels of anxiety, vigilance, muscle tension, and epileptic activity, as well as other conditions, can be regulated by drug-induced modulations.

Heterogeneity with respect to subunit types which make up transmitter-gated ion channels has been shown for several multi-subunit receptor complexes. The alternative forms of these subunits are generally either encoded by distinct genes or arise due to alternative mRNA splicing (see generally Alberts, B. et al., *Molecular Biology of the Cell*, 3rd edition, Garland Publishing, Inc. (1994)).

The $GABA_A$ receptor complex is believed to assemble into a pentameric structure and, to date, at least fourteen mammalian $GABA_A$ receptor subunits have been identified (α1–6, β1–3, γ1–3, δ, ε). These receptor subunits fall within five families on the basis of amino acid homology (Whiting, P. J., et al., *Int. Rev. Neurobiol.* 38:95–138 (1995); Davies, P. A., et al., *Nature* 385:820–823 (1997)). While the majority of functional receptors contain α/β/γ or α/β/δ subunit combinations, additional subunits combinations can form GABA-activated chloride channels.

Variations in subunit combinations can result in different pharmacological properties being conferred upon the receptor complex (Davies, P. A. et al., *Nature* 385:820–823 (1997); reviewed in Whiting, P. J. et al., *Int. Rev. Neurobiol.* 38:95–138 (1995)). Thus, subpopulations of $GABA_A$ receptor complexes show differing sensitivity to $GABA_A$ steroid modulators, physiological regulation, disease processes, and pharmacological manipulation by drugs (e.g., benzodiazepines). The distributions of mRNAs encoding different $GABA_A$ receptor subunit polypeptides and their subtypes localized in the brain show significant regional variation consistent with pharmacological and biochemical evidence for receptor heterogeneity. Further, alterations in brain specific expression of $GABA_A$ receptor complex subunit polypeptides have been identified in human brain tissues of individuals suffering from alcoholism (Lewohl, J. et al., *Brain Res.* 751:102–112 (1997)).

Thus, the properties of the different subpopulations of $GABA_A$ receptor complexes are determined, at least in part, by the subunits expressed in the particular cell. The $GABA_A$ receptor complex ε subunit, for example, confers several unique pharmacological and biophysical properties when assembled in a $GABA_A$ receptor complex containing α and β subunits (Davies, P. A. et al., *Nature* 385:820–823 (1997)). Most notably, this subunit inhibits the ability of anesthetic agents to potentiate GABA-gated chloride currents.

While much work has been done with $GABA_A$ receptor complexes localized in the brain, functional $GABA_A$ receptors have been identified in rat heart (Matsuyama, S. et al., *Am. J. Physiol.* 264:1057–1061 (1993); McLemore, G. L. et al., *Pharmacology* 49:342–350 (1994)). Further, $GABA_A$ receptor subunit mRNA has also been identified in human pancreatic tissue (Yang, W. et al., *FEBS Lett.* 346:257–262 (1994)) and, more recently, in tissues of the human reproductive system (Hedblom, E. and Kirkness, E., *J. Biol. Chem.* 272:15346–15350 (1997)). Currently, little is known about the subunit composition or pharmacological characteristics of these extra-central nervous system $GABA_A$ receptor complexes.

SUMMARY OF THE INVENTION

The present invention provides isolated nucleic acid molecules comprising polynucleotides encoding the ET2 and GABRE polypeptides having the amino acid sequences shown in SEQ ID NO:2 and SEQ ID NO:42. The nucleotide sequence shown in SEQ ID NO:1 was determined by direct sequencing of PCR amplified ET2 cDNA, as described in Example 1. This DNA sequence contains an open reading frame encoding a polypeptide of about 242 amino acid residues. The amino acid sequence of the ET2 receptor subunit is shown as amino acid residues from about 1 to about 242 in SEQ ID NO:2. The nucleotide sequence shown in SEQ ID NO:41 was determined as described in Example 6. This DNA sequence contains an open reading frame encoding a polypeptide of about 506 amino acid residues. The amino acid sequence of the GABRE receptor subunit is shown as amino acid residues from about −18 to about 488 in SEQ ID NO:42.

The present invention further provides isolated nucleic acid molecules comprising a polynucleotide encoding the GABRE receptor subunit polypeptide having the amino acid sequence shown in SEQ ID NO:42 or the amino acid sequence encoded by the cDNA clone deposited as plasmid DNA on Feb. 25, 1998 and assigned ATCC Deposit Number 209642.

Thus, one aspect of the invention provides an isolated nucleic acid molecule comprising a polynucleotide having a nucleotide sequence selected from the group consisting of: (a) a nucleotide sequence encoding the ET2 or GABRE polypeptide having the complete amino acid sequence in SEQ ID NO:2 or SEQ ID NO:42; (b) a nucleotide sequence encoding the ET2 or GABRE polypeptide having the complete amino acid sequence in SEQ ID NO:2 or SEQ ID NO:42 but minus the N-terminal methionine residue; (c) a nucleotide sequence encoding the GABRE polypeptide having the amino acid sequence at positions from about 1 to about 488 in SEQ ID NO:42; (d) a nucleotide sequence encoding the polypeptide having the amino acid sequence encoded by the cDNA clone contained in ATCC Deposit No. 209642; (e) a nucleotide sequence encoding the mature GABRE polypeptide having the amino acid sequence encoded by the cDNA clone contained in ATCC Deposit 209642; (f) a nucleotide sequence encoding one or more ET2 or GABRE transmembrane domains; (g) a nucleotide sequence encoding the ET2 or GABRE intracellular domain; (h) a nucleotide sequence encoding the GABRE extracellular domain; (i) a nucleotide sequence encoding the ET2 or GABRE protein with all or part of one of more of the transmembrane domains deleted; and (j) a nucleotide sequence complementary to any of the nucleotide sequences in (a), (b), (c), (d), (e), (f), (g), (h), or (i).

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), (d), (e), (f), (g), (h), (i), or (j) above, or a polynucleotide which hybridizes under stringent hybridization conditions to a polynucleotide in (a), (b), (c), (d), (e), (f), (g), (h), (i), or (j) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of an ET2 polypeptide having an amino acid sequence in (a), (b), (c), (d), (e), (f), (g), (h), or (i) above.

The present invention also relates to recombinant vectors, which include the isolated nucleic acid molecules of the present invention, and to host cells containing the recombinant vectors, as well as to methods of making such vectors and host cells and for using them for production of ET2 and GABRE polypeptides, and peptides thereof, by recombinant techniques.

The invention further provides isolated polypeptides having an amino acid sequence selected from the group consisting of: (a) the amino acid sequence of the ET2 polypeptide having the complete 242 amino acid sequence; (b) the amino acid sequence of the GABRE polypeptide having the complete 506 amino acid sequence; (c) the amino acid sequence of the ET2 polypeptide having the complete 242 amino acid sequence but minus the N-terminal methionine residue; (d) the amino acid sequence of the GABRE polypeptide having the complete 506 amino acid sequence but minus the N-terminal methionine residue; (e) the amino acid sequence of the mature GABRE protein; (f) the amino acid sequence of one or more ET2 or GABRE transmembrane domains; (g) the amino acid sequence of the ET2 or GABRE intracellular domain; (h) the amino acid sequence of the GABRE extracellular domain; and (i) the amino acid sequence of the ET2 or GABRE protein with all or part of one or more of the transmembrane domains deleted.

The polypeptides of the present invention also include polypeptides having an amino acid sequence at least 95% identical, and still more preferably 96%, 97%, 98% or 99% identical to those described in (a), (b), (c), (d), (e), (f), (g), (h), or (i) above.

An additional embodiment of this aspect of the invention relates to a peptide or polypeptide which has the amino acid sequence of an epitope-bearing portion of an ET2 or GABRE polypeptide having an amino acid sequence described in (a), (b), (c), (d), (e), (f), (g), (h), or (i) above. Peptides or polypeptides having the amino acid sequence of an epitope-bearing portion of an ET2 or GABRE polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to an ET2 or GABRE polypeptide having an amino acid sequence described in (a), (b), (c), (d), (e), (f), (g), (h), or (i) above. Such antibodies are useful diagnostically or therapeutically as described below.

The present invention also provides a screening method for identifying compounds capable of enhancing or inhibiting an ET2 and/or GABRE receptor subunit activity, which involves contacting cells which express an ET2 and/or GABRE receptor subunit with both a stimulatory molecule and a candidate compound, assaying a cellular response, and comparing the cellular response to both a first standard cellular response, made in absence of the candidate compound, and a second standard cellular response, made in absence of an ET2 and/or GABRE polypeptide, whereby an increased cellular response in comparison to both the first and second standards indicates that the compound is an agonist and a decreased cellular response in comparison to both the first and second standards indicates that the compound is an antagonist.

In another aspect, a screening assay for agonists and antagonists is provided which involves determining the effect a candidate compound has on the binding of ligands to an ET2 and/or GABRE receptor subunit. In particular, the method involves contacting an ET2 and/or GABRE receptor subunit with one or more additional GABAA receptor subunit polypeptides and a candidate compound and determining whether ET2 and/or GABRE receptor subunit ligand binding activity is increased or decreased due to the presence of the candidate compound.

For a number of disorders involving GABAA receptors, it is believed that significantly higher or lower levels of ET2 and/or GABRE expression can be detected in certain tissues (e.g., heart, placenta, pancreas, spleen, thymus, prostate, testis, ovary, small intestine, and colon) or bodily fluids (e.g., serum, plasma, urine, synovial fluid or spinal fluid) taken from an individual having such a disorder, relative to a "standard" ET2 and/or GABRE receptor subunit expression level, i.e., an ET2 and/or GABRE receptor subunit expression level in tissue or bodily fluids from an individual not having the disorder. Thus, the invention provides a diagnostic method useful during diagnosis or prognosis of a disorder related to ET2 and/or GABRE expression levels which are significantly higher or lower than standard levels.

This diagnostic method involves: (a) assaying the ET2 and/or GABRE receptor subunit expression level in cells or body fluid of an individual; (b) comparing the ET2 and/or GABRE expression level with a standard ET2 and/or GABRE receptor subunit expression level, whereby a significant increase or decrease in the assayed ET2 and/or GABRE receptor subunit expression level compared to the standard expression level is indicative of a disorder involving ET2 and/or GABRE receptor subunit expression.

An additional aspect of the invention is related to a method for treating an individual in need of an increased level of ET2 and/or GABRE activity in the body comprising administering to such an individual a composition comprising a therapeutically effective amount of an isolated ET2 and/or GABRE polypeptide of the invention or an agonist of ET2 and/or GABRE receptor subunit activity.

A still further aspect of the invention is related to a method for treating an individual in need of a decreased level of ET2 and/or GABRE receptor subunit activity in the body comprising, administering to such an individual a composition comprising a therapeutically effective amount of an antagonist of ET2 and/or GABRE receptor subunit activity.

BRIEF DESCRIPTION OF THE FIGURES

FIG. 4 shows the amino-acid sequence of the human ε-subunit (SEQ ID NO:42). The ε-subunit polypeptide is aligned with a consensus sequence of all known mammalian $GABA_A$ receptor subunits. The potential signal sequence (S) and four putative transmembrane domains (M1–M4) are highlighted by lines under the corresponding peptide sequences. Eight differences between the ε-subunit sequence and the consensus are indicated by diamonds.

FIG. 5A shows the concentration-dependent activation of currents recorded from cells transfected with either α2/β1 (open circles) or α2/β1/ε (filled circles) cDNAs. From the logistic fit (Adodra, S. and Hales, T. G., Br. J. Pharmacol. 115:953–960 (1995)), the $EC_{50}$ values are 16.4 and 11.2 μM, and Hill slopes are 1.3 and 1.1, respectively. Data points represent current amplitudes recorded from at least 3 cells, normalized to the maximum current of each cell. FIG. 5B shows the current-voltage relationships for responses evoked by 100 μM GABA, recorded from cells transfected with α2/β1 (open circles) or α2/β1/ε (filled circles) cDNAs. From the respective exponential and linear fits to the data points (Adodra, S. and Hales, T. G., Br. J. Pharmacol. 115:953–960 (1995)), currents reversed at 4.4 and 5.7 mV. Data points represent the mean current amplitudes recorded from at least 4 different cells and normalized to the peak current amplitude of each cell. The insets are superimposed traces showing averages of two leak-subtracted currents recorded from individual cells when held at voltages between 60 and −60 mV. FIG. 5C shows the ratio of GABA (100 μM)-evoked current amplitudes, recorded at 60 and −60 mV, for different α/β and α/β/ε subunit combinations. Data are mean values from 4–18 cells.

FIG. 6A shows the modulation by pregnanolone of [$^{35}$S]TBPS binding to the membranes of cells transfected with either α2/β1 (open circles) or α2/β/ε (filled circles) cDNAs. FIG. 6B shows the modulation of GABA (100 μM)-evoked currents by pregnanolone, recorded from cells expressing α2/β1 (open circles) or α2/β/ε (filled circles) cDNAs. Data points represent mean values from at least 4 cells, fitted using the logistic function (Adodra, S. and Hales, T. G., Br. J. Pharmacol. 115:953–960 (1995)). The insets are superimposed traces showing currents recorded in the absence or presence (asterisks) of pregnanolone (100 nM). FIG. 6C shows the modulation of [$^3$H]muscimol binding to cell membranes by pregnanolone (circles) and pentobarbital (squares) after transfection with either α1/β3 (open symbols) or α1/β3/ε (filled symbols) cDNAs. FIG. 6D shows the effects of pentobarbital (100 μM) and propofol (3 μM) on GABA (100 μM) evoked currents recorded from cells expressing different α/β and α/β/ε subunit combinations. Histogram bars represent mean data from at least 4 cells.

FIG. 8 shows the nucleotide sequence of the regulatory elements of the pHE4a promoter (SEQ ID NO:46). The two lac operator sequences, the Shine-Delgarno sequence (S/D), and the terminal HindIII and NdeI restriction sites (italicized) are indicated.

DETAILED DESCRIPTION

Figure 1:
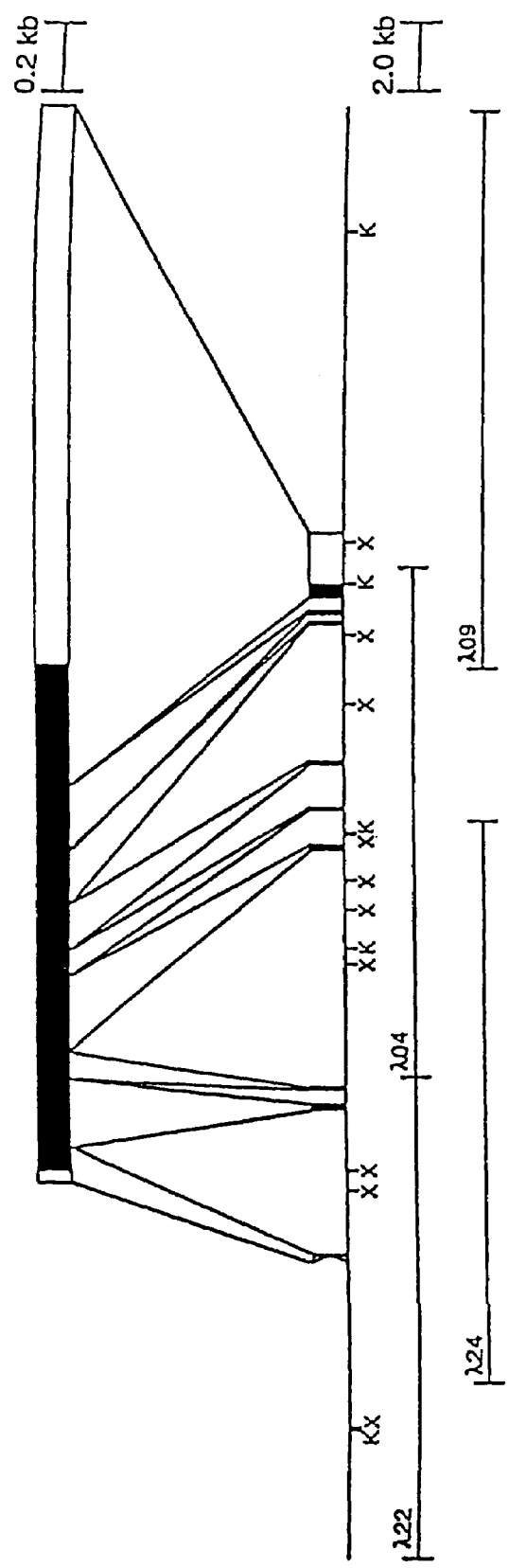
FIG. 1 shows the genomic structure of GABRE. The top illustration represents the human ε subunit mRNA. The protein-coding region is shaded. The start and end of exons are indicated by oblique lines that join the mRNA to the genomic DNA below. The representation of genomic DNA indicates the location of exons (boxes) and restriction sites for KpnI and XbaI (K, X). The bottom portion of the figure illustrates the cloned fragments of human genomic DNA.

The present invention provides isolated nucleic acid molecules comprising a polynucleotide encoding an ET2 polypeptide having the amino acid sequence shown in SEQ ID NO:2, which was determined by sequencing a PCR amplified cDNA clone, as described in Example 1. The present invention also provides isolated nucleic acid molecules comprising a polynucleotide encoding a GABRE polypeptide having the amino acid sequence shown in SEQ ID NO:42, which was determined as described in Example 6. The amino acid sequence of the ET2 polypeptide of the present invention is identical to approximately the carboxy terminal half of GABRE (amino acids from about 247 to about 488 in SEQ ID NO:42).

The present invention further provides isolated nucleic acid molecules comprising a polynucleotide encoding a GABRE polypeptide having the amino acid sequence shown in SEQ ID NO:42. A cDNA clone containing a nucleotide sequence corresponding to nucleotides 11–1593 in SEQ ID NO:41 was deposited on Feb. 25, 1998 at the American Type Culture Collection, 10801 University Blvd, Manassas, Va. 20110-2209, USA, and given accession number 209642. The deposited clone is inserted in the pCDM8 plasmid (Invitrogen, San Diego, Calif.) using the XhoI and PstI restriction endonuclease cleavage sites. The XhoI site was lost during the insertion process.

The material identified as ATCC accession number 209642 was deposited as plasmid DNA which must be inserted into a suitable host cell for bacterial amplification. One suitable host cell is Escherichia coli, and the deposited vector confers ampicillin and tetracycline resistance in transformed E. coli containing the P3 episome.

Nucleic Acid Molecules

All amino acid sequences of polypeptides encoded by DNA molecules determined herein were predicted by translation of cDNA sequences, which were sequenced as described in Examples 1 and 6. As is known in the art, any nucleotide sequence determined herein may contain some errors. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in SEQ ID NO:1 or SEQ ID NO:41, a nucleic acid molecule of the present invention encoding an ET2 or GABRE polypeptide may be obtained using standard cloning and screening procedures, such as those for cloning cDNAs using mRNA as starting material. Illustrative of the invention, the nucleic acid molecule described in SEQ ID NO:1 was identified in multiple tissues, including heart, placenta, pancreas, spleen, thymus, prostate, testis, ovary, small intestine, and colon. The determined nucleotide sequence of the ET2 cDNA of SEQ ID NO:1 contains an open reading frame encoding a protein of about 242 amino acid residues. The amino acid sequence of the predicted ET2 receptor subunit is shown in SEQ ID NO:2 from amino acid residue about 1 to residue about 242.

Also illustrative of the invention, the nucleic acid molecule described in SEQ ID NO:41 was identified in a number of brain tissues, including amygdala and thalamus. The determined nucleotide sequence of the GABRE cDNA of SEQ ID NO:41 contains an open reading frame encoding a protein of about 506 amino acid residues. The amino acid sequence of the predicted GABRE receptor subunit is shown in SEQ ID NO:42 from amino acid residue about −18 to residue about 488.

The present invention also provides the mature form(s) of the GABRE protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature GABRE polypeptide having the amino acid sequence encoded by the cDNA clone contained in the plasmid identified as ATCC Deposit No. 209642 and as shown in SEQ ID NO:42. By the mature GABRE protein having the amino acid sequence encoded by the cDNA clone contained in the plasmid identified as ATCC Deposit No. 209642 is meant the mature form(s) of the GABRE protein produced by expression in a mammalian cell (e.g., COS cells, as described below) of the complete open reading frame encoded by the human DNA sequence of the clone contained in the vector in the deposited plasmid. As indicated below, the mature GABRE protein having the amino acid sequence encoded by the cDNA clone contained in ATCC Deposit No. 209642 may or may not differ from the predicted "mature" GABRE protein shown in SEQ ID NO:42 (amino acids from about 1 to about 488) depending on the accuracy of the predicted cleavage site based on computer analysis.

Methods for predicting whether a protein has a secretory leader as well as the cleavage point for that leader sequence are available. For instance, the methods of McGeoch (Virus Res. 3:271–286 (1985)) and von Heinje (Nucleic Acids Res. 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

The leader sequence for the GABRE protein is predicted to consist of amino acid residues from about −18 to about −1 in SEQ ID NO:42, while the mature GABRE protein is predicted to consist of residues from about 1 to about 488.

The ET2 receptor subunit is believed to be translated from a mRNA splice variant of the GABRE genomic coding sequence. Alternative splicing has previously been demonstrated for several subunits of the GABAA receptor complex (reviewed in Whiting, P. J., et al., Int. Rev. Neurobiol. 38:95–138 (1995)).

As used herein the phrase "splice variant" refers to RNA molecules initially transcribed from the same genomic DNA sequence but have undergone alternative splicing. Alternative splicing occurs when the sequence of a primary RNA transcript is spliced, wherein generally one or more introns are removed, and more than one mRNA molecule is produced. Further, each of the mRNA molecules may encode different amino acid sequences. The term "splice variant" also refers to the proteins encoded by the above RNA molecules produced by alternative splicing.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 3872–3874 of the nucleotide sequence shown in SEQ ID NO:1 or at positions 41–43 of the nucleotide sequence shown in SEQ ID NO:41 and DNA molecules which comprise sequences substantially different from those described above but which, due to the degeneracy of the genetic code, still encode an ET2 or GABRE receptor subunit. Of course, the genetic code is well known in the art. Thus, it would be routine for one skilled in the art to generate such degenerate variants.

In another aspect, the invention provides isolated nucleic acid molecules encoding the GABRE polypeptide having an amino acid sequence as encoded by the cDNA clone contained in the plasmid deposited as ATCC Deposit No. 209642 on Feb. 25, 1998. In a further aspect, nucleic acid molecules are provided encoding the full-length ET2 or GABRE polypeptide lacking the N-terminal methionine. The invention also provides an isolated nucleic acid molecule having the nucleotide sequence shown in SEQ ID NO:1 or SEQ ID NO:41, or a nucleic acid molecule having a sequence complementary to that of SEQ ID NO:1 or SEQ ID NO:41. Such isolated molecules, particularly DNA molecules, are useful as probes for gene mapping, for in situ hybridization with chromosomes, and for detecting expression of ET2 or GABRE nucleotide sequences in human tissue, for instance, by Northern blot analysis.

The present invention is further directed to fragments of the isolated nucleic acid molecules described herein. By a fragment of an isolated nucleic acid molecule having the nucleotide sequence shown in SEQ ID NO:1 or SEQ ID NO:41 is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950, 6000, 6050, 6100, or 6146 nt in length of the sequence shown in SEQ ID NO:1 are also useful according to the present invention. Similarly, larger DNA fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, or 3100 nt in length of the sequence shown in SEQ ID NO:41 are also useful according to the present invention as are fragments corresponding to most, if not all, of the nucleotide sequence of the cDNA clone contained in the plasmid deposited as ATCC Deposit No. 209642 or as shown in SEQ ID NO:41.

By a fragment at least 20 nt in length, for example, is intended fragments which include 20 or more contiguous bases from the nucleotide sequence as shown in SEQ ID NO:1 or SEQ ID NO:41. Since the nucleotide sequences shown in SEQ ID NO:1 and SEQ ID NO:41 are provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding polypeptides comprising the ET2 receptor subunit transmembrane domains (predicted to constitute amino acid residues from about 15 to about 36, from about 42 to about 62, from about 75 to about 95, and from about 219 to about 240 in SEQ ID NO:2) and the ET2 receptor subunit intracellular domain (predicted to constitute amino acid residues from about 96 to about 218 in SEQ ID NO:2). Preferred nucleic acid fragments of the present invention further include nucleic acid molecules encoding polypeptides comprising the GABRE receptor subunit transmembrane domains (predicted to constitute amino acid residues from about 261 to about 282, from about 288 to about 308, from about 321 to about 341, and from about 465 to about 486 in SEQ ID NO:42), the GABRE receptor subunit extracellular domain (predicted to constitute amino acid residues from about 1 to about 260 in SEQ ID NO:42), and the GABRE receptor subunit intracellular domain (predicted to constitute amino acid residues from about 342 to about 464 in SEQ ID NO:42). The amino acid residues constituting the ET2 and GABRE receptor subunit domains have been predicted by computer analysis. Thus, as one of ordinary skill would appreciate, the amino acid residues constituting these domains may vary slightly (e.g., by about 1 to about 3 amino acid residues) depending on the criteria used to define each domain.

Preferred nucleic acid fragments of the present invention also include nucleic acid molecules encoding epitope-bearing portions of the ET2 and GABRE receptor subunit proteins. Methods for determining such epitope-bearing portions of the ET2 and GABRE proteins are described in detail below.

In addition, the invention present inventors have identified the following cDNA clones related to extensive portions of SEQ ID NO:1: HUKAU66R (SEQ ID NO:43) and HPLBB96F (SEQ ID NO:44).

In another aspect, the invention provides isolated nucleic acid molecules comprising polynucleotides which hybridize under stringent hybridization conditions to a portion of the polynucleotide in a nucleic acid molecule of the invention described above, for instance, the cDNA sequences shown in SEQ ID NO:1 and SEQ ID NO:41, or the cDNA clone contained in ATCC Deposit No. 209642. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the cDNA sequence shown in SEQ ID NO:1 or SEQ ID NO:41), for instance, a portion 50–750 nt in length, or even to the entire length of the reference polynucleotide, are also useful as probes according to the present invention, as are polynucleotides corresponding to most, if not all, of the nucleotide sequence shown in SEQ ID NO:1 or SEQ ID NO:41. By a portion of a polynucleotide of "at least 20 nt in length," for example, is intended 20 or more contiguous nucleotides from the nucleotide sequence of the reference polynucleotide (e.g., the nucleotide sequence as shown in SEQ ID NO: 1 or SEQ ID NO:41). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since ET2 and GABRE receptor subunit cDNA sequences are provided in SEQ ID NO:1 and SEQ ID NO:41, generating polynucleotides which hybridize to a portion of the ET2 or GABRE receptor subunit cDNA molecule would be routine to the skilled artisan. For example, restriction endonuclease cleavage or shearing by sonication of an ET2 or GABRE receptor subunit cDNA clone could easily be used to generate DNA portions of various sizes which are polynucleotides that hybridize to a portion of the ET2 or GABRE receptor subunit cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the ET2 or GABRE receptor subunit cDNA shown in SEQ ID NO:1 and SEQ ID NO:41, respectively), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an ET2 or GABRE polypeptide may include, but are not limited to the coding sequence for the polypeptide and additional sequences, such as those encoding a leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 3 7:767–778 (1984). As discussed below, other such fusion proteins include the ET2 receptor subunit fused to Fc at the C- or N-terminus.

The present invention further relates to variants of the nucleic acid molecules of the present invention, which encode portions, analogs or derivatives of an ET2 or GABRE receptor subunit. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of an ET2 or GABRE receptor subunit or portions thereof. Also especially preferred in this regard are conservative substitutions. Most highly preferred are nucleic acid molecules encoding the protein having the amino acid sequence shown in SEQ ID NO:2 or SEQ ID NO:42.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2 or SEQ ID NO:42; (b) a nucleotide sequence encoding the polypeptide having the amino acid sequence in SEQ ID NO:2 or SEQ ID NO:42, but lacking the N-terminal methionine; (c) a nucleotide sequence encoding amino acids from about 1 to about 488 sequence in SEQ ID NO:42; (d) a nucleotide sequence encoding the polypeptide having the amino acid sequence encoded by the cDNA clone contained in ATCC Deposit No. 209642; (e) a nucleotide sequence encoding the mature GABRE polypeptide having the amino acid sequence encoded by the cDNA clone contained in ATCC Deposit No. 209642; (f) a nucleotide sequence encoding one or more ET2 or GABRE receptor subunit transmembrane domains; (g) a nucleotide sequence encoding the ET2 or GABRE intracellular domain; (h) a nucleotide sequence encoding the ET2 or GABRE protein with all or part of one or more of the transmembrane domains deleted; (i) a nucleotide sequence encoding the GABRE receptor subunit extracellular domain; and (j) a nucleotide sequence complementary to any of the nucleotide sequences in (a), (b), (c), (d), (e), (f), (g), (h), or (i).

By a polynucleotide having a nucleotide sequence at least, for example, 95% "identical" to a reference nucleotide sequence encoding an ET2 or GABRE polypeptide is intended that the nucleotide sequence of the polynucleotide is identical to the reference sequence except that the polynucleotide sequence may include up to five point mutations per each 100 nucleotides of the reference nucleotide sequence encoding the ET2 or GABRE receptor subunit. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or SEQ ID NO:41 can be determined conventionally using known computer programs such as the Bestfit® program (Wisconsin Sequence Analysis Package, Version 8 for Unix, Genetics Computer Group, University Research Park, 575 Science Drive, Madison, Wis. 53711). Bestfit® uses the local homology algorithm of Smith and Waterman, *Advances in Applied Mathematics* 2:482–489 (1981), to find the best segment of homology between two sequences. When using Bestfit® or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1 or SEQ ID NO:41, irrespective of whether they encode a polypeptide having ET2 or GABRE receptor subunit activity. This is because even where a particular nucleic acid molecule does not encode a polypeptide having ET2 or GABRE receptor subunit activity, one of skill in the art would still know how to use the nucleic acid molecule, for instance, as a hybridization probe or a polymerase chain reaction (PCR) primer. Uses of the nucleic acid molecules of the present invention that do not encode a polypeptide having ET2 or GABRE receptor subunit activity include, inter alia, (1) isolating the ET2 or GABRE receptor subunit nucleotide sequence, or allelic variants thereof, in a cDNA library; (2) in situ hybridization (e.g., "FISH") to metaphase chromosomal spreads to provide precise chromosomal location of the gene encoding the ET2 and GABRE receptor subunits, as described in Verma et al., *Human Chromosomes: A Manual of Basic Techniques*, Pergamon Press, New York (1988); and (3) Northern blot analysis for detecting ET2 or GABRE receptor subunit mRNA expression in specific tissues.

Preferred, however, are nucleic acid molecules having sequences at least 95%, 96%, 97%, 98% or 99% identical to the nucleic acid sequence shown in SEQ ID NO:1 or SEQ ID NO:41 which do, in fact, encode a polypeptide having ET2 or GABRE receptor subunit activity. By "a polypeptide having ET2 or GABRE receptor subunit activity" is intended polypeptides exhibiting activity similar, but not necessarily identical, to an activity of the ET2 or GABRE receptor subunit of the invention (e.g., the full-length protein or a functional domain thereof), as measured in a particular biological assay. For example, ET2 or GABRE receptor subunit activity may be measured by co-transfection of cells with $GABA_A$ receptor α and β subunits and a polypeptide suspected of having ET2 or GABRE receptor activity. After transfection, the effect that the candidate polypeptide has on the activation of the $GABA_A$ receptor complex can be determined by measurement of concentration-dependent activation of chloride currents as described in Davies, P. et al., *Nature* 385:820–823 (1997), and Example 6, in the presence and absence of the candidate polypeptide. Additional assays for ET2 and GABRE activities are described in Davies, P. et al., *Br. J. Pharmacol.* 120:899–909 (1997), Davies, P. et al, *Nature* 385:820–823 (1997), and Example 6.

Further, since the ET2 and GABRE polypeptide are each believed to assemble into GABAA receptor complexes, ET2 or GABRE receptor subunit activity can be measured by determining the binding affinity of a candidate polypeptide towards other members of this complex. In vivo and in vitro techniques for measuring such binding activity are described in Ausbel, F. et al., eds., *Current Protocols in Molecular Biology*, John Wiley & Sons, Inc. (1997), Chapter 20. These techniques include the use of interaction trap/two hybrid assays and binding assays involving GST fusion proteins.

Thus, "a polypeptide having ET2 or GABRE receptor subunit activity" includes polypeptides that exhibit ET2 or GABRE receptor subunit activity, in the above-described assays. Although the degree of activity need not be identical to that of the ET2 or GABRE receptor subunit, preferably, "a polypeptide having ET2 or GABRE receptor subunit activity" will exhibit substantially similar activity as compared to the ET2 or GABRE protein (i.e., the candidate polypeptide will exhibit greater activity or not more than about twenty-fold less and, preferably, not more than about ten-fold less activity relative to the reference ET2 or GABRE protein).

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence shown in SEQ ID NO:1 or SEQ ID NO:41 will encode "a polypeptide having ET2 or GABRE receptor subunit activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having ET2 or GABRE protein activity. This is so because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Vectors and Host Cells

The present invention also relates to vectors which include the isolated DNA molecules of the present invention, host cells which are genetically engineered with the recombinant vectors, and the production of ET2 or GABRE polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EPA 0464533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EPA 0 232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *J. Molec. Recognition* 8:52–58 (1995) and K. Johanson et al., *J. Biol. Chem.* 270:9459–9471 (1995).

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figure 7:
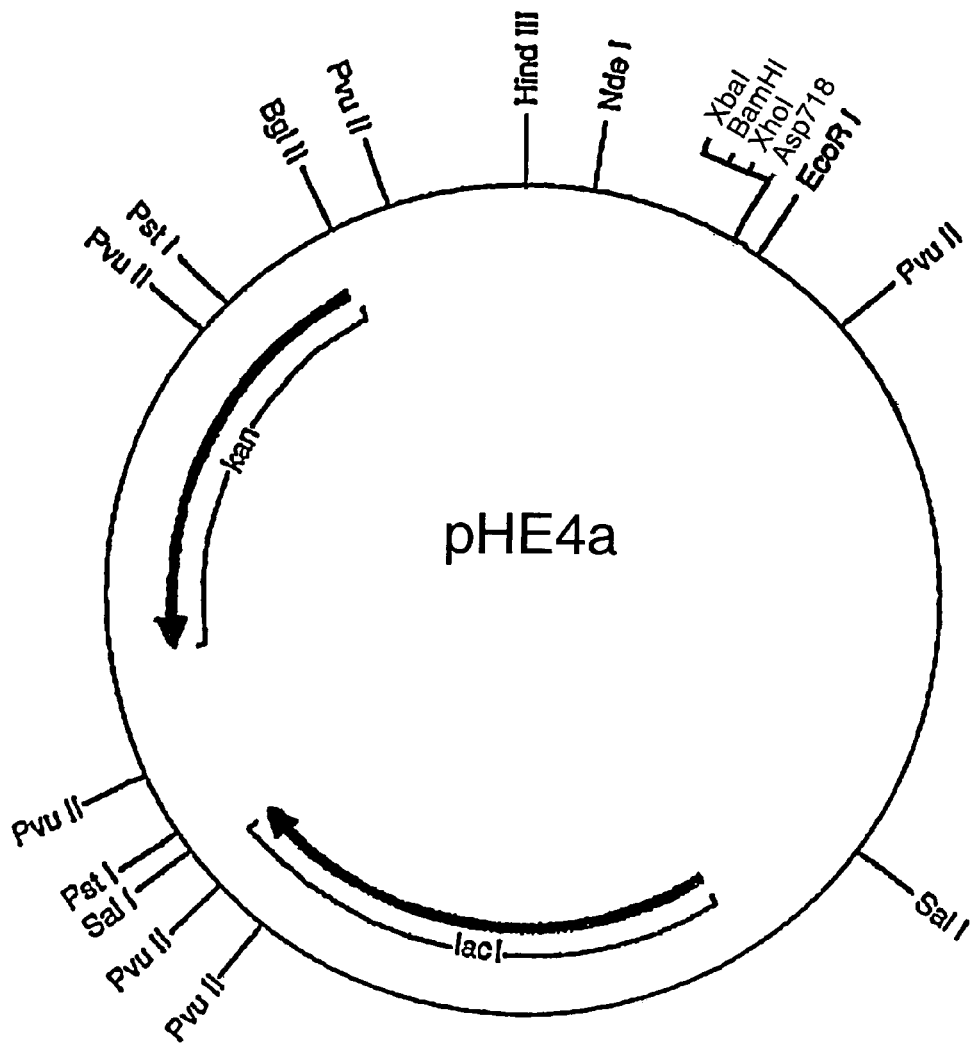
FIG. 7 shows a schematic representation of the pHE4a expression vector (SEQ ID NO:45). The locations of a number of restriction endonuclease cleavage sites, the kanamycin resistance marker gene, and the lacIq coding sequence are indicated.

As summarized in FIG. 7 and FIG. 8, components of the pHE4a vector (SEQ ID NO:45) include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. The pHE4a vector was deposited with the ATCC on Feb. 25, 1998, and given accession number 209645.

A nucleotide sequence encoding either ET2 (SEQ ID NO:1) or GABRE (SEQ ID NO:41), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding ET2 (SEQ ID NO:1) or GABRE (SEQ ID NO:41) having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). The ET2 or GABRE protein thus is not produced in appreciable quantities in uninduced host cells containing the pHE4a vector. Induction of these host cells by the addition of an agent such as IPTG, however, results in the expression of the ET2 or GABRE coding sequence.

The promoter/operator sequences of the pHE4a vector (SEQ ID NO:46) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4a vector except for the ET2 and GABRE coding sequence. Features of the pHE4a vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO:45).

ET2 and GABRE receptor subunits can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

ET2 and GABRE Polypeptides and Fragments

The invention further provides isolated ET2 polypeptides having the amino acid sequence in SEQ ID NO:2 and SEQ ID NO:42, as well as peptides or polypeptides comprising portions of the sequences shown in SEQ ID NO:2 and SEQ ID NO:42. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the ET2 and GABRE receptor subunits can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the ET2 and GABRE receptor subunits which show substantial ET2 or GABRE receptor subunit activity or which include regions of the ET2 or GABRE protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2 or SEQ ID NO:42 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as an IgG Fc fusion region peptide or leader or secretory sequence or a sequence which is employed for purification of the polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the ET2 or GABRE protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the ET2 and GABRE receptor subunits of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given ET2 or GABRE polypeptide, or mutant thereof, will not be more than 50, 40, 30, 20, 10, 5, or 3, depending on the objective.

Amino acids in the ET2 or GABRE protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as binding activity towards other members of the GABA$_A$ receptor complex. Sites that are critical for such binding can also be determined by structural analysis such as crystallization, nuclear magnetic resonance or photoaffinity labeling (Smith et al., *J. Mol. Biol.* 224: 899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the ET2 or GABRE polypeptide can be substantially purified by the one-step method described in Smith and Johnson, *Gene* 67:31–40 (1988).

The polypeptides of the present invention include a polypeptide comprising amino acids about 1 to about 242 in SEQ ID NO:2; a polypeptide comprising amino acids about 2 to about 242 in SEQ ID NO:2; a polypeptide comprising one or more of the ET2 receptor subunit transmembrane domains (amino acids from about 15 to about 36 in SEQ ID NO:2, amino acids from about 42 to about 62 in SEQ ID NO:2, amino acids from about 75 to about 95 in SEQ ID NO:2, amino acids from about 219 to about 240 in SEQ ID NO:2); a polypeptide comprising the intracellular domain of the ET2 receptor subunit (amino acids from about 96 to about 218 in SEQ ID NO:2); a polypeptide comprising the ET2 receptor subunit with all or part of one or more of the transmembrane domains deleted; as well as polypeptides at least 95% identical, more preferably at least 96%, 97%, 98% or 99% identical to the polypeptide of SEQ ID NO:2, and also include portions of such polypeptides with at least 30 amino acids and more preferably at least 50 amino acids.

The polypeptides of the present invention include a polypeptide comprising amino acids about –18 to about 488 in SEQ ID NO:42; a polypeptide comprising amino acids about –17 to about 488 in SEQ ID NO:42; a polypeptide comprising amino acids about 1 to about 488 in SEQ ID NO:42; a polypeptide comprising amino acids about 1 to about 488 in SEQ ID NO:42; a polypeptide comprising one or more of the GABRE receptor subunit transmembrane domains (amino acids from about 261 to about 282 in SEQ ID NO:42, amino acids from about 288 to about 308 in SEQ ID NO:42, amino acids from about 321 to about 341 in SEQ ID NO:42, amino acids from about 465 to about 486 in SEQ ID NO:42); a polypeptide comprising the extracellular domain of the GABRE receptor subunit (amino acids from about 1 to about 260 in SEQ ID NO:42); a polypeptide comprising the intracellular domain of the GABRE receptor subunit (amino acids from about 342 to about 464 in SEQ ID NO:42); a polypeptide comprising the GABRE receptor subunit with all or part of one or more of the transmembrane domains deleted; as well as polypeptides at least 95% identical, more preferably at least 96%, 97%, 98% or 99% identical to the polypeptide of SEQ ID NO:42, and also include portions of such polypeptides with at least 30 amino acids and more preferably at least 50 amino acids.

By a polypeptide having an amino acid sequence at least, for example, 95% "identical" to a reference amino acid sequence of an ET2 or GABRE polypeptide is intended that the amino acid sequence of the polypeptide is identical to the reference sequence except that the polypeptide sequence may include up to five amino acid alterations per each 100 amino acids of the reference amino acid of the ET2 or GABRE receptor subunit. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or SEQ ID NO:42 can be determined conventionally using known computer programs such the Bestfit® program (Wisconsin Sequence Analysis Package, Version 8 for Unix, Genetics Computer Group, University Research Park, 575 Science Drive, Madison, Wis. 53711). When using Bestfit® or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting ET2 or GABRE protein expression as described below or as agonists and antagonists capable of enhancing or inhibiting ET2 or GABRE receptor subunit function. Further, such polypeptides can be used in the yeast two-hybrid system to "capture" ET2 or GABRE receptor subunit binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., Antibodies that React with Predetermined Sites on Proteins, *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A., General Method for the Rapid Solid-Phase Synthesis of Large Numbers of Peptides: Specificity of Antigen-Antibody Interaction at the Level of Individual Amino Acids, *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "ET2 and GABRE Polypeptides and Fragments" is hereby incorporated herein by reference.

As one of skill in the art will appreciate, ET2 or GABRE polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing other molecules than the monomeric ET2 or GABRE protein or protein fragments alone (Fountoulakis et al., J. Biochem. 270:3958–3964 (1995)).

Disease Diagnosis and Prognosis

It is believed that tissues in mammals with certain disease states express significantly altered levels of the ET2 and/or GABRE receptor subunit and mRNA encoding the ET2 and/or GABRE receptor subunit when compared to a corresponding "standard" mammal, i.e., a mammal of the same species not having the disease state. Further, it is believed that altered levels of the ET2 and/or GABRE receptor subunit can be detected in certain body fluids (e.g., sera, plasma, urine, and spinal fluid) from mammals with these disease states when compared to sera from mammals of the same species not having the disease. Thus, the invention provides a diagnostic method useful during diagnosis, which involves assaying the expression level of the gene encoding the ET2 and GABRE receptor subunits in mammalian cells or body fluid and comparing the gene expression level with a standard expression level, whereby a significantly altered gene expression level in comparison to the standard is indicative of certain diseases. One variation of this method involves assaying for the level of mRNA molecules encoding either ET2 or GABRE polypeptides and comparing these mRNA level with standard ET2 or GABRE mRNA levels. Another variation involves assaying for the level of mRNA molecules encoding both ET2 and GABRE polypeptides and comparing these mRNA level with each other to determine a ratio of ET2 to GABRE expression and comparing this ratio to a standard ET2 to GABRE ratio. A further variation involves assaying for the level of mRNA molecules encoding both ET2 and GABRE polypeptides to determine the total amount of ET2 and GABRE mRNA molecules and comparing this total amount to a standard total amount.

Where the diagnosis of a disease state has already been made according to conventional methods, the present invention is useful as a prognostic indicator, whereby patients exhibiting significantly altered ET2 and/or GABRE receptor subunit expression will experience a worse clinical outcome relative to patients expressing the gene encoding these proteins at a level which deviates less from that of the standard.

By "assaying the expression level of the gene encoding the ET2 and GABRE receptor subunits" is intended qualitatively or quantitatively measuring or estimating the level of the ET2 and/or GABRE protein or the level of the mRNA encoding the ET2 and/or GABRE receptor subunit in a first biological sample either directly (e.g., by determining or estimating absolute protein level or mRNA level) or relatively (e.g., by comparing to the ET2 and/or GABRE protein level or mRNA level in a second biological sample).

Preferably, the ET2 and/or GABRE protein level or mRNA level in the first biological sample is measured or estimated and compared to a standard ET2 and/or GABRE protein level or mRNA level, the standard being taken from a second biological sample obtained from an individual not having the disease state. As will be appreciated in the art, once standard ET2 and GABRE protein levels or mRNA levels are known, they can be used repeatedly as a standard for comparison.

By "biological sample" is intended any biological sample obtained from an individual, cell line, tissue culture, or other source which contains ET2 and/or GABRE protein or mRNA. Biological samples include mammalian body fluids (e.g., sera, plasma, urine, synovial fluid and spinal fluid) and tissues (e.g., testicular, heart, prostate, placenta, small intestine and colon tissues) which contain ET2 and/or GABRE protein or mRNA. Methods for obtaining tissue biopsies and body fluids from mammals are well known in the art. Where the biological sample is to include mRNA, a tissue biopsy is the preferred source.

The present invention is useful for detecting diseases in mammals. In particular the invention is believed to be useful in diagnosing disease states in mammals, including schizophrenia, Huntington's Chorea, alcoholism, muscle spasms and rigidity, sleep disorders, seizure disorders (e.g., epilepsy), anxiety related disorders, AIDS related dementia, Alzheimer's disease, and Parkinson's disease. Preferred mammals include monkeys, apes, cats, dogs, cows, pigs, horses, rabbits and humans. Particularly preferred mammals are humans.

Total cellular RNA can be isolated from a biological sample using any suitable technique such as the single-step guanidinium-thiocyanate-phenol-chloroform method described in Chomczynski and Sacchi, Anal. Biochem. 162: 156–159 (1987). Levels of mRNA encoding the ET2 and/or GABRE receptor subunit are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. ET2 and/or GABRE receptor subunit cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the ET2 and/or GABRE receptor subunit). Northern blot analysis can be performed as described above.

Preferably, levels of mRNA encoding the ET2 and/or GABRE receptor subunit are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the ET2 and/or GABRE receptor subunit) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying ET2 and/or GABRE protein levels in a biological sample can occur using any art-known method. Preferred for assaying ET2 and/or GABRE protein levels in a biological sample are antibody-based techniques. For example, ET2 and/or GABRE protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of ET2 and/or GABRE protein for Western-blot or dot/slot assay (Jalkanen, M., et al., *J. Cell. Biol.* 101:976–985 (1985); Jalkanen, M., et al., *J. Cell. Biol.* 105:3087–3096(1987)). In this technique, which is based on the use of cationic solid phases, quantitation of ET2 and/or GABRE protein can be accomplished using isolated ET2 and/or GABRE protein as a standard. This technique can also be applied to body fluids. With these samples, molar concentrations of ET2 and GABRE proteins will aid to set standard values of ET2 and GABRE protein content for different body fluids, like serum, plasma, urine, spinal fluid, etc. The normal appearance of ET2 and GABRE protein amounts can then be set using values from healthy individuals, which can be compared to those obtained from a test subject.

Other antibody-based methods useful for detecting ET2 and GABRE receptor subunit expression include immunoassays, such as the enzyme linked immunosorbent assay (ELISA) and the radioimmunoassay (RIA). For example, monoclonal antibodies with specificity for an ET2 or GABRE receptor subunit can be used both as an immunoabsorbent and as an enzyme-labeled probe to detect and quantify the ET2 or GABRE protein. The amount of ET2 or GABRE protein present in the sample can be calculated by reference to the amount present in a standard preparation using a linear regression computer algorithm. Such an ELISA for detecting a tumor antigen is described in Iacobelli et al., *Breast Cancer Research and Treatment* 11: 19–30 (1988). In another ELISA assay, two distinct specific monoclonal antibodies can be used to detect either ET2 or GABRE protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting ET2 and/or GABRE protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

In addition to assaying ET2 and/or GABRE protein levels in a biological sample obtained from an individual, ET2 and GABRE proteins can also be detected in vivo by imaging. Antibody labels or markers for in vivo imaging of ET2 and/or GABRE protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

An ET2 and/or GABRE receptor subunit-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain ET2 and/or GABRE protein. In vivo tumor imaging is described in S. W. Burchiel et al., "Immunopharmacokinetics of Radiolabelled Antibodies and Their Fragments" (Chapter 13 in Tumor Imaging: The Radiochemical Detection of Cancer, S. W. Burchiel and B. A. Rhodes, eds., Masson Publishing Inc. (1982)).

ET2 and GABRE receptor subunit-specific antibodies for use in the present invention can be raised against the intact ET2 or GABRE receptor subunit or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (MAb) is meant to include intact molecules as well as antibody fragments (such as, for example, Fab and F(ab')$_2$ fragments) which are capable of specifically binding to the ET2 and/or GABRE receptor subunit. Fab and F(ab')$_2$ fragments lack the Fc fragment of intact antibody, clear more rapidly from the circulation, and may have less non-specific tissue binding of an intact antibody (Wahl et al., *J. Nucl. Med* 24:316–325 (1983)). Thus, these fragments are preferred.

The antibodies of the present invention may be prepared by any of a variety of methods. For example, cells expressing the ET2 and/or GABRE receptor subunit, or an antigenic fragment thereof, can be administered to an animal in order to induce the production of sera containing polyclonal antibodies. In a preferred method, a preparation of either ET2 or GABRE protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or ET2 and/or GABRE receptor subunit binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563–681). In general, such procedures involve immunizing an animal (preferably a mouse) with an ET2 or GABRE receptor subunit antigen or, more preferably, with an ET2 or GABRE receptor subunit-expressing cell. Suitable cells can be recognized by their capacity to bind anti-ET2 or anti-GABRE receptor subunit antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Manassas, Va. 20110-2209. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding to an ET2 and/or GABRE receptor subunit antigen.

Alternatively, additional antibodies capable of binding to an ET2 and/or GABRE receptor subunit antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, ET2 and/or GABRE receptor subunit-specific antibodies are used to immunize an animal, preferably a mouse. The splenocytes of such an animal are then used to produce hybridoma cells, and the hybridoma cells are screened to identify clones which produce an antibody whose ability to bind to the ET2 and/or GABRE receptor subunit-specific antibody can be blocked by the ET2 and/or GABRE receptor subunit antigen. Such antibodies comprise anti-idiotypic antibodies to the ET2 and/or GABRE receptor subunit-specific antibody and can be used to immunize an animal to induce formation of further ET2 and/or GABRE receptor subunit-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, ET2 and/or GABRE receptor subunit-binding fragments can be produced through the application of recombinant DNA technology or through synthetic chemistry.

Where in vivo imaging is used to detect enhanced levels of ET2 and/or GABRE protein in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *Bio-Techniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the ET2 and/or GABRE receptor subunit-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is a preferred isotope where in vivo imaging is used since its avoids the problem of dehalogenation of the $^{125}I$ or $^{131}I$-labeled monoclonal antibody by the liver. In addition, this radionucleotide has a more favorable gamma emission energy for imaging (Perkins et al., Eur. J. Nucl. Med 10:296–301 (1985); Carasquillo et al., J. Nucl. Med. 28:281–287 (1987)). For example, $^{111}In$ coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include $^{157}Gd$, 55Mn, $^{162}Dy$, $^{52}Tr$, and $^{56}Fe$.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., Clin. Chim. Acta 70:1–31 (1976), and Schurs et al., Clin. Chim. Acta 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Agonists and Antagonists of ET2 and GABRE Receptor Subunit Activity

Variations in the subunit composition of the $GABA_A$ receptor complex can alter ligand induced responses (reviewed in Whiting, P. et al., Int. Rev. Neurobiol. 38:95–138 (1995)). The presence of a γ subunit in a $GABA_A$ receptor complex, for example, confers sensitivity to benzodiazepines upon the complex while only marginally reducing the complex's affinity for GABA. Further, the presence of a GABRE subunit inhibits the ability of anesthetic agents to potentiate GABA-gated chloride currents (see Example 6). In a similar fashion, the integration of the ET2 receptor subunit is believed to modulate $GABA_A$ receptor complex activity by altering the binding affinity of this complex to various ligands. The ET2 and GABRE receptor subunits are further believed to enhance the binding affinity of $GABA_A$ receptor complex to ligands which do not generally bind the complex with high affinity.

In one aspect, the present invention is directed to a method for inhibiting an activity of the ET2 and/or GABRE receptor subunit (e.g., binding of the ET2 and/or GABRE receptor subunit to members of the $GABA_A$ receptor complex, modulation of $GABA_A$ receptor complex activities), which involves administering to a cell which expresses an ET2 and/or GABRE polypeptide an effective amount of an antagonist of ET2 and/or GABRE receptor subunit activity. Antagonists can include soluble forms of the ET2 or GABRE receptor subunit, antibodies directed against the ET2 or GABRE polypeptide, and antisense molecules.

In a further aspect, the present invention is directed to a method for increasing ET2 and/or GABRE receptor subunit activity, which involves administering to a cell which expresses an ET2 and/or GABRE polypeptide an effective amount of an agonist. Agonists can include soluble forms of the ET2 or GABRE receptor subunit.

By "agonist" is intended naturally occurring and synthetic compounds capable of enhancing one or more activity of the ET2 and/or GABRE receptor subunit. Such agonists include modified forms of the ET2 or GABRE polypeptide and agents which increase expression of ET2 and/or GABRE receptor subunits. By "agonistic activity" is intended the enhancement of one or more ET2 and/or GABRE receptor subunit activities. By "antagonist" is intended naturally occurring and synthetic compounds capable of inhibiting one or more activities of the ET2 and/or GABRE receptor subunit. Such antagonists include modified forms of the ET2 or GABRE polypeptide and agents which decrease expression of ET2 and/or GABRE receptor subunits. By "antagonistic activity" is intended the inhibition of one or more ET2 and/or GABRE receptor subunit activities. Whether any candidate "agonist" or "antagonist" of the present invention can enhance or inhibit ET2 and/or GABRE receptor subunit activity can be determined using art-known assays, including those described in more detail below.

Thus, in a further aspect, a screening method is provided for determining whether a candidate compound is capable of enhancing or inhibiting ET2 and/or GABRE receptor subunit activity. The method involves contacting cells which express (1) ET2 and/or GABRE receptor subunit polypeptides and (2) other components of the $GABA_A$ receptor complex with (1) a molecule known to elicit a GABAA receptor complex induced cellular response (e.g., a $GABA_A$ receptor complex ligand), referred to herein as a "stimulatory molecule," and (2) a candidate compound, assaying a cellular response, and comparing the cellular response to a first standard cellular response, the first standard cellular response being assayed when contact is made with the stimulatory molecule in absence of the candidate compound, whereby an increased cellular response over the first standard indicates that the candidate compound is a potential agonist of ET2 and/or GABRE receptor subunit activity and a decreased cellular response compared to the first standard indicates that the candidate compound is a potential antagonist of ET2 and/or GABRE receptor subunit activity. A final determination of whether the candidate compound is an agonist or antagonist of ET2 and/or GABRE receptor subunit activity is made by comparing the effect this compound has on GABAA receptor complex activity to a second standard cellular response, the second standard cellular response being assayed when cells are contacted with the stimulatory molecule and candidate compound in the absence of the ET2 and/or GABRE receptor subunit, wherein agonistic or antagonistic activity which occurs in the presence of ET2 and/or GABRE but not in its absence indicates that the candidate compound alters GABAA receptor complex function in conjugation with the ET2 and/or GABRE receptor subunit.

By "assaying a cellular response" is intended qualitatively or quantitatively measuring a cellular response to a candidate compound (e.g., alteration of binding of the ET2 and/or GABRE polypeptide to other members of the GABAA receptor complex, GABAA receptor complex activation). By the invention, a cell expressing an ET2 and/or GABRE receptor subunit polypeptide can be contacted with either an endogenously or exogenously administered stimulatory molecule.

By a "$GABA_A$ receptor complex ligand" is intended naturally occurring, recombinant, and synthetic ligands that are capable of binding to a $GABA_A$ receptor complex and inducing the ligand/receptor signaling pathway (e.g., $GABA_A$ receptor complex activation). Also intended are compounds which bind to the GABAA receptor complex and may be used to assay ET2 and/or GABRE receptor subunit activity. $GABA_A$ receptor complex ligands include, but are not limited to, GABA, benzodiazepines, steroids (e.g., dehydroepiandrosterone), barbiturates, picrotoxin, ethanol, loreclezole, anesthetics, and zinc.

In an additional aspect, a screening method is provided for determining whether a candidate compound is capable of enhancing or inhibiting ET2 and/or GABRE receptor subunit activity, wherein the candidate compound and stimulatory molecule are the same. This method involves contacting cells which express (1) the ET2 and/or GABRE receptor subunit and (2) the $GABA_A$ receptor complex with a candidate compound, assaying a cellular response, and comparing the cellular response to a standard cellular response, the standard being assayed when contact is made with the stimulatory molecule in absence of the ET2 and/or GABRE receptor subunit, whereby a difference in the cellular response with respect to the standard indicates that the candidate compound is either an agonist or antagonist of ET2 and/or GABRE receptor subunit activity.

ET2 and/or GABRE receptor subunit activity can be measured in cells co-transfected with genetic material encoding the ET2 and/or GABRE polypeptide and additional GABAA receptor subunits (e.g., α and β subunits) followed by measurement of chloride currents activation in response to administration of a stimulatory molecule (e.g., a $GABA_A$ receptor complex ligand). Further, as noted above, antagonists and agonists of ET2 and/or GABRE receptor subunit activity can be identified by comparing the cellular response in the presence of both a stimulatory molecule and a candidate compound, wherein antagonistic or agnostic activity towards the cellular response in the presence of the ET2 and/or GABRE receptor subunit but not in their absence indicates that the candidate compound is either an antagonist or agonist of ET2 and/or GABRE receptor subunit activity.

Another method for identifying antagonists and agonists of ET2 and/or GABRE receptor subunit activity involves screening for compounds which either enhance or inhibit binding of labeled $GABA_A$ receptor complex ligand molecules (e.g., GABA) to cells which have the receptor complex on their surfaces. This method involves transfecting a cell with genetic material encoding (1) the ET2 and/or GABRE receptor subunit and (2) additional members of the GABAA receptor complex, such that the cell expresses $GABA_A$ receptor complex binding sites on its surface, and contacting the cell with a candidate compound in the presence of a labeled form of a $GABA_A$ receptor complex ligand, e.g., labeled with a radioactive isotope. The amount of labeled ligand bound to the receptor complex is measured. If the compound, for example, competitively binds to the receptor, as determined by a reduction of labeled ligand which binds to the receptors, the binding of labeled ligand to the receptor is inhibited. As above, a determination of whether the candidate compound exerts its influence on the binding of a ligand to the $GABA_A$ receptor complex via the ET2 and/or GABRE receptor subunit will involve the measurement of $GABA_A$ receptor complex ligand binding in the presence of the candidate compound and both in the presence and absence of the ET2 and/or GABRE receptor subunit.

Soluble forms of the polypeptides of the present invention may be utilized in the ligand binding assay described above. Such forms of the ET2 and/or GABRE receptor subunit are candidate agonists and antagonists of the present invention and may alter ligand binding to the $GABA_A$ receptor complex by binding to either the labeled $GABA_A$ receptor complex ligand (e.g., GABA) or to the $GABA_A$ receptor complex itself.

Antagonist according to the present invention include soluble forms of the ET2 and/or GABRE receptor subunits (e.g., fragments of the ET2 or GABRE receptor subunit shown in SEQ ID NO:2 and SEQ ID NO:42, respectively). Such soluble forms of the receptor, which may be naturally occurring or synthetic and may antagonize ET2 and/or GABRE receptor subunit activity by binding to either the GABAA receptor complex or stimulatory molecules. Antagonists of the present invention also include antibodies specific for the ET2 and/or GABRE receptor subunit and ET2 and/or GABRE receptor subunit-Fc fusion proteins which contain regions of the ET2 and/or GABRE polypeptide required for binding to the $GABA_A$ receptor complex. Techniques for producing antibodies which bind to a protein of interest and fusion proteins are well known in the art and are described, for example, in Ausbel, F. et al., eds., *Current Protocols in Molecular Biology*, John Wiley & Sons, Inc. (1997) (see, e.g., Chapters 11 and 16), the entire disclosure of which is hereby incorporated herein by reference.

Antibodies of the present invention may be prepared by any of a variety of methods using ET2 or GABRE receptor subunit immunogens of the present invention. Such ET2 or GABRE receptor subunit immunogens include the ET2 and GABRE receptor subunit proteins shown in SEQ ID NO:2 and SEQ ID NO:42 and polypeptide fragments of the ET2 and GABRE receptor subunits comprising the extracellular, intracellular and transmembrane domains, or any combination thereof.

Polyclonal and monoclonal antibody agonist or antagonist of the present invention can be raised according to the methods disclosed in Tartaglia and Goeddel, *J. Biol. Chem.* 267:4304–4307(1992)); Tartaglia et al., *Cell* 73:213–216 (1993)), and PCT Application WO 94/09137.

In a preferred method, antibodies according to the present invention are mAbs. Such mAbs can be prepared using hybridoma technology (Kohler and Millstein, *Nature* 256: 495–497 (1975) and U.S. Pat. No. 4,376,110; Harlow et al., *Antibodies*: A Laboratory Manual, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the ET2 and/or GABRE receptor subunit domains are also candidate agonist and antagonist according to the present invention. Such binding compounds can be "captured" using the yeast two-hybrid system (Fields and Song, *Nature* 340:245–246

(1989)). A modified version of the yeast two-hybrid system has been described by Roger Brent and his colleagues (Gyuris, J. et al., *Cell* 75:791–803 (1993); Zervos, A. S. et al., *Cell* 72:223–232 (1993)). Preferably, the yeast two-hybrid system is used according to the present invention to capture compounds which bind to one or more domains of the ET2 and/or GABRE receptor subunits. Such compounds are good candidate agonists and antagonists of the present invention.

Using the two-hybrid assay described above, the domains of the ET2 and GABRE receptor subunits, or portions thereof, may be used to identify cellular proteins which interact with the receptor subunit in vivo. Such an assay may also be used to identify ligands with potential agonistic or antagonistic activity of ET2 and/or GABRE receptor subunit function. This screening assay has previously been used to identify proteins which interact with the cytoplasmic domain of the murine TNF-RII and led to the identification of two receptor associated proteins. Rothe, M. et al., *Cell* 78:681 (1994). Such proteins and amino acid sequences which bind to the cytoplasmic and transmembrane domains of the ET2 and GABRE receptor subunits are good candidate agonist and antagonist of the present invention.

Further, the effect that a candidate compound has on the binding of the ET2 and/or GABRE receptor subunit to the $GABA_A$ receptor complex ligands in vitro may also be measured to identify compounds which are agonists and antagonists of ET2 and/or GABRE receptor subunit activity. Techniques for measuring such binding activity are described, for example, in Ausbel, F. et al., eds., *Current Protocols in Molecular Biology*, John Wiley & Sons, Inc. (1997), Chapter 20, and include binding assays using GST fusion proteins.

ET2 and GABRE receptor subunit agonists and antagonists of the present invention may be employed to stimulate $GABA_A$ receptor complex ligand induced activities, such as the modulation of $GABA_A$ receptor complex activity. Thus, the agonists and antagonists of the present invention may be employed to alter the cellular response of the $GABA_A$ receptor complex to $GABA_A$ receptor complex ligands.

Therapeutics and Modes of Administration

The ET2 and GABRE receptor subunit are each believed to be involved in a number of disease states involving the $GABA_A$ receptor complex (e.g., schizophrenia, Huntington's Chorea, muscle spasms and rigidity, sleep disorders, seizure disorders (e.g., epilepsy), alcoholism, anxiety related disorders, AIDS related dementia, Alzheimer's disease, Parkinson's disease, and additional diseases associated with neurological function). ET2 and GABRE receptor subunit involvement in a disease state may result from either under-expression or overexpression of both or one of these receptor subunits, increased or decreased sensitivity of the $GABA_A$ receptor complex to a ligand, or either enhanced or decreased binding of the ET2 and/or GABRE polypeptide to the $GABA_A$ receptor complex. Thus, important targets for inhibitors of ET2 and GABRE receptor subunit functions are ligand binding domains and domains necessary for interaction with other members of the $GABA_A$ receptor complex. Therefore, included within the scope of the invention are molecules capable of inhibiting or stimulating ET2 and/or GABRE receptor subunit activity. Such molecules include antibodies specific for the ET2 and/or GABRE polypeptide and derivatives of the ET2 and/or GABRE receptor subunit. Suitable derivatives of the ET2 and/or GABRE receptor subunit include all of the domains of these proteins and fragments thereof.

It will be appreciated that conditions caused by a decrease in the standard or normal level of ET2 and/or GABRE receptor subunit activity in an individual, can be treated by administration of ET2 and/or GABRE protein or an agonist of ET2 and/or GABRE receptor subunit activity. Thus, the invention further provides a method of treating an individual in need of an increased level of ET2 and/or GABRE receptor subunit activity comprising administering to such an individual a pharmaceutical composition comprising an effective amount of an isolated ET2 and/or GABRE polypeptide of the invention, or agonist of ET2 and/or GABRE receptor subunit activity, effective to increase the ET2 and/or GABRE receptor subunit activity level in such an individual.

It will further be appreciated that conditions caused by an increase in the standard or normal level of ET2 and/or GABRE receptor subunit activity in an individual, can be treated by administration of an antagonist of ET2 and/or GABRE receptor subunit activity. Thus, the invention further provides a method of treating an individual in need of a decreased level of ET2 and/or GABRE receptor subunit activity comprising administering to such an individual a pharmaceutical composition comprising an effective amount of an antagonist of ET2 and/or GABRE receptor subunit activity, effective to decrease the ET2 and/or GABRE receptor subunit activity level in such an individual.

The composition containing the ET2 and/or GABRE polypeptide, agonist, or antagonist will be formulated and dosed in a fashion consistent with good medical practice, taking into account the clinical condition of the individual patient (especially the side effects of the treatment), the site of delivery of the composition, the method of administration, the scheduling of administration, and other factors known to practitioners. The "effective amount" of an ET2 and/or GABRE polypeptide, agonist, or antagonist for purposes herein, is thus determined by such considerations.

Further, compositions containing an ET2 and/or GABRE polypeptide, agonist, or antagonist may contain mixtures of different molecules formulated to either increase or decrease $GABA_A$ receptor complex activity. For example, an ET2 and/or GABRE polypeptide may be combined with an agonist of ET2 and/or GABRE receptor subunit activities to treat an affliction associated with decreased ET2 and/or GABRE receptor subunit activity.

As a general proposition, the total pharmaceutically effective amount of ET2 and/or GABRE polypeptide, agonist, or antagonist administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, an ET2 polypeptide, a GABRE polypeptide, an agonist, an antagonist, or combination thereof will typically be administered at a dose rate of about 1 µg/kg/hour to about 50 µg/kg/1 hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing an ET2 polypeptide, a GABRE polypeptide, an agonist, an antagonist, or combination thereof may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The ET2 polypeptide, GABRE polypeptide, agonist, antagonist, or combination thereof is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release compositions also include liposomally entrapped ET2 and/or GABRE polypeptide, agonist, or antagonist compositions. Liposomes containing an ET2 polypeptide, a GABRE polypeptide, an agonist, an antagonist, or combination thereof are prepared by methods known per se: DE 3,218,121; Epstein et al, *Proc. Natl. Acad. Sci.* (*USA*) 82:3688–3692 (1985); Hwang et al., *Proc. Natl. Acad. Sci.* (*USA*) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal effectiveness of the therapy.

For parenteral administration, in one embodiment, the composition to be administered is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the ET2 polypeptide, GABRE polypeptide, agonist, antagonist, or combination thereof uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides (e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG).

The ET2 polypeptide, GABRE polypeptide, agonist, antagonist, or combination thereof is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of salts.

An ET2 polypeptide, a GABRE polypeptide, an agonist, an antagonist, or combination thereof to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

ET2 polypeptides, GABRE polypeptides, agonists, antagonists, or combination thereof ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered aqueous solution containing 1% (w/v) of the composition to be administered, and the resulting mixture is lyophilized. The infusion solution is prepared by reconstituting the lyophilized composition using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA encoding the ET2 and GABRE receptor subunits. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Having generally described the invention, the same will be more readily understood by reference to the following examples, which are provided by way of illustration and are not intended as limiting.

EXAMPLES

Example 1

Alternative Transcripts of a Gene Encoding the GABA$_A$ Receptor ε Subunit on Chromosome Xq28

Introduction

In mammalian brain, synaptic inhibition of neuronal activity is mediated mainly by the action of γ-aminobutyric acid (GABA) at GABA$_A$ receptors. The GABA$_A$ receptors are oligomeric proteins, composed of homologous subunits, that can conduct chloride currents across the synaptic membrane. An extensive range of GABA$_A$ receptor subunits has been identified through the isolation and expression of cDNA clones. Several of these subunits have been shown to confer specific properties to the recombinant receptors in which they assemble. The spatial variation of subunit expression patterns in the brain is thought to account for the pharmacological diversity of this receptor family (reviewed in Macdonald, R. L., and Olsen, R. W., *Annu. Rev. Neurosci.* 17:569–602 (1994); Whiting, P. J., et al., *Int. Rev. Neurobiol.* 38:95–138 (1995)).

Fourteen mammalian GABA$_A$ receptor subunits have been classified within five families (α1–6, β1–3, γ1–3, δ, ε) on the basis of amino acid homology (Whiting, P. J., et al., *Int. Rev. Neurobiol.* 38:95–138 (1995); Davies, P. A., et al., *Nature* 385:820–823 (1997)). With the exception of the ε subunit, all of the subunit genes have been assigned to human chromosomal regions. Most of the subunit genes are located in three clusters, on chromosomes 4, 5 and 15 (Buckle, V. J., et al., *Neuron* 3:647–654 (1989); Wagstaff, J., et al., *Am. J. Hum. Genet.* 49:330–337 (1991); Wilcox, A. S., et al., *Proc. Natl. Acad. Sci. USA* 89:5857–5861 (1992); Knoll, J. H., et al., *Hum. Mol. Genet.* 2:183–189 (1993); Russek, S. J., and Farb, D. H., *Genomics* 23:528–533 (1994); Hicks, A. A., et al., *Genomics* 20:285–288 (1994); McLean, P. J., et al., *Genomics* 26:580–586 (1995); Greger, V., et al., *Genomics* 26:258–264(1995)). Only GABRA3 (on chromosome Xq28) and GABRD (chromosome 1) appear to be isolated from other members of the gene family (Buckle, V. J., et al., *Neuron* 3:647–654 (1989); Sommer, B., et al., *Cell Biol.* 9:561–568 (1990)).

The ε subunit represents a distinct subunit class that was identified recently in human brain (Davies, P. A., et al., *Nature* 385:820–823 (1997)). This subunit confers several unique pharmacological and biophysical properties to the GABA$_A$ receptors in which it assembles. Most notably, it blocks the ability of anesthetic agents to potentiate GABA-gated chloride currents. The ε subunit transcript is expressed at particularly high levels in the subthalamic nucleus, and is therefore a potential target for pharmacological manipulation of neuronal pathways within the basal ganglia.

Owing to the distinctive sequence of the ε subunit protein, it was of interest to compare the characteristics of the human ε subunit gene (GABRE) with those of related family members. Here, we describe the structure, location and expression patterns of GABRE. Unexpectedly, an alternative transcript of the gene was detected during the course of this study. The sequence and expression pattern of this mRNA indicate that its cellular role is distinct from that of the ε subunit transcript.

Materials and Methods

Cloning and Mapping of GABRE

Two libraries of human genomic DNA, cloned in λDASH II and λFIX (Stratagene), were screened at high stringency (Kirkness, E. F., et al., *Genomics* 10:985–995 (1991)) with two $^{32}$P-labeled fragments of the human ε subunit cDNA (nucleotides 20–328 and 695–1329 of GenBank Accession No. U66661 (SEQ ID NO:41)). Sixteen hybridizing clones were obtained from approximately 2×10$^6$ plaques. Overlapping inserts were determined by restriction fragment mapping and Southern blotting. Exons and flanking introns were sequenced from templates of purified λ DNA using the Dye Terminator Cycle Sequencing system (Applied Biosystems). The sequences of three genomic fragments that contain all of the exons are shown in SEQ ID NO:3, SEQ ID NO:4, and SEQ ID NO:5.

Sequencing of an ε Subunit Gene Fragment from Rat

The cDNA sequence of the rat ε subunit was used to design primers for of rat genomic DNA by PCR. Two overlapping fragments of the rat ε subunit gene were amplified with primer pairs that correspond to nucleotides 1–24 (forward), 2170–2193 (reverse) and 2167–2190 (forward), 5936–5959 (reverse) of SEQ ID NO:6. Inverse PCR (Ochman, H., et al., in "PCR Protocols", (Innis, M. A., et al., eds), Academic Press, San Diego, (1990), pp. 219–227) was used to obtain an overlapping fragment from the 3' end of the rat gene. For these reactions, the primers corresponded to nucleotides 6851–6874 (reverse) and 6881–6904 (forward) in SEQ ID NO:6. Amplification at 95° C. for 45 s, 60° C. for 1 min, 72° C. for 2 min was performed for 30 cycles using the XL PCR system (Perkin Elmer). Amplified products were purified from agarose gels and sequenced directly.

Cloning of an Alternative Transcript

A transcript of GABRE that contains sequences from intron 6 was isolated from human testes cDNA using the Marathon cDNA amplification system (Clontech). Initially, the 5'- and 3'-ends of several cDNA clones were obtained by anchored PCR, using primers that correspond to nucleotides 1087–1110 (reverse), 215–237 (reverse) or 5667–5692 (forward) of SEQ ID NO:1. The terminal sequences of the amplified cDNAs were then used to design primers for amplification of a contiguous cDNA. These correspond to nucleotides 1–24 (forward) and 6121–6146 (reverse) of SEQ ID NO:1. Amplification at 95° C. for 45 s, 60° C. for 1 min, 72° C. for 2 min was performed for 40 cycles using the XL PCR system (Perkin Elmer). Amplified products were purified from an agarose gel and sequenced directly.

Northern Blot Analysis

Fragments of GABRE were generated by PCR and labeled with $^{32}$P using the NEblot random priming system (New England Biolabs). Probe A was derived from exon 9 (nucleotides 8620–9626 of SEQ ID NO:5). Probe B was derived from the human ε subunit cDNA, and corresponds to exons 4, 5 and 6 of GABRE (nucleotides 390–780 of U66661 (SEQ ID NO:41)). Probes C and E were derived from intron 6 (nucleotides 3959–4934 and 5757–6352 of SEQ ID NO:5, respectively). The quality, and relative quantities of mRNA samples was assessed using a $^{32}$P-labeled fragment of the human GAPD cDNA (nucleotides 789–1140, Tokunaga, K., et al., Cancer Res. 47:5616–5619 (1987)). All probes were hybridized sequentially with the same human RNA blots (Clontech) according to the manufacturer's instructions. Blots were washed at 60° C. in 0.1×SSC, 0.1% SDS prior to exposure. Between each hybridization, the blots were stripped of probe by boiling in 0.5% SDS.

Chromosomal Localization

A human/rodent somatic cell hybrid mapping panel (Coriell) was used to assign GABRE to the X-chromosome. A fragment of intron 6 was amplified from 200 ng DNA by PCR. The primers corresponded to nucleotides 6886–6910 (forward) and 7094–7118 (reverse) of SEQ ID NO:5. Amplification at 95° C. for 45 s, 60° C. for 1 min, 72° C. for 2 min was performed for 30 cycles using the GeneAmp system (Perkin Elmer). Localization to chromosome Xq28 was achieved by the same method, using DNA from somatic cell hybrids (GM07298, GM111000 and GM10663; Coriell), and YAC clones (IB0502 and CH0479; Rogner, U. C., et al., Hum. Mol. Genet. 3:2137–2146 (1994)). For additional analysis of YAC clones, a fragment of GABRE intron 1 was amplified with primers that correspond to nucleotides 162–185 (forward) and 463–486 (reverse) of SEQ ID NO:3. A fragment of GABRE exon 9 was amplified with primers that correspond to nucleotides 8139–8162 (forward) and 8250–8273 (reverse) of SEQ ID NO:5. Fragments from the 5' and 3' regions of GABRA3 were amplified with primer pairs that correspond respectively to nucleotides 47–70 (forward), 126–149 (reverse) and 1423–1446 (forward), 1551–1574 (reverse) of the human α3 subunit cDNA (GenBank Accession No. S62908). Amplified products were purified from agarose gels and sequenced directly to confirm their identity.

Sequence Analysis

Nucleotide sequences were analyzed with algorithms of the Wisconsin Package (Genetics Computer Group). Human and rat genomic sequences were aligned using the default parameters of GAP. Conserved regions of the two sequences were highlighted graphically using PLOTSIMILARITY with a window of 150 nucleotides. Potential secondary structures of the ET2 transcript were identified using FOLDRNA. The program was used to identify potential stem loops within the first 2 kb of the transcript. The minimum free energy of individual stem loops was calculated using the same program.

Results and Discussion

Gene Structure and Chromosomal Location

GABRE was identified within the overlapping inserts of four phage λ clones (FIG. 1). The subunit protein is encoded by nine exons that span 22 kb. The exon-intron junctions sequences of GABRE are shown in Table 2. Exon and intron sequences are written in uppercase and lowercase letters respectively. The length of each exon and intron is also indicated. The numbering of exon sequences in Table 2 corresponds to a full-length cDNA that encodes the human ε subunit (GenBank Accession No. U66661 (SEQ ID NO:41)).

All of the exons are flanked by canonical acceptor and donor splice sites (Breathnach, R., and Chambon, P., Annu. Rev. Biochem. 50:349–383 (1981); Table 2). The locations of these splice sites are conserved precisely with all other members of this subunit gene family for which complete gene structures have been resolved (Sommer, B., et al., Cell Biol. 9:561–568 (1990); Kirkness, E. F., et al., Genomics 10:985–995 (1991); Lasham, A., et al., J. Neurochem. 57:352–355 (1991)). The nucleotide sequence of the spliced exons is identical to the sequence of a human ε subunit cDNA clone (Davies, P. A., et al., Nature 385:820–823 (1997)), with the exception of a single base substitution within exon 3, corresponding to base 344 of the cDNA sequence. This substitution (T for G) changes the deduced amino acid sequence by replacing $Ala_{102}$ with Ser. This residue is not conserved between different classes of $GABA_A$ receptor subunits, and the functional consequences of this apparent polymorphism are unknown at present.

TABLE 2

| Exon | | kb | Intron | | kb |
|---|---|---|---|---|---|
| 1 | | | | | |
| 1 | CGCGACCTCC . . . TCCAGTCGAG (SEQ ID NO:7) (SEQ ID NO:8) 97 | ≥0.096 | gtgagtctcc . . . aatgttatag (SEQ ID NO:9) (SEQ ID NO:10) | | 4.1 |
| 2 | GGTCGAGGGA . . . GGCATTGGAG (SEQ ID NO:11) (SEQ ID NO:12) 305 | 0.218 | gtgaggagca . . . tcccttatag (SEQ ID NO:13) (SEQ ID NO:14) | | 0.448 |
| 3 | AGAAGCCCAC . . . CCTAGACATG (SEQ ID NO:15) (SEQ ID NO:16) 383 | 0.068 | gtgagtacta . . . ttcccaccag (SEQ ID NO:17) (SEQ ID NO:18) | | 7.1 |
| 4 | GAATACACCA . . . ACACAATTAG (SEQ ID NO:19) (SEQ ID NO:20) 604 | 0.221 | gtatgtcaag . . . tcccttccag (SEQ ID NO:21) (SEQ ID NO:22) | | 1.055 |
| 5 | GATGACCATT . . . TTCTCTAGCT (SEQ ID NO:23) (SEQ ID NO:24) 687 | 0.083 | gtgagtacct . . . tcctttccag (SEQ ID NO:25) (SEQ ID NO:26) | | 1.306 |
| 6 | TTTCCTATCC . . . ACCCCAGTTG (SEQ ID NO:27) (SEQ ID NO:28) 825 | 0.138 | gtaagcgtgc . . . gtcttttcag (SEQ ID NO:29) (SEQ ID NO:30) | | 3.979 |
| 7 | GTGACTTCAT . . . ACCTCTCTAG (SEQ ID NO:31) (SEQ ID NO:32) 978 | 0.153 | gtaagaggag . . . gctcttgcag (SEQ ID NO:33) (SEQ ID NO:34) | | 0.140 |
| 8 | GGATCACCTC . . . ACTCCGCCAT (SEQ ID NO:35) (SEQ ID NO:36) 1178 | 0.200 | gtatgagctg . . . tccattttag (SEQ ID NO:37) (SEQ ID NO:38) | | 0.283 |
| 9 | CCTCGTATCA . . . ATATATCAGC (SEQ ID NO:39) (SEQ ID NO:40) | 1.955 | | | |

GABRE was localized to chromosome Xq28 by amplification of gene fragments from somatic cell hybrids (Table 3). Most human $GABA_A$ receptor subunit genes are located in clusters on chromosomes 4, 5 and 15 (Buckle, V. J., et al., Neuron 3:647–654 (1989); Wilcox, A. S., et al., Proc. Natl. Acad. Sci. USA 89:5857–5861 (1992); Knoll, J. H., et al., Hum. Mol. Genet. 2:183–189 (1993); Russek, S. J., and Farb, D. H., Genomics 23:528–533 (1994); Hicks, A. A., et al., Genomics 20:285–288 (1994); McLean, P. J., et al., Genomics 26:580–586 (1995); Greger, V., et al., Genomics 26:258–264 (1995)). However, the Xq28 band contains a single representative of the family (GABRA3; Buckle, V. J., et al., Neuron 3:647–654 (1989)). Overlapping YAC clones that contain GABRA3 were therefore examined for the presence of GABRE. The detection of GABRE on clone IB0502, but not CH0479 (Table 3), demonstrates that GABRE is located proximal to, and within 950 kb of GABRA3 (see FIG. 3 of Rogner, U. C., et al., Hum. Mol. Genet. 3:2137–2146 (1994)). The three known subunit gene clusters consist of at least one member from each of the α, β, and γ subunit classes. It is therefore likely that these gene clusters have duplicated and dispersed as a single unit. In this respect, it is of interest to note that the human ε subunit is most similar to the γ subunit class (Davies, P. A., et al., Nature 385:820–823 (1997)). It is therefore possible that a β-like subunit is also located within the gene cluster on Xq28 (e.g. a homologue of the avian β4 subunit; Bateson, A. N., et al., J. Neurochem. 56:1437–40 (1991)). The relative orientations of subunit genes on chromosome 15 (Greger, V., et al., Genomics 26:258–264 (1995)) would predict that such a β-like subunit would be located distal to GABRA3.

TABLE 3

Physical linkage of GABRE AND GABRA3 on chromosome Xq28

| | | GABRE | | GABRA3 | |
|---|---|---|---|---|---|
| Cell line/YAC clone | X chromosome fragment | (5') | (3') | (5') | (3') |
| GM07298 | Xq | + | + | + | + |
| GM11100 | Xq26–28 | + | + | + | + |
| GM10663 | Xp–Xq27 | − | − | − | − |
| IB0502 | 950 kb of Xq28 | + | + | − | + |
| CH0479 | 410 kb of Xq28 | − | − | + | − |

Transcripts Derived from GABRE

Figure 2:
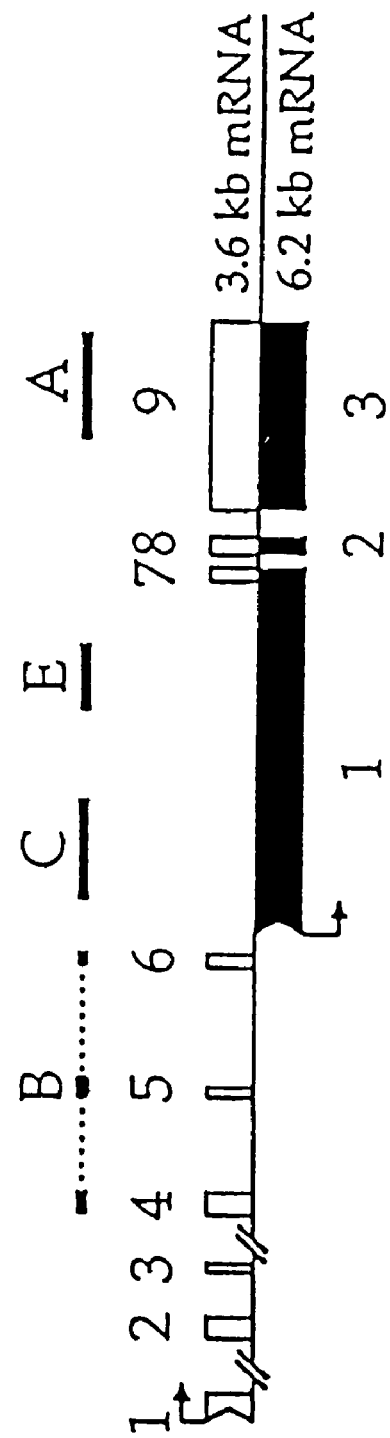
FIG. 2 shows the alternative transcripts of GABRE. The top illustration depicts exons of GABRE that are transcribed to yield alternative mRNAs. A 3.6 kb transcript is derived from 9 exons (open rectangles) and a 6.2 kb transcript is derived from 3 exons (filled rectangles). Fragments of GABRE (A, B, C, E) that were used to probe the RNA blots are also illustrated.

Sequencing of the cloned gene revealed that several expressed sequence tags are derived from intron 6 of GABRE (e.g. GenBank Accession Nos. C17228 and R07942). This information led to the isolation of a 6.2 kb cDNA clone from human testes, termed ET2. The ET2 cDNA is composed of sequences from intron 6 and exons 7–9 of GABRE (see FIG. 2).

A series of northern hybridizations were performed with $^{32}$P-labeled fragments of GABRE to determine if the ET2 and ε subunit cDNAs were derived from the same primary transcript, or if they represent distinct RNA species. Each of the cDNAs contain exon 9 of GABRE, and a fragment of this exon was used to probe blots of human mRNA from heart, brain, placenta, lung, liver, skeletal muscle, kidney, pancreas, spleen, thymus, prostate, testis, ovary, small intestine, and colon (probe A). This probe detected a transcript of 3.6 kb that is expressed abundantly in the heart. The size of this mRNA is similar to that reported for an ε subunit transcript in the subthalamic nucleus (3.2 kb; Davies, P. A., et al., *Nature* 385:820–823 (1997)). Although there have been reports of functional $GABA_A$ receptors in rat heart (Matsuyama, S., et al., *Am. J. Physiol.* 264:1057–1061 (1993); McLemore, G. L., et al., *Pharmacology* 49:342–350 (1994)), little is known of the subunit composition or pharmacological characteristics of these receptors. Probe A also hybridized with a larger transcript (6.2 kb) that was detected in a wide range of tissues. Particularly high levels of the 6.2 kb transcript are expressed in placenta, prostate, small intestine and colon. Larger species of mRNA (7.9 and 10.8 kb) that hybridize with probe A were also detected in heart, placenta and prostate.

A different pattern of hybridizing mRNAs was detected with probe B (exons 4, 5 and 6 of GABRE). In common with the previous results, probe B hybridized to transcripts of 3.6, 7.9 and 10.8 kb (heart, placenta and prostate). However, a major 6.2 kb transcript was not detected in tissues such as small intestine and colon. Although a faint band of 6.2 kb was detected in heart, placenta and prostate, its intensity (relative to the 7.9 kb and 10.8 kb transcripts) indicate that it represents an mRNA species distinct from the abundant 6.2 kb transcript which hybridized to probe A. The absence of a major 6.2 kb transcript from all tissues demonstrates that this mRNA species does not contain sequences of the three exons that are located upstream of intron 6.

In order to confirm that the major 6.2 kb transcript corresponds to the ET2 cDNA, a fragment of intron 6 was also used to probe the blots (probe C). The hybridization pattern was identical to that obtained for probe A, except for the absence of the 3.6 kb transcript in heart. The same result was obtained using a probe from a different region of intron 6 (probe E).

Together, the hybridization data indicate that only the 3.6 kb transcript is capable of encoding a full-length ε subunit protein. All of the larger mRNAs contain sequences from intron 6. The 7.9 kb and 10.8 kb mRNAs also contain sequences from upstream of intron 6, and are found only in tissues that express a 3.6 kb species. These large mRNAs may therefore represent partially spliced products of the primary ε subunit transcript. However, the major 6.2 kb transcript does not appear to contain these upstream sequences, and its size is similar to the ET2 cDNA, which starts within intron 6. It remains possible that transcription of the ET2 mRNA is initiated from upstream of intron 6. However, the hybridization data would require that the processing of such a transcript ignores the splice sites of exons 4–6 in favor of a cryptic splice site within intron 6. In view of this unusual requirement, and the size of the ET2 cDNA, it was concluded that the ET2 transcript is most likely to be initiated from within intron 6 of GABRE.

Analysis of the ET2 cDNA Sequence

The three forward reading frames of the ET2 cDNA contain stop codons within the first 60 bases. The following 3.8 kb contains only short open reading frames (ORFs). These are less than 450 bases in length, or less than 260 bases if initiated by a methionine codon. Within the entire cDNA, the longest ORF that is initiated by a methionine codon (726 bases) starts at base 3872, and includes exons 7–9 of GABRE. This ORF encodes the C-terminal half of the ε subunit protein (residues 245–506 (residues 1–242 in SEQ ID NO:2)), including the four putative transmembrane domains. However, owing to the length of sequence that precedes this ORF (3.8 kb), its translation by normal cap-dependent mechanisms is considered unlikely.

All ORFs (>300 bases) were searched against databases of known DNA and protein sequences. The entire cDNA sequence, and its six-frame translations were also searched. With the exception of the ORF that encodes the ε subunit fragment (see above), no other ORFs displayed significant homology to known proteins.

Figure 3:
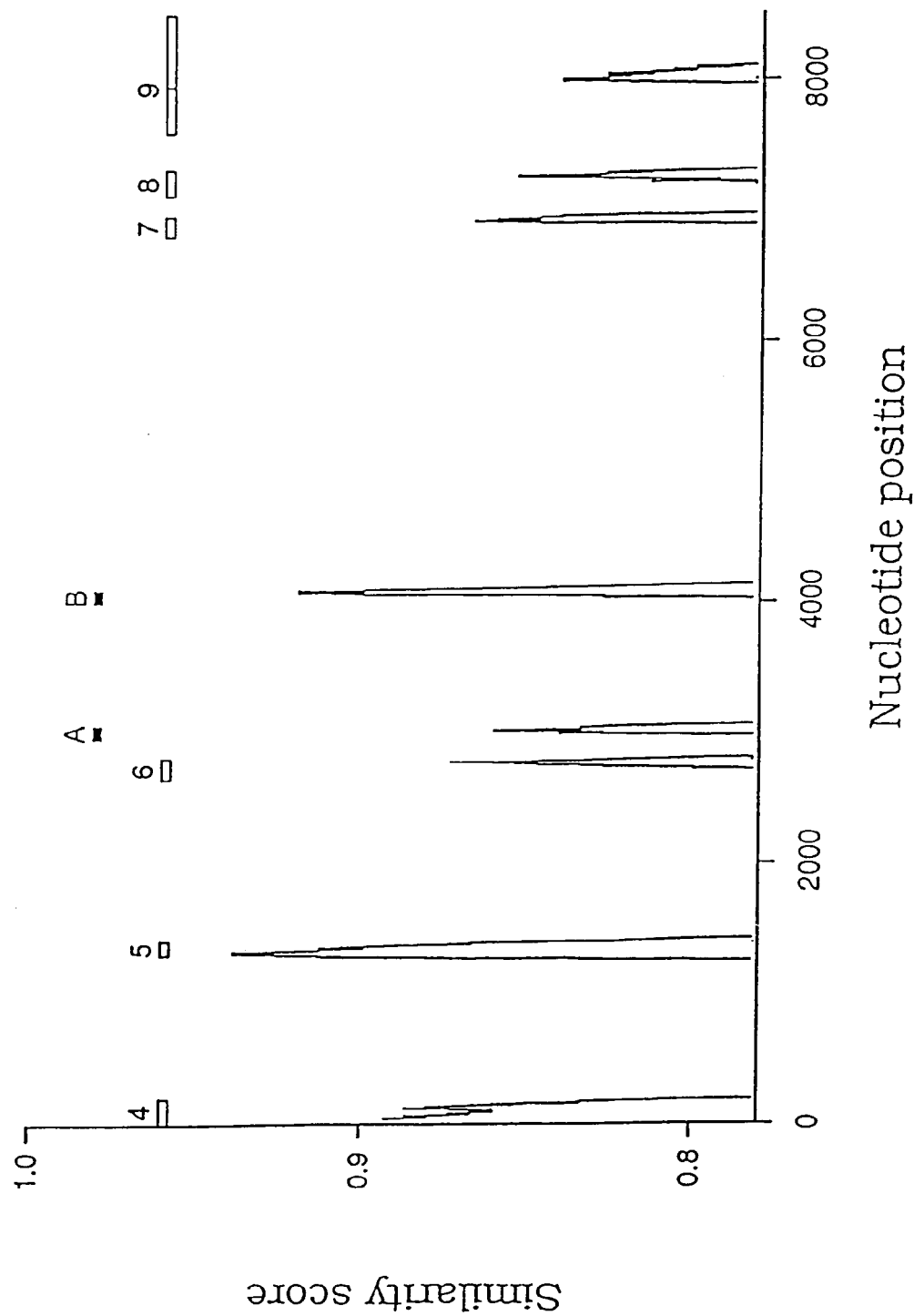
FIG. 3 shows the conservation of nucleotide sequence between the human and rat ε subunit genes. The sequence of GABRE between exons 4 and 9 was compared to the corresponding region of the homologous rat gene. The eight regions of highest similarity correspond to the six exons (numbered rectangles) and two segments of intron 6 (A and B).

It is possible that the 5' region of the ET2 cDNA encodes a short protein of novel sequence. In order to identify potential locations for such an ORF, the ET2 cDNA sequence was examined for regions that are highly conserved between human and rat. Flanking regions of GABRE were included for comparison (FIG. 3). This analysis detected eight regions of high similarity (>80% nucleotide identity) between the human and rat genomic sequences. Six of these regions correspond to exons of the ε subunit. The two other segments are contained within intron 6 of GABRE, and represent sequences of the ET2 cDNA (A and B of FIG. 3). Notably, region A is located close to the 5' end of the ET2 cDNA (nucleotides 12–108 in SEQ ID NO:1). However, this region contains stop codons in all three reading frames. The longest ORF that could be initiated from within this region encodes a peptide of only 21 amino acid residues. Region B also contains stop codons in all three reading frames. Similarly, these stop codons flank only short ORFs (<120 bases) that have no significant homology to known peptides.

Clearly, the protein-coding potential of the conserved regions is questionable at present. However, an analysis of potential mRNA folding patterns indicates that regions A and B (FIG. 3; nucleotides 12–96 and 1065–1146 in SEQ ID NO:1) may perform a distinct functional role. Both regions are predicted to adopt stable stem-loop structures. Indeed, within the 5' region of the ET2 cDNA (nucleotides 1–2000 in SEQ ID NO:1), these two folds exhibit the greatest stability of all predicted stem-loops from the region (each −36 kcal/mol). Such a strong secondary structure within region A of the transcript would be predicted to obstruct a cap-dependent scanning mechanism of translation initiation (Kozak, M., *Mol. Cell Biol* 9:5134–5142 (1989); Vega Laso, M. R., et al., *J. Biol. Chem.* 268:6453–6462 (1993)). However, a process of internal ribosome entry, that can override such a block of ribosome scanning, has been described for several eukaryotic transcripts (Oh, S. K. and Sarnow, P., *Curr. Opin. Genet. Dev.* 3:295–300 (1993); Iizuka, N., et al., *Curr. Top. Microbiol. Immunol.* 203:155–177 (1995)). If the ET2 mRNA is capable of directing internal ribosome entry, it remains possible that a truncated ε subunit could be translated from the transcript. Future studies will explore this possibility by monitoring the expression of a reporter gene after fusion within the ET2 cDNA. In addition, antisera that recognize the C-terminal of the ε subunit protein will be used to probe cell extracts after transfection of the full-length ET2 cDNA.

Example 2

Expression and Purification of ET2 and GABRE in *E. coli*

The bacterial expression vector pQE9 (PD10) is used for bacterial expression in this example. (QIAGEN, Inc., 9259 Eton Avenue, Chatsworth, Calif., 91311). pQE9 encodes ampicillin antibiotic resistance ("Amp'") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6xHis tag")) covalently linked to the amino terminus of that polypeptide.

The DNA sequence encoding the full-length ET2 protein shown in SEQ ID NO:2 is amplified essentially as described in Example 1 using PCR oligonucleotide primers which anneal to the nucleotide sequences encoding the desired portion of the ET2 protein. The DNA sequence encoding the mature GABRE protein, lacking the hydrophobic leader sequence, is amplified from the deposited cDNA clone using PCR oligonucleotide primers which anneal to the amino terminal sequences encoding the desired portion of the GABRE protein and to sequences in the deposited construct 3' to the cDNA coding sequence. In each instance, additional nucleotides containing restriction sites to facilitate cloning in the pQE9 vector are added to the 5' and 3' primer sequences, respectively. One of ordinary skill in the art would appreciate, of course, that the point in the protein coding sequence where the 5' and 3' primers begin may be varied to amplify a DNA segment encoding any desired portion of the complete ET2 or GABRE protein.

The amplified ET2 or GABRE DNA fragment and the vector pQE9 are digested with suitable restriction enzymes and the digested DNAs are then ligated together. Insertion of the ET2 or GABRE DNA into the restricted pQE9 vector places the protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan"), is used in carrying out the illustrative example described herein. This strain, which is only one of many that are suitable for expressing either the ET2 or GABRE protein, is available commercially from QIAGEN, Inc., supra Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the ET2 or GABRE is loaded onto a nickel-nitrilo-tri-acetic acid ("NiNTA") affinity resin column (available from QIAGEN, Inc., supra). Proteins with a 6xHis tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the ET2 or GABRE is eluted with 6 M guanidine-HCl, pH5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM imidazole. Imidazole is removed by a final dialyzing step against PBS or 50 mM sodium acetate pH6 buffer plus 200 mM NaCl. The purified protein is stored at 4° C. or frozen at −80° C.

Example 3

Cloning and Expression of ET2 and GABRE Protein in a Baculovirus Expression System In this illustrative example, the plasmid shuttle vector pA2 GP is used to insert the cloned DNA encoding the ET2 protein into a baculovirus to express the full-length ET2, using a baculovirus leader. Further, the plasmid shuttle vector pA2 is used to insert the cloned DNA encoding the complete protein, including its naturally associated secretary signal (leader) sequence, into a baculovirus to express the mature GABRE protein. In each case, standard methods described in Summers et al., *A Manual of Methods for Baculovirus Vectors and Insect Cell Culture Procedures*, Texas Agricultural Experimental Station Bulletin No. 1555 (1987) are employed.

The pA2 GP and pA2 expression vectors contain the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the full-length ET2 protein shown in SEQ ID NO:2, is amplified essentially as described in Example 1 using PCR oligonucleotide primers corresponding, for example, to the 5' and 3' sequences of the ET2 coding sequences. The DNA sequence encoding the full-length GABRE protein, including the hydrophobic leader sequence, is amplified from the deposited cDNA clone using PCR oligonucleotide primers which anneal to the amino terminal sequences encoding the GABRE protein and to sequences in the deposited construct 3' to the cDNA coding sequence. In each instance, additional nucleotides containing restriction sites to facilitate cloning in the pQE9 vector are added to the 5' and 3' primer sequences, respectively. One of ordinary skill in the art would appreciate, of course, that the point in the protein coding sequence where the 5' and 3' primers begin may be varied to amplify a DNA segment encoding any desired portion of the complete ET2 or GABRE protein.

The amplified fragment is isolated from a 1% agarose gel using a commercially available kit ("Geneclean," BIO 101 Inc., La Jolla, Calif.). The fragment then is digested with suitable restriction enzymes and again is purified on a 1% agarose gel. This fragment is designated herein "F1".

The plasmid is also digested with the restriction enzymes suitable for the generation of "sticky" ends which will anneal with those of the amplified ET2 or GABRE coding sequence. Optionally, the plasmid can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein V1.

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human ET2 or GABRE gene using the PCR method, in which one of the primers that is used to amplify the gene and the second primer is from well within the vector so that only those bacterial colonies containing the ET2 or GABRE gene fragment will show amplification of the DNA. The sequence of the cloned fragment is confirmed by DNA sequencing. These plasmids are designated herein pBacET2 and pBacGABRE.

Five µg of the plasmid pBacET2 or pBacGABRE is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). One µg of BaculoGold™ virus DNA and 5 µg of the plasmid pBacET2 or pBacGABRE are mixed in a sterile well of a microtiter plate containing 50 µl of serum-free Grace's medium (Life Technologies Inc., Rockville, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Rockville, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Rockville, Md., page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant viruses are called V-ET2 and V-GABRE.

To verify the expression of the ET2 or GABRE gene, Sf9 cells are grown in Grace's medium supplemented with 10% heat inactivated FBS. The cells are infected with the recombinant baculovirus V-ET2 or V-GABRE at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the full-length protein and thus the cleavage point and length of the secretory signal peptide.

Example 4

Cloning and Expression of ET2 and GABRE in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human HeLa 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem. J.* 22 7:277–279 (1991); Bebbington et al., *Bio/Technology* 10: 169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molec. Cell. Biol.* 5:438–447 (1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 4(a)

Cloning and Expression in COS Cells

The expression plasmids, pET2-HA and pGABRE-HA, are made by cloning a cDNA encoding ET2 or GABRE into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767–778 (1984). The fusion of the HA tag to the target protein allows easy detection and recovery of the recombinant protein with an antibody that recognizes the HA epitope. The pcDNAIII vector contains, in addition, the selectable neomycin marker.

A DNA fragment encoding the ET2 or GABRE is cloned into the polylinker region of the vector so that recombinant protein expression is directed by the CMV promoter. The plasmid construction strategy is as follows. ET2 cDNA is amplified essentially as described in Example 1 using 5' and 3' primers which contain convenient restriction sites. The DNA sequence encoding the full-length GABRE protein, including the hydrophobic leader sequence, is amplified from the deposited cDNA clone using PCR oligonucleotide primers which anneal to the amino terminal sequences encoding the GABRE protein and to sequences in the deposited construct 3' to the cDNA coding sequence.

The PCR amplified DNA fragment and the vector, pcDNAI/Amp, are digested with suitable restriction enzymes and then ligated. The ligation mixture is transformed into *E. coli* strain SURE (available from Stratagene Cloning Systems, 11099 North Torrey Pines Road, La Jolla, Calif. 92037), and the—transformed culture is plated on ampicillin media plates which then are incubated to allow growth of ampicillin resistant colonies. Plasmid DNA is isolated from resistant colonies and examined by restriction analysis or other means for the presence of the ET2 or GABRE-encoding fragment.

For expression of recombinant ET2 or GABRE, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of ET2 or GABRE by the vector.

Expression of the ET2-HA and GABRE-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP- 40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 4(b)

Cloning and Expression in CHO Cells

The vector pC4 is used for the expression of ET2 and GABRE proteins. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate reductase activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the ET2 or GABRE in a regulated way in mammalian cells (Gossen, M., & Bujard, H. 1992, Proc. Natl. Acad. Sci. USA 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes suitable restriction enzymes and then dephosphorylated using calf intestinal phosphatase by procedures known in the art. The vector is then isolated from a 1% agarose gel.

The DNA sequence encoding the complete ET2 protein is amplified essentially as described in Example 1 using PCR oligonucleotide primers corresponding to the 5' and 3' sequences of the gene sequences which are to be cloned. The DNA sequence encoding the full-length GABRE protein, including the hydrophobic leader sequence, is amplified from the deposited cDNA clone using PCR oligonucleotide primers which anneal to the amino terminal sequences encoding the GABRE protein and to sequences in the deposited construct 3' to the cDNA coding sequence. In each instance, the amplified fragment is digested with the endonucleases restriction enzymes which produce suitable "sticky" ends for ligation into the pC4 plasmid and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 5

Tissue Distribution of ET2 and GABRE mRNA Expression

Northern blot analysis is carried out to examine ET2 and GABRE gene expression in human tissues, using methods described by, among others, Sambrook et al., cited above. A cDNA probe containing the entire nucleotide sequence of the ET2 protein (SEQ ID NO:1) or the GABRE protein (SEQ ID NO:41) is labeled with $^{32}P$ using the rediprime® DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for ET2 or GABRE mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Example 6

Insensitivity to Anaesthetic Agents Conferred by a Class of $GABA_A$ Receptor Subunit At least thirteen different subtypes of $GABA_A$ receptor subunits have been identified in mammals and categorized into four structural classes (α1–6, β1–3, γ1–3 and δ). These subunits are thought to assemble in different pentameric complexes, with most functional receptors containing α/β/γ or α/β/δ subunit combinations (Whiting, P. et al., *Int. Rev. Neurobiol.* 38:95–138 (1995)).

An expressed sequence tag (EST) which encodes a new class of subunit was identified by searching an EST database with a peptide consensus sequence of known family members. Using the sequence of this EST, flanking cDNA sequences were amplified from a hippocampal cDNA library by anchored polymerase chain reaction (PCR). The longest contiguous cDNA identified by this method is 3.1 kilobases in length and contains a large open reading frame which encodes a polypeptide of 506 amino-acid residues (FIG. 4 (SEQ ID NO:41)). This amino-acid sequence (SEQ ID NO:42) is most closely related to $GABA_A$ receptor γ-subunits (38–43% amino-acid identity) and α-subunits (28–30%) and has less similarity to other GABA and glycine receptor subunits (<25%). The maximum levels of sequence identity are similar to those found between the different classes of $GABA_A$ receptor subunits (Whiting, P. et al., *Int. Rev. Neurobiol.* 38:95–138 (1995)), and justified its categorization in a distinct subunit class (ε).

Northern analyses were used to examine the expression of E-subunit mRNA in various tissues. Two species of RNA (2.8 and 3.2 kb) were readily detectable in a number of brain regions using probes derived from either the 3'- or 5'-ends of the ε-subunit cDNA. While these transcripts were barely detectable in samples of whole brain, they were relatively enriched in amygdala and thalamus, and were particularly abundant in the subthalamic nucleus. The subthalamic nucleus is known to receive major GABA-mediated inputs, with particularly dense projections arising from the globus pallidus (Bell, K. et al., *Synapse* 20:10–18 (1995)). Notably, the relatively low levels of γ- and δ-subunit transcripts in rat subthalamic nucleus (Wisden, W. et al., *J. Neurosci.* 12:1040–1062 (1992)) are consistent with expression of alternative receptor subunits in this tissue.

The biophysical and pharmacological properties conferred to $GABA_A$ receptors by the ε-subunit were examined after transient expression in HEK-293 cells. Cells transfected with only the ε-subunit cDNA did not express binding sites of the $GABA_A$ receptor ligands [$^3H$]muscimol or [$^{35}S$] t-butyl bicyclophosphorothionate (TBPS). These cells also failed to exhibit chloride currents in response to GABA or glycine (each 100 μM). The ε-subunit is therefore unlike the ρ class of receptor subunits (Whiting, P. et al., *Int. Rev. Neurobiol.* 38:95–138 (1995)), or the α class of glycine-receptor subunits Schmieden, V. et al., *EMBO J.* 11:2025–2032 (1992)), which can each assemble homomeric chloride channels that are gated by these ligands. When cells were co-transfected with cDNAs encoding the ε-subunit, and either an α-subunit (α1, α2 or β6) or a β-subunit (β1 or β3), there was also a failure to detect expression of any ligand-binding activities. Therefore the ε-subunit does not behave like a typical $GABA_A$ receptor α- or β-subunit (Whiting, P. et al., *Int. Rev. Neurobiol.* 38:95–138 (1995)). As expected, transfection of cells with a combination of α-, β- and ε-subunits resulted in the expression of GABA-activated currents (FIGS. 5A–5C) and [$^{35}$S] TBPS binding sites (FIGS. 6A–6D). However, the transfected cell membranes did not bind either [$^3$H]flunitrazepam or [$^3$H]flumazenil. Therefore the ε-subunit is also unlike the γ-class of subunits, which confers a sensitivity to benzodiazepines when expressed with α- and β-subunits (Whiting, P. et al., *Int. Rev. Neurobiol.* 38:95–138 (1995)). The remaining subunit class, δ, has no unique pharmacological features to compare, but can be distinguished from the ε-subunit by its sensitivity to barbiturates (Saxena, N. C. and Macdonald, R. L., *J. Neurosci.* 14: 7077–7086 (1994) and see below).

Figure 5A:
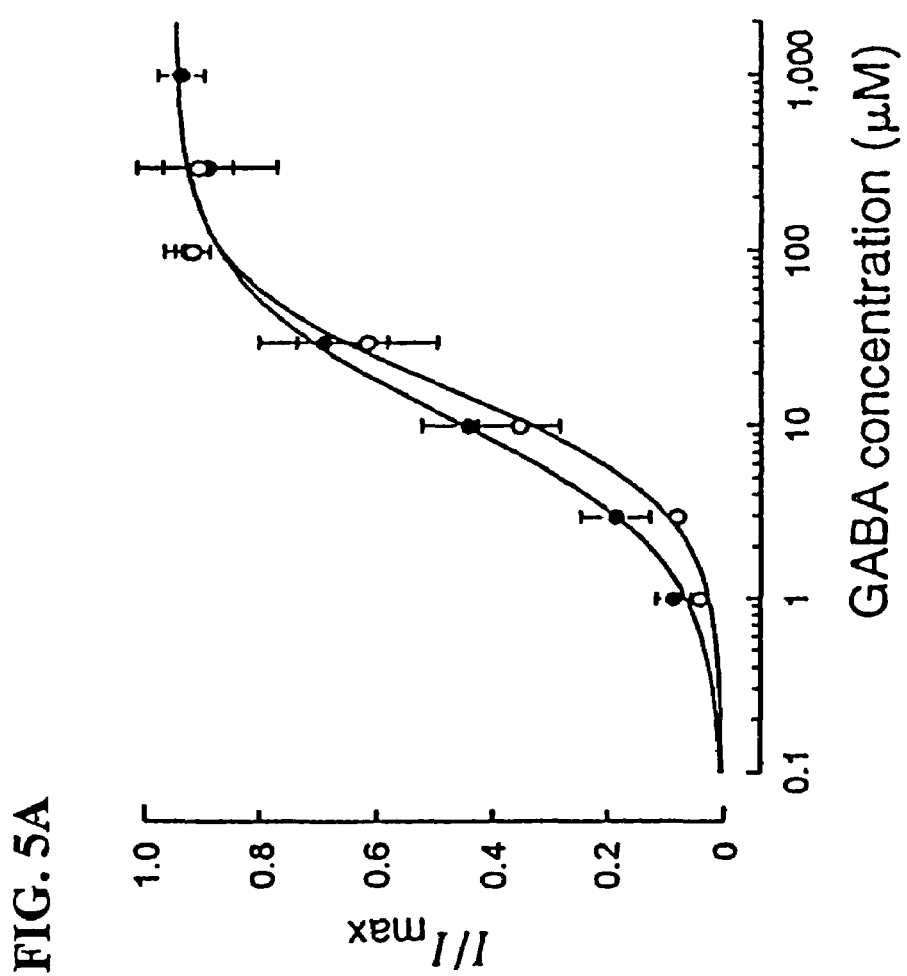
FIGS. 5A–5C show the effects of the ε-subunit on activation of receptors by GABA.
Figure 5B:
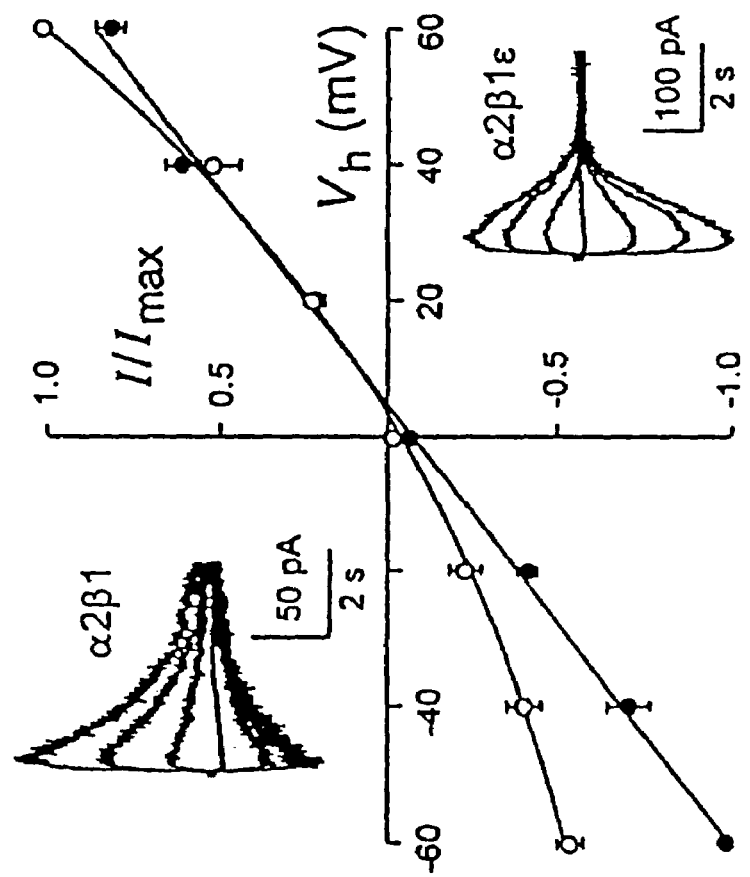
Figure 5C:
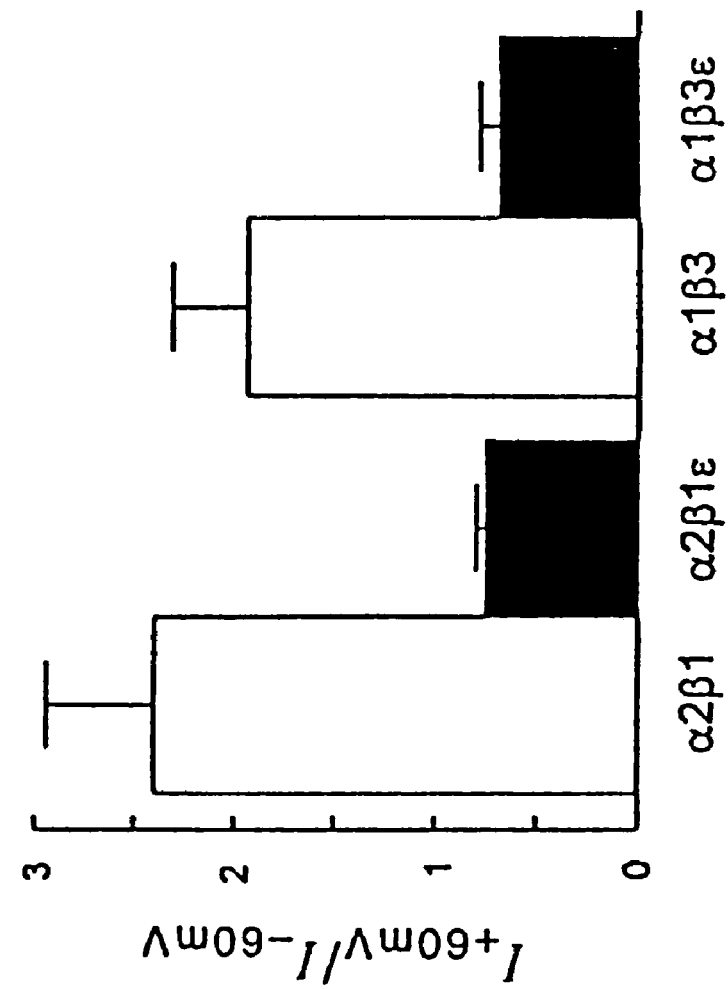

There was little difference between the concentration-response relationships for GABA-activated chloride currents recorded from cells transfected with α2/β1 or α2/β1/ε cDNAs (FIG. 5A). The selective $GABA_A$ receptor inhibitors picrotoxin (10 μM) and bicuculline (10 μM) blocked currents mediated by the α2/β1/ε subunit combination by 82.5±7.4% (N=3) and 73.6±9.3% (N=4), respectively. However, a comparison of current-voltage relationships showed that ε-subunits can assemble with α- and β-subunits and confer new biophysical properties. Previous studies have shown that native and recombinant $GABA_A$ receptors exhibit a pronounced outward rectification (Verdoom, T. et al., *Neuron.* 4:919–928 (1992); Davies, P. et al., *Br. J. Pharmacol.* 120:899–909 (1997); Gray, R. and Johnston, D., *J. Neurophysiol.* 54:134–142 (1985); and Segal, M. et al., *J. Neurophysiol.* 51:500–515 (1984)). Here this was confined with cells expressing α2/β1 or α1/β3 subunits, which displayed larger GABA-evoked currents when clamped at positive potentials than at the corresponding negative values (FIG. 5B and FIG. 5C). In contrast, inclusion of the ε-subunit with either subunit combination yielded currents which exhibit a linear relationship to voltage (FIG. 5B). The cause of outward rectification at $GABA_A$ receptors is controversial (Gray, R. and Johnston, D., *J. Neurophysiol.* 54:134–142 (1985); Segal, M. et al., *J. Neurophysiol.* 51:500–515 (1984); Bormann, J. et al., *J. Physiol.* (Lond.) 385:243–286 (1987); and Gage, P. W. and Chung, S. H., *Proc. R. Soc. Lond.* B255:167–172 (1994)), and any of the proposed mechanisms could be influenced by inclusion of the ε-subunit. However, the ε-subunit displays an unusually high density of basic residues close to the M3 segment (residues 376–401) which may affect rectification properties by sequestering chloride ions near the intracellular face of the ion channel.

Figure 6A:
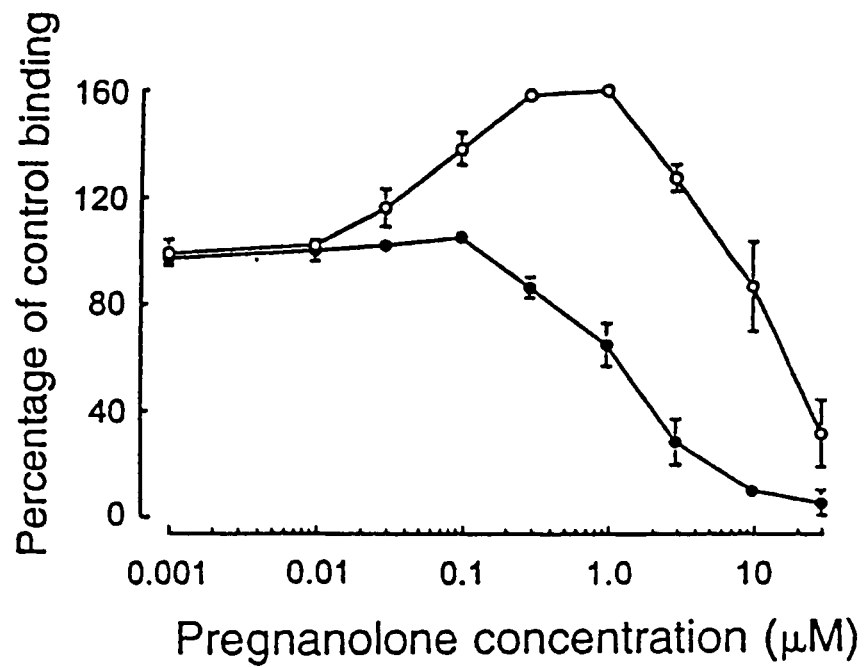
FIGS. 6A–6D show the effects of the ε subunit on the modulation of $GABA_A$ receptors by anaesthetic agents.
Figure 6B:
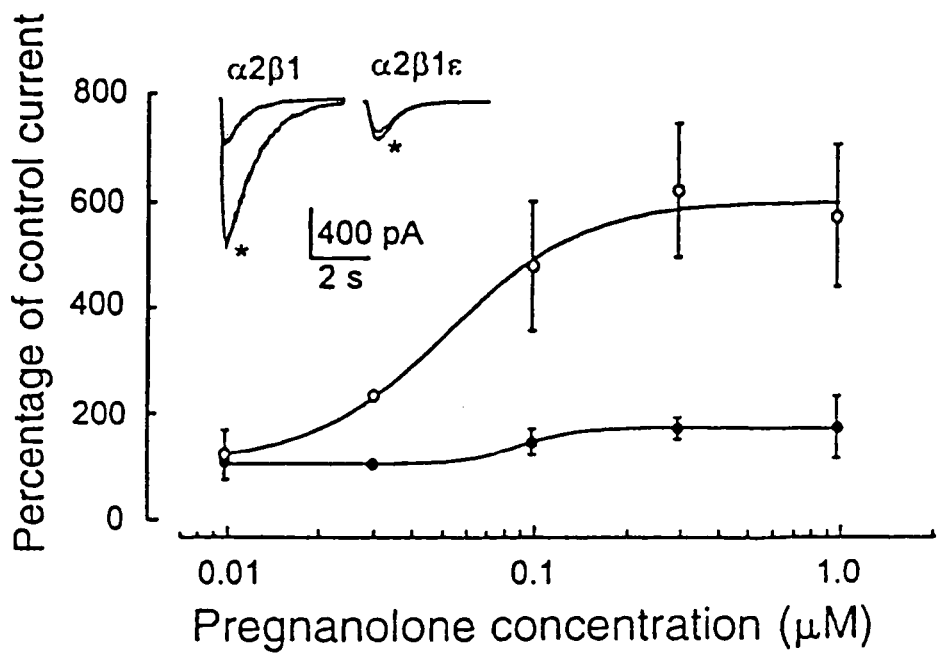

Having shown that ε-subunits can assemble with other $GABA_A$ receptor subunits, its effects on receptor pharmacology was examined. Unexpectedly, the presence of the ε-subunit had a pronounced effect on the sensitivity of $GABA_A$ receptors to intravenous anaesthetic agents. This was shown by both radioligand binding and by measurement of GABA-evoked currents (FIGS. 6A–6D). First, in common with studies on other α/β subunit combinations (Davies, P. et al., *Br. J. Pharmacol.* 120:899–909 (1997) and Korpi, E. R. and Luddens, H., *Mol. Pharmacol.* 44:87–92 (1993)), the anaesthetic steroid, 5α-pregnan-3α-ol-20-one, was found to have a biphasic effect on [$^{35}$S]TBPS binding to cells expressing α2/β1 subunits. In contrast, there was no stimulatory phase to the dose-response curve when using the α2/β1/ε subunit combination (FIG. 6A). The functional correlate of this assay examined the effect of pregnanolone (10 nM to 1 PM) on submaximal GABA-activated currents recorded from cells expressing α2/β1 or α2/β1/ε-subunit combinations (FIG. 6B). In the absence of the ε-subunit, currents were potentiated by up to 521%, with a half-maximal effective concentration ($EC_{50}$) value of 53 nM. In contrast, currents recorded from the α2/β1/ε subunit combination were relatively insensitive to the steroid. No significant effects were observed at concentrations up to 100 nM pregnanolone, and only minor effects (up to 73% potentiation) were detected at high concentrations of the steroid (FIG. 6B).

Figure 6C:
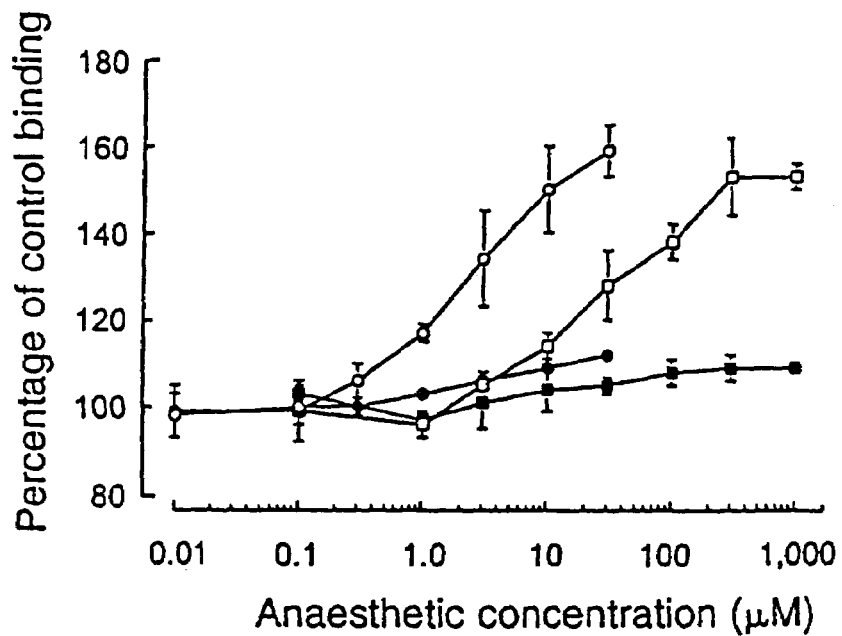
Figure 6D:
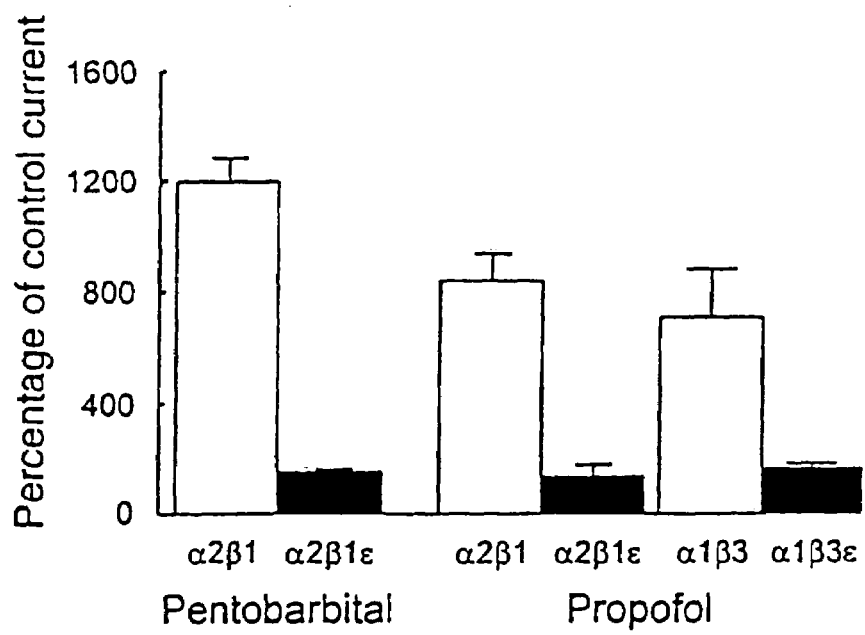

This effect of the ε-subunit was examined further using different subunit combinations and additional anaesthetic agents. The ability of anaesthetic agents to stimulate [$^3$H] muscimol binding to cell membranes is a reliable indicator of their ability to stimulate GABA-evoked currents recorded from intact cells (Peters, J. et al., *Br. J. Pharmacol.* 94:1257–1269 (1988)). After transfection with α1/β3 subunits, [$^3$H]muscimol binding to cell membranes was stimulated by up to 60% in the presence of pregnanolone or the anaesthetic agent pentobarbital. However, when the ε-subunit was expressed with this combination, the maximal stimulation dropped to below 15% (FIG. 6C). The dose-response curves for a third anaesthetic agent, propofol (2,6-diisopropylphenol), were similar to those of pentobarbital (data not shown). Consistent with the effect on ligand binding, inclusion of the ε-subunit with different α/β subunit combinations blocked the ability of pentobarbital (100 μM) and propofol (3 μM) to enhance GABA-evoked currents (FIG. 6D).

High concentrations of anaesthetic agents can activate $GABA_A$ receptors in the absence of GABA (Whiting, P. et al., *Int. Rev. Neurobiol.* 38:95–138 (1995)). Notably, cells expressing α/β/ε subunit combinations retained their sensitivity to this direct activation. Pregnanolone (10 μM), propofol (100 μM) and pentobarbital (1 mM) each evoked picrotoxin-sensitive currents recorded from cells expressing α2/β1/ε or α1/β3/ε cDNAs (0.2–2.1 nA, N=4–6). The loss of sensitivity to the potentiating effects, but not the activating effects, of intravenous anaesthetic agents supports the position that the two responses are mediated by different anaesthetic binding sites on the receptor complex (Sanna E. et al., *J. Pharmacol. Exp. Ther.* 274:353–360 (1995)). The δ subunit has been reported to confer analogous properties with respect to anaesthetic steroids (Zhu, W. et al., *J. Neurosci.* 16:6648–6656 (1996)) but not barbiturates (Saxena, N. C. and Macdonald, R. L., *J. Neurosci.* 14: 7077–7086 (1994)). Future use of δ- and δ-subunit fragments for chimaeric subunit construction may provide insights to the structural basis of different anaesthetic actions at $GABA_A$ receptors.

It remains possible that the ε-subunit can confer additional pharmacological properties to $GABA_A$ receptors that have yet to be uncovered. In view of its abundant expression in the subthalamic nucleus, identification of these properties could have important implications for the treatment of a variety of movement disorders, including Parkinson's disease (Bergman, H. et al., *Science* 249:1436–1438 (1990) and Goetz, C. G. and Diederich, N. J., *Nature. Med.* 2:510–514

(1996)). Its restricted expression pattern in the human brain also provides an opportunity for relatively selective manipulation of this important nucleus of the basal ganglia.

Methods

Isolation of the ε-subunit cDNA. Searches of the database dbEST (http://www.ncbi.nlm.nih.gov/dbEST/index.html) were made using the TBLASTN algorithm. The query sequence used was a consensus polypeptide containing amino-acid residues which are invariant between all known mammalian $GABA_A$ receptor subunits (FIG. 4). Oligonucleotide primers were designed from an EST sequence (GenBank accession No. R07883) to amplify 5' and 3' flanking sequences from cDNA libraries (Adams, M. et al., *Nature* (suppl.) 377:3–174 (1995)) by anchored PCR. Amplification at 95° C. for 45 seconds, 60° C. for 60 seconds and 72° C. for 2 minutes was performed for 35 cycles using the XL-PCR system (Perkin Elmer). Reaction products were purified from agarose gels and sequenced directly. The ε-subunit open reading frame was amplified from a hippocampal cDNA library as described above using primers containing nucleotides 11–34 (sense) and 1,569–1,592 (antisense) of the e-subunit cDNA sequence (GenBank Accession No. U66661 (SEQ ID NO:41)). The reaction products were ligated into pCDM8 (Invitrogen), and the resulting clones were sequenced to ensure that no mutations had been introduced.

Northern blot analysis. Samples of approximately 2 μg poly(A)+ RNA (Clontech) were electrophoresed on a 1.2% formaldehyde agarose gel, transferred to a nylon membrane and hybridized with a $^{32}$P-labeled fragment of the 3'-untranslated ε-subunit cDNA (nucleotides 1,939–2,945 in SEQ ID NO:41). The blot was washed at 60° C. in 0.1×SSC, 0.1% SDS before exposure and then stripped of probe by boiling in 0.5% SDS, and rehybridized with a $^{32}$P-labeled fragment from the 5' end of the ε-subunit cDNA (nucleotides 19–347 in SEQ ID NO:41). Finally, the same blot was stripped and reprobed with a $^{32}$P-labeled fragment of the human GAPD cDNA (Tokunaga, K. et al., *Cancer Res.* 47:5616–5619 (1987)) (nucleotides 789–1,140 in SEQ ID NO:41).

Transient transfection of subunit cDNAs. Transfection of human embryonic kidney cells (HEK-293) with subunit cDNAs was performed with a calcium phosphate-DNA precipitate in HEPES buffer. After incubation with the precipitate for 24 hours, the cells were washed and cultured for a further 48–72 hours before use. The subunit cDNAs used for transfection were: human α2 and β1, cloned in pCIS2; rat α1, rat α6, rat β1, human β3 and human ε, cloned in pCDM8.

Radioligand binding assays. Transfected cells were washed twice with phosphate-buffered saline and collected by scraping into an ice-cold solution containing 10 mM Tris-HCl, 1 mM EDTA, 100 mM NaCl, pH 7.5 (TEN). The cells were collected by centrifugation (5,000 g, 10 min), hand homogenized in TEN, and a crude membrane fraction was obtained by centrifugation (30,000 g, 30 min). The membrane pellet was washed twice with TEN, and then resuspended in TEN at a protein concentration of ~3 mg ml$^{-1}$. The binding of [$^{35}$S]TBPS (20 nM; 88.7 Ci mmol$^{-1}$; NEN) to membranes (50–100 ng protein) was assayed by filtration after incubation for 120 min at 25° C. in 100 μl of a solution containing 20 mM Tris-HCl, 1 M NaCl, pH 7.5. Nonspecific binding was determined in the presence of picrotoxin (100 μM), and was equal to the binding of mock-transfected cell membranes (<0.03 pmol per mg protein). The binding of [$^3$H]muscimol (30 nM; 19.5 Ci mmol$^{-1}$; NEN) was assayed after incubation of membranes for 60 min at 0° C. in 100 μl of TEN. Nonspecific binding was determined in the presence of GABA (1 mM). The binding of [$^3$H]flunitrazepam and [$^3$H]flumazenil (each 1–50 nM) was assayed essentially as previously described (Buller, A. et al., *Mol. Pharmacol.* 46:858–865 (1994)). All binding data were derived from the mean ±s.d. of three independent transfections.

Electrophysiology. Cells were superfused (5 ml min$^{-1}$) with a solution of 140 mM NaCl, 4.7 mM KCl, 1.2 mM MgCl$_2$, 2.5 mM CaCl$_2$, 11 mM glucose, and 10 mM HEPES, pH 7.4 during whole-cell recordings. The electrode solution contained 140 mM KCl, 2.0 mM MgCl$_2$, 11 mM EGTA, and 10 mM HEPES, pH 7.4. The electrode solution was supplemented with 100 μM ATP to prevent current rundown in recordings from cells expressing α2/β1 and α2/β1/ε. When examining their agonist action, GABA, glycine and anaesthetics were applied locally, by pressure (70 kPa) ejection from micropipettes situated 50 μm from the cell. For modulation experiments, in which anaesthetics, bicuculline methiodide and picrotoxin were bath applied, GABA (100 μM) was ejected for brief durations (5–30 ms) that activated approximately 10% of maximum current amplitude. GABA was applied for 1 second from low-resistance pipettes for concentration-response experiments (Adodra, S. and Hales, T. G., *Br. J. Pharmacol.* 115:953–960 (1995)). Currents were filtered (1 kHz) and recorded at −60 mV (unless otherwise stated) using an Axopatch 200 A amplifier. Data were simultaneously digitized for storage on VCR tapes and the hard drive of an IBM PC. Currents were analyzed and reproduced using pCLAMP software (Axon). All electrophysiological data are mean±s.e.m.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide encoding a polypeptide comprising an amino acid sequence at least 95% identical to amino acids 1 to 488 of SEQ ID NO:42;
    wherein % identity is determined with parameters that calculate % identity over the full length of amino acids 1 to 488 of SEQ ID NO:42 and that allow gaps of up to 5% of the total number of residues in amino acids 1 to 488 of SEQ ID NO:42;
    wherein said polypeptide forms a GABAA receptor complex with α- and β-GABAA receptor subunits; and
    wherein said complex produces GABA-activated chloride currents.

2. The isolated polynucleotide of claim 1, comprising a nucleotide sequence encoding amino acids 1 to 488 of SEQ ID NO:42.

3. The isolated polynucleotide of claim 2, comprising nucleotides 95 to 1558 of SEQ ID NO:41.

4. An isolated polynucleotide comprising a nucleotide sequence encoding a polypeptide comprising an amino acid sequence at least 95% identical to amino acids −17 to 488 of SEQ ID NO:42;

wherein % identity is determined with parameters that calculate % identity over the full length of amino acids −17 to 488 of SEQ ID NO:42 and that allow gaps of up to 5% of the total number of residues in amino acids −17 to 488 of SEQ ID NO:42;

wherein said polypeptide forms a GABAA receptor complex with α- and β-GABAA receptor subunits; and wherein said complex produces GABA-activated chloride currents.

5. The isolated polynucleotide of claim 4, comprising a nucleotide sequence encoding amino acids −17 to 488 of SEQ ID NO:42.

6. The isolated polynucleotide of claim 4, comprising nucleotides 44 to 1558 of SEQ ID NO:41.

7. An isolated polynucleotide comprising a nucleotide sequence encoding a polypeptide comprising an amino acid sequence at least 95% identical to amino acids −18 to 488 of SEQ ID NO:42;

wherein % identity is determined with parameters that calculate % identity over the full length of amino acids −18 to 488 of SEQ ID NO:42 and that allow gaps of up to 5% of the total number of residues in amino acids −18 to 488 of SEQ ID NO:42;

wherein said polypeptide forms a GABAA receptor complex with α- and β-GABAA receptor subunits; and wherein said complex produces GABA-activated chloride currents.

8. The isolated polynucleotide of claim 7, comprising a nucleotide sequence encoding amino acids −18 to 488 of SEQ ID NO:42.

9. The isolated polynucleotide of claim 8, comprising nucleotides 41 to 1558 of SEQ ID NO:41.

10. The isolated polynucleotide of claim 1, further comprising a heterologous polynucleotide.

11. The isolated polynucleotide of claim 10, wherein said heterologous polynucleotide encodes a heterologous polypeptide.

12. A method of producing a vector that comprises inserting the isolated polynucleotide of claim 1 into a vector.

13. A vector comprising the isolated polynucleotide of claim 1.

14. The vector of claim 13, wherein said polynucleotide is operably associated with a heterologous regulatory sequence.

15. An isolated host cell comprising the isolated polynucleotide of claim 1.

16. The host cell of claim 15, wherein said isolated polynucleotide is operably associated with a heterologous regulatory sequence.

17. A method of producing a polypeptide that comprises culturing the host cell of claim 16 under conditions such that said polypeptide is expressed, and recovering said polypeptide.

18. An isolated polynucleotide encoding a polypeptide comprising an amino acid sequence at least 95% identical to the complete amino acid sequence encoded by the cDNA clone in ATCC Deposit No. 209642;

wherein % identity is determined with parameters that calculate % identity over the full length of the complete amino acid sequence encoded by the cDNA clone in ATCC Deposit No. 209642 and that allow gaps of up to 5% of the total number of residues of the complete amino acid sequence encoded by the cDNA clone in ATCC Deposit No. 209642;

wherein said polypeptide forms a GABAA receptor complex with α- and β-GABAA receptor subunits; and wherein said complex produces GABA-activated chloride currents.

19. The isolated polynucleotide of claim 18, wherein the polypeptide comprises the complete amino acid sequence encoded by the cDNA clone in ATCC Deposit No. 209642.

20. The isolated polynucleotide of claim 18, further comprising a heterologous polynucleotide.

21. The isolated polynucleotide of claim 20, wherein said heterologous polynucleotide encodes a heterologous polypeptide.

22. A method of producing a vector that comprises inserting the isolated polynucleotide of claim 18 into a vector.

23. A vector comprising the isolated polynucleotide of claim 18.

24. The vector of claim 23, wherein said polynucleotide is operably associated with a heterologous regulatory sequence.

25. An isolated host cell comprising the isolated polynucleotide of claim 18.

26. The host cell of claim 25, wherein said isolated polynucleotide is operably associated with a heterologous regulatory sequence.

27. A method of producing a polypeptide that comprises culturing the host cell of claim 26 under conditions such that said polypeptide is expressed, and recovering said polypeptide.

28. An isolated polynucleotide comprising 60 contiguous nucleotides of the coding region of SEQ ID NO:41.

29. The isolated polynucleotide of claim 28, wherein said sequence comprises 70 contiguous nucleotides of SEQ ID NO:41.

30. The isolated polynucleotide of claim 29, wherein said sequence comprises 100 contiguous nucleotides of SEQ ID NO:41.

31. The isolated polynucleotide of claim 30, wherein said sequence comprises 200 contiguous nucleotides of SEQ ID NO:41.

32. The isolated polynucleotide of claim 28, further comprising a heterologous polynucleotide.

33. The isolated polynucleotide of claim 32, wherein said heterologous polynucleotide encodes a heterologous polypeptide.

34. A method of producing a vector that comprises inserting the isolated polynucleotide of claim 28 into a vector.

35. A vector comprising the isolated polynucleotide of claim 28.

36. The vector of claim 35, wherein said polynucleotide is operably associated with a heterologous regulatory sequence.

37. An isolated host cell comprising the isolated polynucleotide of claim 28.

38. The host cell of claim 37, wherein said isolated polynucleotide is operably associated with a heterologous regulatory sequence.

39. A method of producing a polypeptide that comprises culturing the host cell of claim 38 under conditions such that said polypeptide is expressed, and recovering said polypeptide.

* * * * *

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
    (A) LENGTH: 6146 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 3872..4597

(xi) SEQUENCE DESCRIPTION: SEQ ID NO:1:

```
GTCTTATAAT TGCTAAGCAC TTACAACTGT TTGCAGAGGA AACTGAGACT TTGTAACTAT      60

GTCTCAGTCT CATCTGCAAA GAAGTAAGTG CTTTGCCAAG CTCCTTGAGA GGTTAGGTAA     120

GTAGATAAAG TTCTGCTGCT GTCGGAATGT GCAGCTGGCT TTTTCATGCA GACCCTTCAG     180

TTTCGAGGTT ACAACTCTGA CCTCTTTGGA TGACTTTGGG GAATGGAGCT CGTGTGAGTT     240

CTCCATACCC AGAACCAATC CAGTCTGGTT GAATGGGAAG CAAAGTCCAT TGTAGTGGGA     300

GGTGGAGGCT AGAGTTCTAA TGTCAGCTAG TTTAAGGCTG GGAAAGTCTG GAGGAAGTTA     360

CAGCAGCTAC ACTGGCTGCT GCATTGACAT TTATCTTAAA GGAACAAGTC TGAAAAGCAC     420

AGATTCTTAT CAAAGGCTTC ATGGTGGATT CCACATAGAC ATAGTGGCCA CTGGTTTTCT     480

GACCTTTTCT CTGACAAAGA CTAAAGGGGA AGGTCCTGGG TATCTTACAC TTCAGCTCCC     540

AATTAGATGT GAGCACCTTC ACTTATGTTC CTAGGTGACC TGAATGAGGA GCCAAGGGAC     600

CTCCCCAGGG TAGCTCCCAG AGCAACCCTG GAAACACTCT TCACACATCC TGACCAAGTT     660

CAGGGCAGTG AAGGCACTGC CCTCATCGTT TCCAGAATGT GGATGGAGCC AGTCACCCAA     720

CCAGCCATTT GTCGTGAGAG GCATCTTGTT CTGCTACCAT GTGACTAGGC AGAAAATCTG     780

CTTTTGTTTC ATTTATTGAG TCAGTCTCTG GATGAGGGAA AGCTCATGCT CATGTGGCTA     840

GAGCTTTGCT TGCACAGTAT TAGGCAGGGG CAGAGGGCTG GGCTACCTTA AAAATACTTG     900

CCCTTTTTCT TGGGGACTCT GGGGAAGCGG TTTTACTACC TTTGACTTGG GAGCCTTGCT     960

CTTCTGCCAG CTAACCATGG GCCTGCCTCT TGGTTTTCTG CACCTCAGCT TTTCCCGGAT    1020

AGGTGGGGAC CCATCATCAA AAGTGACAGA GAAGATAAGG CCCAGGGGCT TCAAGTCAC    1080

TAGTGGTTCC GTTTAGTAGA TGATTGTGCA TTGTTTCAAA ATGGTGCCCT AGTGACTACA    1140

AAGCCCCAGA GCCAGCATCA TCATCAAAGC AATGACAGTA GGTAAGCACC AGACCTCCTT    1200

GGGAGTGAGG AGGATTCTTG AGGAGAAAAG AGGTCTTCTT TCTCCTCTGC TGGAGACTAG    1260

TTGATCTGGA GACGTGGTTC CTTCAATGTC AGAGTTATCT TTGGGACTGG TCTCAAACTC    1320

TTCCAGTTGG GCCCTGGGGC AGGTCTCTCC ATCTGGAGCA TACTTACGTG CTCGGCGATT    1380

AAGGGTTCAG AATGCAGTGG TAGCCTGCTA CTCTGGCCAT CTTGGACCTT GATCCAGAGA    1440

ATCTCTGCTT CAGGAGCTTC TAAGAGAGTC CAGCCCTGCC TCCAGAGAGA GGCTTGCCCT    1500

TCACTGATGG CTGTGGAGCC TCTGATGAAA TATTATTGCT GGTCAGGAAT TCACTGTCTT    1560

ACAAGGAGGT TTCCTTCTTC TCTAGACAGT TCTGTTCATC AAAAAACTCT CCCTGTTCTT    1620

CTGAAATTGG AGTCTCTGGA AGTTCCACAC ATTAAGCTTA GTTCTTTTTC CTTGAACTG    1680

TCCAGGTTAC ATTAGTCCAG CCACTGTTTC ACAGGACCGA GATTAAACGA TCAACATCAT    1740

CATTCCCGGC ATGGATCATA GTCTGTTGTA GTCTACATAG CCCTAGTTTA TTTTTCTTCC    1800

CTTATTCTTC AAAGCTTTGG GTCCATTCAT TCTTCTAGTC CCAGTCCTCT GGACATGGTC    1860

TATTTAATTG TGTCCCTCTG ACACTGCAGT GACCAACCAT GATCTGGTCA AAGAGGATAA    1920

GAGTTTGAGC AGAAAACCAT CTTTAGCATA TATTTTTTTG CTTTGGTTCA TCAGCCCCAG    1980
```

```
ATATATTGTT TTCCTTACCC GTGCTTCTCT CACTCCTCAA GAAGAAGAAA GTGTGTGTTA    2040

GCATCTTTCT CTTGTCCTTC AAGACAAATT GGCATCTCTT GACGAGCGGA GAAGGTTCTT    2100

TTTTGGCCAG AATAAATAAA ATTAAAATAG AATCATCCAA CAGAATAATA AATCTTCGTG    2160

CAACAAGAAT ATATTATATA AACCCAGCAA TTTTGCAGGG CCTGGGTATA ACTAATTAGA    2220

AGTGTCTTAA ATTGCAGTCA AGATCCCACG GCAAGAGGAC TTTTGATAAA TACATTCTGG    2280

CCAGTAGGCA AGTGCGAGGG TGGTCCGTGC AGCAGCTCTG GAGGAGTTCT ATCCCAAAGC    2340

TATACTCAAC ACACAGGTTT CCCACTGACA ACAGGTCGCT CCCTTGCCTT CTTCCAGAAG    2400

AATCTGAGAA GCTTTGCTCC TTGAGTTTCA GTGCTGCCAA GGTGAGTACG AAAGGCTGCT    2460

CTTCTCATTC AGCTCCAGCC CACCCAGACC TGCTGGGCAG TTGATCCACT TTCCAAAATA    2520

GGAGGACACA CGGACAGGTT AGTGTTCTGG TCTGCTTTAC AAAGCTGTTG CCTGACAGGA    2580

GCAAGAGTTG CTGAGTGTCT GCTGGGTTCC AGGCTGTTCT GAGCTTGGAT GGGCAGGGGC    2640

TAAGCCACAG GGCCTGCATG AGCCCTGCCT TGAAGGGACT TAAAAGACGA CCTAATTATA    2700

GGCCTAGGAA TTTTACAGTA TTGCAACTGC AATGTGATGC TGAAAGTGGA AAATGATGTC    2760

CTGGGCTCAG AGAAAAGCCC ACACCAGCCT GGGAGTCATG ATAGCAGCAG AGTGCTTGGG    2820

GAGGGTGTGT CAGAGCATAA AGCAGCATGA ATGCTACAAA AGAAGATGCC AACTAGAGAT    2880

ATAGGTTGTC ATCAGGTCCC GGAGGAGCCA TGACCGTCTA GCTGAGAGCC ATGACCAAGG    2940

ACACAATGTC CAAGTGACTG TGAGGACCTC AGTCTGCCCT GTGGATGTGT ATGCCACAGA    3000

CCTGACTTCT GGAGGGCTGA CTGAAATGTT CATTTTAAGC TTTTTCTTCT CTTTCCCTGA    3060

AACACTCAGT TTGGGTTAGG GGTCATAGAC TAAGACCAAA GAGTCCAGGG TTAGAATCTT    3120

GGTGTAAAAT TGCAGGCCAT CTCAGGAAAT CTGTGAGCAG ATGGGATTGG CTTTGGGTAA    3180

GGTGCGTGTG GAAAATGTCA GTGGGAGCCG GGTCATGGTG GGCCTTTAGC ATCAGATTCC    3240

AGAGTGCAGA TAGTCTGTAT AGCTCATGTG AAACAGGGAG CCACCAAAAC TTTGGGGAGC    3300

AGGCTAGTGC CGGTTTTGAC CACCTGTGGA GCAGTGCTCA CTCACGAAGG CATTTTGCCA    3360

TCACATGAAT GTGCAGAAAG GAGGCCAAAA GCATTCTGTG CTTCTCCACC ACAGCACAGA    3420

CTTCCCTAGT CTCATTTGCT GAGAGTAGAC ATTCTGAGGG CCAGCAGTGC AGGTGTGATG    3480

TGCCTCAGAG GGTATGAAGC CCTTAGTCAG CCATCTGGAT ATCAGCTGCG TGGGCATGAT    3540

ATCTAGAAGG CTAATTGATT TTTTCACTTT CACCTGACTC TCTTGCCAAC CTGCAGAGAC    3600

AGACATTGGG TGTAGGACAG TGAACTGAGA AGGAAGCTAT TAAGATTCTG GCCTTGGCTT    3660

AGCTCTCAAC TGGCCATTGG TCTTGCAGTA AGTCTTTTTT CTGGGCTTCT TCTGGTCCTA    3720

TTTGTATGTA TTGCATTGTC ACATCATGCC TCTATCCTAG GAATACTGT GAGCTGAAAA    3780

ATGAGACCCT TACTGTTCAC GTCCTGCTAA GGGGGACCGT CGTGTCAGCA CTGTAATGCA    3840

GTGATGTTTT TTGTGTCTTT CAGGTGACTT C ATG GTC ATG ACG ATT TTC TTC     3892
                                 Met Val Met Thr Ile Phe Phe
                                  1               5

AAT GTG AGC AGG CGG TTT GGC TAT GTT GCC TTT CAA AAC TAT GTC CCT    3940
Asn Val Ser Arg Arg Phe Gly Tyr Val Ala Phe Gln Asn Tyr Val Pro
         10                  15                  20

TCT TCC GTG ACC ACG ATG CTC TCC TGG GTT TCC TTT TGG ATC AAG ACA    3988
Ser Ser Val Thr Thr Met Leu Ser Trp Val Ser Phe Trp Ile Lys Thr
     25                  30                  35

GAG TCT GCT CCA GCC CGG ACC TCT CTA GGG ATC ACC TCT GTT CTG ACC    4036
Glu Ser Ala Pro Ala Arg Thr Ser Leu Gly Ile Thr Ser Val Leu Thr
 40                  45                  50                  55
```

-continued

```
ATG ACC ACG TTG GGC ACC TTT TCT CGT AAG AAT TTC CCG CGT GTC TCC          4084
Met Thr Thr Leu Gly Thr Phe Ser Arg Lys Asn Phe Pro Arg Val Ser
             60                  65                  70

TAT ATC ACA GCC TTG GAT TTC TAT ATC GCC ATC TGC TTC GTC TTC TGC          4132
Tyr Ile Thr Ala Leu Asp Phe Tyr Ile Ala Ile Cys Phe Val Phe Cys
             75                  80                  85

TTC TGC GCT CTG TTG GAG TTT GCT GTG CTC AAC TTC CTG ATC TAC AAC          4180
Phe Cys Ala Leu Leu Glu Phe Ala Val Leu Asn Phe Leu Ile Tyr Asn
             90                  95                 100

CAG ACA AAA GCC CAT GCT TCT CCT AAA CTC CGC CAT CCT CGT ATC AAT          4228
Gln Thr Lys Ala His Ala Ser Pro Lys Leu Arg His Pro Arg Ile Asn
            105                 110                 115

AGC CGT GCC CAT GCC CGT ACC CGT GCA CGT TCC CGA GCC TGT GCC CGC          4276
Ser Arg Ala His Ala Arg Thr Arg Ala Arg Ser Arg Ala Cys Ala Arg
120                 125                 130                 135

CAA CAT CAG GAA GCT TTT GTG TGC CAG ATT GTC ACC ACT GAG GGA AGT          4324
Gln His Gln Glu Ala Phe Val Cys Gln Ile Val Thr Thr Glu Gly Ser
                140                 145                 150

GAT GGA GAG GAG CGC CCG TCT TGC TCA GCC CAG CAG CCC CCT AGC CCA          4372
Asp Gly Glu Glu Arg Pro Ser Cys Ser Ala Gln Gln Pro Pro Ser Pro
            155                 160                 165

GGT AGC CCT GAG GGT CCC CGC AGC CTC TGC TCC AAG CTG GCC TGC TGT          4420
Gly Ser Pro Glu Gly Pro Arg Ser Leu Cys Ser Lys Leu Ala Cys Cys
            170                 175                 180

GAG TGG TGC AAG CGT TTT AAG AAG TAC TTC TGC ATG GTC CCC GAT TGT          4468
Glu Trp Cys Lys Arg Phe Lys Lys Tyr Phe Cys Met Val Pro Asp Cys
            185                 190                 195

GAG GGC AGT ACC TGG CAG CAG GGC CGC CTC TGC ATC CAT GTC TAC CGC          4516
Glu Gly Ser Thr Trp Gln Gln Gly Arg Leu Cys Ile His Val Tyr Arg
200                 205                 210                 215

CTG GAT AAC TAC TCG AGA GTT GTT TTC CCA GTG ACT TTC TTC TTC TTC          4564
Leu Asp Asn Tyr Ser Arg Val Val Phe Pro Val Thr Phe Phe Phe Phe
                220                 225                 230

AAT GTG CTC TAC TGG CTT GTT TGC CTT AAC TTG TAGGTACCAG CTGGTACCCT        4617
Asn Val Leu Tyr Trp Leu Val Cys Leu Asn Leu
            235                 240

GTGGGGCAAC CTCTCCAGTT CCCCAGGAGG TCCAAGCCCC TTGCCAAGGG AGTTGGGGGA       4677

AAGCAGCAGC AGCAGCAGGA GCGACTAGAG TTTTTCCTGC CCCATTCCCC AAACAGAAGC       4737

TTGCAGAGGG TTTGTCTTTG CTGCCCCTCT CCCCTACCTG GCCCATTCAC TGAGTCTTCT       4797

CAGCAGACCA TTTCAAATTA TTAATAAATG GGCCACCTCC CTCTTCTTCA AGGAGCATCC       4857

GTGATGCTCA GTGTTCAAAA CCACAGCCAC TTAGTGATCA GCTCCCTAAA ACCATGCCTA       4917

AGTACAGGCG GATTAGCTAT CTTCCAACAA TGCTGACCAC CAGACAATTA CTGCATTTTT       4977

CCAGAAGCCC ACTATTGCCT TTGTAGTGCT TTCGGCCCAG TTCTGGCCTC AGCCTCAAAG       5037

TGCACCGACT AGTTGCTTGC CTATACCTGG CACCTCATTA AGATGCTGGG CAGCAGTATA       5097

ACAGGAGGAA GAGATCCCTC TCCTTTGGTC AGATTATTAT GTTCTCAGTT CTCTCTCCCT       5157

GCTACCCCTT TCTCTGCAGA TAGATAGACA CTGGCATTAT CCCTTTAGGA AGAGGGGGGG       5217

GCAGCAAGAG AGCCTATTTG GACAGCATT CCTCTCTCTC TGCTGCTGTG ACATCTCCCT       5277

CTCCTTGCTG GCTCCATCTT TCGTCTGCAC TACCAATTCA ATGCCCTTCA TCCAATGGGT       5337

ATCTATTTTT GTGTGTGATT ATAGTAACTA CTCCCTGCTT TATATGCCAC CCTCTTCCTT       5397

CTCTTTGACC CCTGTGACTC TTTCTGTAAC TTTCCCAGTG ACTTCCCCTA GCCCTGACCC       5457

AGGCACTAGG CCTTGGTGAC TTCCTGGGGC CAAGAAACTA AGGAAACTCG GCTTTGCAAC       5517

AGGCATTACT CGCCATTGAT TGGTGCCCAC CCAGGGCACA CTGTCGGAGT TCTATCACTT       5577
```

```
GCTTGACCCC TGGACCCATA AACCAGTCCA CTGTTATACC CGGGGCACTC TAACCATCAC    5637

AATCAATCAA TCAAATTCCC TTAAATTTGT ATGGCACTGG AACTTTGGCA AAGCACTTTT    5697

GACAAGTTGT GTCTGATTGG AGCTTCATGA TAGCCTTGTG ACATCTTTAG GGCAGGATTC    5757

TTATCCCCAT TTTGCAGATG AAAACCCTGA GTCACAGATT TCTGTGGGAC TGTGGATCTC    5817

ACTGGAAGCT ATCCAAGAGC CCACTGTCAC CTTCTAGACC ACATGATAGG GCTAGACAGC    5877

TCAGTTCACC ATGATTCTCT TCTGTCACCT CTGCTGGCAC ACCAGTGGCA AGGCCCAGAA    5937

TGGCGACCTC TCTTTAGCTC AATTTCTGGG CCTGAGGTGC TCAGACTGCC CCCAAGATCA    5997

AATCTCTCCT GGCTGTAGTA ACCCAGTGGA ATGAATTTGG ACATGCCCCA ATGCTTCTAT    6057

ATGCTAAGTG AAATCTGTGT CTGTAATTTG TTGGGGGGTG GATAGGGTGG GGTCTCCATC    6117

TACTTTTTGT CACCATCATC TGAAATGGG                                     6146
```

(2) INFORMATION FOR SEQ ID NO:2:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Met Thr Ile Phe Phe Asn Val Ser Arg Arg Phe Gly Tyr Val
 1               5                  10                  15

Ala Phe Gln Asn Tyr Val Pro Ser Ser Val Thr Thr Met Leu Ser Trp
                20                  25                  30

Val Ser Phe Trp Ile Lys Thr Glu Ser Ala Pro Ala Arg Thr Ser Leu
            35                  40                  45

Gly Ile Thr Ser Val Leu Thr Met Thr Thr Leu Gly Thr Phe Ser Arg
        50                  55                  60

Lys Asn Phe Pro Arg Val Ser Tyr Ile Thr Ala Leu Asp Phe Tyr Ile
65                  70                  75                  80

Ala Ile Cys Phe Val Phe Cys Phe Cys Ala Leu Leu Glu Phe Ala Val
                85                  90                  95

Leu Asn Phe Leu Ile Tyr Asn Gln Thr Lys Ala His Ala Ser Pro Lys
               100                 105                 110

Leu Arg His Pro Arg Ile Asn Ser Arg Ala His Ala Arg Thr Arg Ala
           115                 120                 125

Arg Ser Arg Ala Cys Ala Arg Gln His Gln Glu Ala Phe Val Cys Gln
       130                 135                 140

Ile Val Thr Thr Glu Gly Ser Asp Gly Glu Arg Pro Ser Cys Ser
145                 150                 155                 160

Ala Gln Gln Pro Pro Ser Pro Gly Ser Pro Glu Gly Pro Arg Ser Leu
                165                 170                 175

Cys Ser Lys Leu Ala Cys Cys Glu Trp Cys Lys Arg Phe Lys Lys Tyr
            180                 185                 190

Phe Cys Met Val Pro Asp Cys Glu Gly Ser Thr Trp Gln Gln Gly Arg
        195                 200                 205

Leu Cys Ile His Val Tyr Arg Leu Asp Asn Tyr Ser Arg Val Val Phe
    210                 215                 220

Pro Val Thr Phe Phe Phe Asn Val Leu Tyr Trp Leu Val Cys Leu
225                 230                 235                 240

Asn Leu
```

(2) INFORMATION FOR SEQ ID NO:3:

(i) SEQUENCE CHARACTERISTICS:
        (A) LENGTH: 556 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
TCCCCGGCTC CCCACCGCAG CAGCCGTCAC GTCGTCGGAG ATTTCCATCG GGGCGGGCCT      60
GGGGCGGGGA GCGCGGGACG GGGCGGGGCG AGTGGGAGGA GTGAAAGTTG GAGCCCAGCA     120
AAAGCCTCCG CCCCGCGCTC AGTGCGGCCA GAGCGTGAGC CGCGACCTCC GCGCAGGTGG     180
TCGCGCCGGT CTCCGCGGAA ATGTTGTCCA AAGTTCTTCC AGTCCTCCTA GGCATCTTAT     240
TGATCCTCCA GTCGAGGTGA GTCTCCATCC CGGGACCCGG GAGCCCTTCG CGCCCAGCTC     300
CCTCTCCCCG GGAGCCGGGA CGGCTCCCGG GACCCCAGCG GCCCCGCGTT CCTCGAGCCC     360
CGCGCCCGCT TTGCCCCGGC CCTACCGCGG GCTGGCCGAG TCCCGCGTCC CCTCGATGCG     420
CGCCGGCCTC GGCCCGCCTC ACTGTAGGAT GGGCTCCCGG GGTCCTTGAG GGGGAGCTCC     480
AAAAGGAAGA CAGGACGCCA GAAGGAAGAC GGGACTCCAG TTCGCGGATT CCCGCTCTCA     540
AAAGCACTGC GGTGGC                                                    556
```

(2) INFORMATION FOR SEQ ID NO:4:

(i) SEQUENCE CHARACTERISTICS:
        (A) LENGTH: 1097 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
GGCACTAGCT GGGGCCCCTA CAGAGTGCAG GGCAGAGCTT CATTTTTCGT TTGAATGTTA      60
TAGGGTCGAG GGACCTCAGA CTGAATCAAA GAATGAAGCC TCTTCCCGTG ATGTTGTCTA     120
TGGCCCCCAG CCCCAGCCTC TGGAAAATCA GCTCCTCTCT GAGGAAACAA AGTCAACTGA     180
GACTGAGACT GGGAGCAGAG TTGGCAAACT GCCAGAAGCC TCTCGCATCC TGAACACTAT     240
CCTGAGTAAT TATGACCACA AACTGCGCCC TGGCATTGGA GGTGAGGAGC AGAACGACGT     300
TCTTCCCCTC CTAGAGGGTC CAGGGGTTGA GGGCATAGGC ATGGAGAATG CACCTGGGCA     360
GTAACAGAGG GTGCCATGCT CATGGACAGG AACATCTGCT ATTGACCTGT CAGGTAAGAG     420
ATATTAACTC TATTCTCAGC AGTGTCATTG ACCTTGATCA AGACTTTTCC CTTCTCTCGC     480
CCTCAGTTTT TCCAGTGGTA AAATGAGAGG ACTAAACTAG ATTGTTGATC TTCAAGATGT     540
GTGTCCAATT CTTAACAGTC CGTGAGCTTG GTTTTGCCAT GAAAGAATAA ATAAAGAAAT     600
AGGATTAGAT GCTGAAACTG TGTGGTCCAA CACTTACTTG ACTCCCCTTT CATCCCCTCT     660
GACCACTTCC TCCCCCGTCC CATGCGCCTG TTTGACACTT ACCCTCTGCT GCTTCTGCTT     720
CCCTTATAGA GAAGCCCACT GTGGTCACTG TTGAGATCTC CGTCAACAGC CTTGGTCCTC     780
TCTCTATCCT AGACATGGTG AGTACTAAGC TTTTTTAGTA CTATTTCCTA GCCCAGGGGC     840
TGACCTATGG GACCTTCCAC AGACTTCTGC TTTCTGCTCT GTACTTCTGT AACAACTCCA     900
ATAATTTATT TTCTGGAGGG AGAAAGGGAT TTTTTAACCA CTGGTTTGAG AATGAGACTG     960
```

-continued

| | |
|---|---|
| GAAAAGGTAA GTCCCTTGCT ACTTGAAGAG GATCTTCAGA ATCATGACCA TATCTTCCAG | 1020 |
| TTTTTTCATT CAAAATAGAA ATAATAAAGC AATGTTAAAC ACCACAATGG ACTGCCTCTT | 1080 |
| TTCTTCTGAT AATTATT | 1097 |

(2) INFORMATION FOR SEQ ID NO:5:

(i) SEQUENCE CHARACTERISTICS:
        (A) LENGTH: 9631 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

| | |
|---|---|
| TGCATGATGT GAGGACCTAG CTCCCCTTGC TCACGGTAAT CAAGCAGGGC ATGACTGACT | 60 |
| TCTCATTTGG GATCATTAGG CTTGGTAACC TCTGAGTTCC CTTCTAGTTC TGACATTGGA | 120 |
| AGAGTCTTTG AGCAGAGAGA AGGGACCTCA TCTGACTCCT GCTTCCTGGT CTAGTGCTCA | 180 |
| ATGCATTCCA CCACATTGCC TTTAGGATTC TAGGTTAGGG AGTGGCAAAC AATATGTTTG | 240 |
| CATGTGAATG TCCTTTTTCT GTTCATCCCC AAGTATGTGC TTTTCTGTCC TTCCCACCAG | 300 |
| GAATACACCA TTGACATCAT CTTCTCCCAG ACCTGGTACG ACGAACGCCT CTGTTACAAC | 360 |
| GACACCTTTG AGTCTCTTGT TCTGAATGGC AATGTGGTGA GCCAGCTATG GATCCCGGAC | 420 |
| ACCTTTTTTA GGAATTCTAA GAGGACCCAC GAGCATGAGA TCACCATGCC CAACCAGATG | 480 |
| GTCCGCATCT ACAAGGATGG CAAGGTGTTG TACACAATTA GGTATGTCAA GCCTCTGGAG | 540 |
| TCTCACTTCC TGGAATTCTC TCTCCCCTTC TGATAATTTT AGCTAAAGAT CCATGGGCAG | 600 |
| AGATCTCATC CTGAATGATA CCTCTAAGGG CCTGTCCAGC TTTCCTAGAC CATGAGCTCA | 660 |
| GCCCCCTTAT GTAACAGATA TAGAGGCCTC AAAATAGAAA GATATTGCTT AAAGCCACAC | 720 |
| ACCAAGTTTG TGGCAGAGCT GGAACTGGTA CTCAGTTACT TGGCTCCGAG TCCAGAGCTC | 780 |
| CCTCAACTAG GATGTGCCAG TATGACTGCA TTATCTAGAC AATTCCATCC TACGTGGGCA | 840 |
| CTCGATACAA AGATACGTCC ACAGTGGTGG AATTGTTCAG GCAGAGCAGC AGCACGTAGT | 900 |
| GGCAAAGGTA CCTAAGATCA AGTTGGATAC TTGAATTCCC AGCAGGGGAA GGTTGTGTGT | 960 |
| GGGGATAGCA GGGAGGATGT TGGCAGTTCC TGGAAACTAG GGTGGGCGAG AAAACAAAAG | 1020 |
| CCGATCGAAG TTGCTCCATA CGTTTCTCTA ATGATGGAGC CCAGAGTAAC CAGATACTTC | 1080 |
| TAAGCTGTTT GTTTGTTTTG TTTTGTTTTG TTTTGTTTTG TTTTGTTTTG TTTTCTCTCT | 1140 |
| TGTTATCTCT CCTTTGAGCT TTTTGTCTTA AATTCTAGCG AGGTCCAGGC ACGGTGGCTC | 1200 |
| ACGCCTGTGA TCCCAGCACT TTGTGAGGCT GAGGCAGGCA GATCACTTGA GGTCAGGAGT | 1260 |
| TCGAGACCAG CCTGGCCATC ATGGGAAAAC CCTGTCTCCA CTAAAAATGC AAAAATTAGC | 1320 |
| AGGGTGTGCT GGCACTAATT CCAGCTACTC GGGAGGCTAG GCATGAGAA TTGCTTGAGC | 1380 |
| CTGGGAGGCA AGAGGCTGCA GTGAGCTGAC ATCACGCCAC TGCCCTCCAG CCTGGGTGAC | 1440 |
| AGAGTGAGAC TCTGTCTCAA ACAAACAAAG AAAAAAATTG ACTCTGGCCA TTCATTGGTG | 1500 |
| GTAGTCCCTA GACCAAAGCT GGGTGGATAC GGAAGTGCTT AGGGCCAGCC TGATGAGGCT | 1560 |
| CCTTTCTCCC TTCCAGGATG ACCATTGATG CCGGATGCTC ACTCCACATG CTCAGATTTC | 1620 |
| CAATGGATTC TCACTCTTGC CCTCTATCTT TCTCTAGCTG TGAGTACCTT CTTAAGTTTC | 1680 |
| TGGGGCCCCA GAAACATGCT GGGCTCCTTC TTTTTCTCAT CCTTGCCATT TACATTTTTC | 1740 |
| TGCCTCTGCT TTTCTTCTAA AATGCTGCCA AGGTTGTGCA GGACTTCCAT CCTCCACCCT | 1800 |

-continued

```
CATTTCCTTT CCTGCCAACA ATACTGTGTT GCTCATCCCT TCCACGTGCC TCTGAAGCGT    1860

ATCTCAAGTA TGTCTGCTCC TCTCCATCTC CACTGGCACT ACCTTGGTTT AGGCCTTTGT    1920

TATCTTCCAC CTGGACTTTT GCCACATCTT CACTTTGAAA CTGCACATGT CCAAAATGAA    1980

ATTCATTGTC TCCTCCAAAC CTCTACCACC AAAACAAGTG TGTTGCTTCT GGGTTCCCAT    2040

CTGTCTCATT GAAGAGGACC ATCACTCACC CAGTTGCGCA AATCAAGAAC TTTGATGTTT    2100

CCTCTCCCTC ACCTCCTGCA TCTAATCAAT CAGCACATCC TGTTGGTGTT TCCTCCCAGT    2160

CTCTATCGAT GCTGTCTATT TCTCTGCACC CTGTACAGCT TTGACTTCCA CCTGCATTAA    2220

TTTAATTCTG CCTGGATTAC TACACTGGCC TCCTTGACAA CATGTTGTCC TCACAGAAGG    2280

ACCAGAGTGA CCTAGCTGAA GGGTCACCTA GGTTGGGTCA CTTCTTAGTC TCGAATCTGC    2340

CGTTAACTCT CATGGATCAA TTTGAAATTC CTTAGAATGA ACCTCAAGGC CATTCATGAA    2400

CTGGACCCTG CCACCCAATC CTGTGCACCT CATCCTCTGT GAGCTAGCCA TCCTGAACTT    2460

TTGTCCTTTC CACAATACAC CAGGTGTTTC ACCTTTCTAT ACTGCCCCTT AACCCCTTCA    2520

ACCTCATTCT TATTGAGAAT ATTTACTTGA GTTTCAAGAT TTAATGGGAA TATCACCTGC    2580

TTTATGAAGT CTTTTCTGAG TATGTCCCCA AGTGACCTTT ATCTACTTTG TTTCCCCGCT    2640

GTTCTGTGGA CTTAGGTTTT TCAGAGCTCC TCCAAAAATC ACAGTAGTAT ACTCACTGTC    2700

TTATAAAATT AAATGTGATT GCTTGAGGGT AGGGTTCATG CCTTGCTCAT CTCTGTATTT    2760

CTGGCCTAGG GCCTGATACT GAGGAATGCT CAGTAAACGC ACTCATTGAA TGGACTTCAA    2820

CAATGAGGTA AGAGAGGCAA GGTCCCACAG CTGGTGAGGC CAGAGACAGG ACTCCAAGGC    2880

ATTGTGCAGG CTGAGTTCAT GCTATTGGAG ACCTCAGGTG GGCTTCCAAG TCTCATAGGA    2940

CCCTCTTTCT CACATTCCTT TCCAGTTTCC TATCCTGAGA ATGAGATGAT CTACAAGTGG    3000

GAAAATTTCA AGCTTGAAAT CAATGAGAAG AACTCCTGGA AGCTCTTCCA GTTTGATTTT    3060

ACAGGAGTGA GCAACAAAAC TGAAATAATC ACAACCCCAG TTGGTAAGCG TGCCAGGGCT    3120

TGGCGGAAGT CCAGGAAGGT GGTAGGGATG ATTGGAGATG CCATCCATA CAAATGCTTT    3180

GCAGTCATCC CGTGCAAACA TTGTAAGACA TGGCTCCTGT CTTATAATTG CTAAGCACTT    3240

ACAACTGTTT GCAGAGGAAA CTGAGACTTT GTAACTATGT CTCAGTCTCA TCTGCAAAGA    3300

AGTAAGTGCT TGCCAAGCT CCTTGAGAGG TTAGGTAAGT AGATAAAGTT CTGCTGCTGT    3360

CGGAATGTGC AGCTGGCTTT TTCATGCAGA CCCTTCAGTT TCGAGGTTAC AACTCTGACC    3420

TCTTTGGATG ACTTTGGGGA ATGGAGCTCG TGTGAGTTCT CCATACCCAG AACCAATCCA    3480

GTCTGGTTGA ATGGGAAGCA AAGTCCATTG TAGTGGGAGG TGGAGGCTAG AGTTCTAATG    3540

TCAGCTAGTT TAAGGCTGGG AAAGTCTGGA GGAAGTTACA GCAGCTACAC TGGCTGCTGC    3600

ATTGACATTT ATCTTAAAGG AACAAGTCTG AAAAGCACAG ATTCTTATCA AAGGCTTCAT    3660

GGTGGATTCC ACATAGACAT AGTGGCCACT GGTTTTCTGA CCTTTTCTCT GACAAAGACT    3720

AAAGGGGAAG GTCCTGGGTA TCTTACACTT CAGCTCCCAA TTAGATGTGA GCACCTTCAC    3780

TTATGTTCCT AGGTGACCTG AATGAGGAGC CAAGGGACCT CCCCAGGGTA GCTCCCAGAG    3840

CAACCCTGGA AACACTCTTC ACACATCCTG ACCAAGTTCA GGGCAGTGAA GGCACTGCCC    3900

TCATCGTTTC CAGAATGTGG ATGGAGCCAG TCACCCAACC AGCCATTTGT CGTGAGAGGC    3960

ATCTTGTTCT GCTACCATGT GACTAGGCAG AAAATCTGCT TTTGTTTCAT TTATTGAGTC    4020

AGTCTCTGGA TGAGGGAAAG CTCATGCTCA TGTGGCTAGA GCTTTGCTTG CACAGTATTA    4080

GGCAGGGGCA GAGGGCTGGG CTACCTTAAA AATACTTGCC CTTTTTCTTG GGGACTCTGG    4140

GGAAGCGGTT TTACTACCTT TGACTTGGGA GCCTTGCTCT TCTGCCAGCT AACCATGGGC    4200
```

```
CTGCCTCTTG GTTTTCTGCA CCTCAGCTTT TCCCGGATAG GTGGGACCC  ATCATCAAAA    4260

GTGACAGAGA AGATAAGGCC CAGGGGCTTT CAAGTCACTA GTGGTTCCGT TTAGTAGATG    4320

ATTGTGCATT GTTTCAAAAT GGTGCCCTAG TGACTACAAA GCCCCAGAGC CAGCATCATC    4380

ATCAAAGCAA TGACAGTAGG TAAGCACCAG ACCTCCTTGG GAGTGAGGAG GATTCTTGAG    4440

GAGAAAAGAG GTCTTCTTTC TCCTCTGCTG GAGACTAGTT GATCTGGAGA CGTGGTTCCT    4500

TCAATGTCAG AGTTATCTTT GGGACTGGTC TCAAACTCTT CCAGTTGGGC CCTGGGGCAG    4560

GTCTCTCCAT CTGGAGCATA CTTACGTGCT CGGCGATTAA GGGTTCAGAA TGCAGTGGTA    4620

GCCTGCTACT CTGGCCATCT TGGACCTTGA TCCAGAGAAT CTCTGCTTCA GGAGCTTCTA    4680

AGAGAGTCCA GCCCTGCCTC CAGAGAGAGG CTTGCCCTTC ACTGATGGCT GTGGAGCCTC    4740

TGATGGAATA TTATTGCTGG TCAGGAATTC ACTGTCTTAC AAGGAGGTTT CCTTCTTCTC    4800

TAGACAGTTC TGTTCATCAA AAAACTCTCC CTGTTCTTCT GAAATTGGAG TCTCTGGAAG    4860

TTCCACACAT TAAGCTTAGT TCTTTTTCCT TGGAACTGTC CAGGTTACAT TAGTCCAGCC    4920

ACTGTTTCAC AGGACCGAGA TTAAACGATC AACATCATCA TTCCCGGCAT GGATCATAGT    4980

CTGTTGTAGT CTACATAGCC CTAGTTTATT TTTCTTCCCT TATTCTTCAA AGCTTTGGGT    5040

CCATTCATTC TTCTAGTCCC AGTCCTCTGG ACATGGTCTA TTTAATTGTG TCCCTCTGAC    5100

ACTGCAGTGA CCAACCATGA TCTGGTCAAA GAGGATAAGA GTTTGAGCAG AAAACCATCT    5160

TTAGCATATA TTTTTTTGCT TTGGTTCATC AGCCCCAGAT ATATTGTTTT CCTTACCCGT    5220

GCTTCTCTCA CTCCTCAAGA AGAAGAAAGT GTGTGTTAGC ATCTTTCTCT TGTCCTTCAA    5280

GACAAATTGG CATCTCTTGA CGAGCGGAGA AGGTTCTTTT TTGGCCAGAA TAAATAAAAT    5340

TAAAATAGAA TCATCCAACA GAATAATAAA TCTTCGTGCA ACAAGAATAT ATTATATAAA    5400

CCCAGCAATT TTGCAGGGCC TGGGTATAAC TAATTAGAAG TGTCTTAAAT TGCAGTCAAG    5460

ATCCCACGGC AAGAGGACTT TTGATAAATA CATTCTGGCC AGTAGGCAAG TGCGAGGGTG    5520

GTCCGTGCAG CAGCTCTGGA GGAGTTCTAT CCCAAAGCTA TACTCAACAC ACAGGTTTCC    5580

CACTGACAAC AGGTCGCTCC CTTGCCTTCT TCCAGAAGAA TCTGAGAAGC TTTGCTCCTT    5640

GAGTTTCAGT GCTGCCAAGG TGAGTACGAA AGGCTGCTCT TCTCATTCAG CTCCAGCCCA    5700

CCCAGACCTG CTGGGCAGTT GATCCACTTT CCAAAATAGG AGGACACACG GACAGGTTAG    5760

TGTTCTGGTC TGCTTTACAA AGCTGTTGCC TGACAGGAGC AAGAGTTGCT GAGTGTCTGC    5820

TGGGTTCCAG GCTGTTCTGA GCTTGGATGG GCAGGGGCTA AGCCACAGGG CCTGCATGAG    5880

CCCTGCCTTG AAGGGACTTA AAAGACGACC TAATTATAGG CCTAGGAATT TTACAGTATT    5940

GCAACTGCAA TGTGATGCTG AAAGTGGAAA ATGATGTCCT GGGCTCAGAG AAAAGCCCAC    6000

ACCAGCCTGG GAGTCATGAT AGCAGCAGAG TGCTTGGGGA GGGTGTGTCA GAGCATAAAG    6060

CAGCATGAAT GCTACAAAAG AAGATGCCAA CTAGAGATAT AGGTTGTCAT CAGGTCCCGG    6120

AGGAGCCATG ACCGTCTAGC TGAGAGCCAT GACCAAGGAC ACAATGTCCA AGTGACTGTG    6180

AGGACCTCAG TCTGCCCTGT GGATGTGTAT GCCACAGACC TGACTTCTGG AGGGCTGACT    6240

GAAATGTTCA TTTTAAGCTT TTTCTTCTCT TTCCCTGAAA CACTCAGTTT GGGTTAGGGG    6300

TCATAGACTA AGACCAAAGA GTCCAGGGTT AGAATCTTGG TGTAAAATTG CAGGCCATCT    6360

CAGGAAATCT GTGAGCAGAT GGGATTGGCT TTGGGTAAGG TGCGTGTGGA AAATGTCAGT    6420

GGGAGCCGGG TCATGGTGGG CCTTTAGCAT CAGATTCCAG AGTGCAGATA GTCTGTATAG    6480

CTCATGTGAA ACAGGGAGCC ACCAAAACTT TGGGGAGCAG GCTAGTGCCG GTTTTGACCA    6540
```

```
CCTGTGGAGC AGTGCTCACT CACGAAGGCA TTTTGCCATC ACATGAATGT GCAGAAAGGA    6600

GGCCAAAAGC ATTCTGTGCT TCTCCACCAC AGCACAGACT TCCCTAGTCT CATTTGCTGA    6660

GAGTAGACAT TCTGAGGGCC AGCAGTGCAG GTGTGATGTG CCTCAGAGGG TATGAAGCCC    6720

TTAGTCAGCC ATCTGGATAT CAGCTGCGTG GGCATGATAT CTAGAAGGCT AATTGATTTT    6780

TTCACTTTCA CCTGACTCTC TTGCCAACCT GCAGAGACAG ACATTGGGTG TAGGACAGTG    6840

AACTGAGAAG GAAGCTATTA AGATTCTGGC CTTGGCTTAG CTCTCAACTG GCCATTGGTC    6900

TTGCAGTAAG TCTTTTTTCT GGGCTTCTTC TGGTCCTATT TGTATGTATT GCATTGTCAC    6960

ATCATGCCTC TATCCTAGGG AATACTGTGA GCTGAAAAAT GAGACCCTTA CTGTTCACGT    7020

CCTGCTAAGG GGGACCGTCG TGTCAGCACT GTAATGCAGT GATGTTTTTT GTGTCTTTCA    7080

GGTGACTTCA TGGTCATGAC GATTTTCTTC AATGTGAGCA GGCGGTTTGG CTATGTTGCC    7140

TTTCAAAACT ATGTCCCTTC TTCCGTGACC ACGATGCTCT CCTGGGTTTC CTTTTGGATC    7200

AAGACAGAGT CTGCTCCAGC CCGGACCTCT CTAGGTAAGA GGAGAAACAG GTATACGCAT    7260

AGGCACATGG CTGGGAGTTG GCTGGGCCAG GGCAGAGTTG CCTTGTCATG GAGTCTTTTA    7320

ACCAATGTCG CACATAGGTC AGGAGCTGAG CCCATCACTC TTGTGCTCTT GCAGGGATCA    7380

CCTCTGTTCT GACCATGACC ACGTTGGGCA CCTTTTCTCG TAAGAATTTC CCGCGTGTCT    7440

CCTATATCAC AGCCTTGGAT TTCTATATCG CCATCTGCTT CGTCTTCTGC TTCTGCGCTC    7500

TGTTGGAGTT TGCTGTGCTC AACTTCCTGA TCTACAACCA GACAAAAGCC CATGCTTCTC    7560

CTAAACTCCG CCATGTATGA GCTGGGTATG GGAGTGGTGG CAAGGCTTTG GAGTGTAGAG    7620

ACATGCTAGC AAGGGTACTG GGGTTATGGC ACATGGGTGG TCAGCTTGCT GAGTGATGGA    7680

ATGTTACCCA GGGTGGTGGC GGGGTTGAAT CAACTTCCTG ATGTAATGGT GAGAAGTTGG    7740

AGGAGAGAAG CCAAGATATG GTGTGCCAAA GACAGTTTCC AGAAAATCCG GAGGCAGCAC    7800

TTAGACTTGG GTTATCTTCC CTTGACTTTT CCCCACTTCT TTCCTTGTCC ATTTTAGCCT    7860

CGTATCAATA GCCGTGCCCA TGCCCGTACC CGTGCACGTT CCCGAGCCTG TGCCCGCCAA    7920

CATCAGGAAG CTTTTGTGTG CCAGATTGTC ACCACTGAGG GAAGTGATGG AGAGGAGCGC    7980

CCGTCTTGCT CAGCCCAGCA GCCCCCTAGC CCAGGTAGCC CTGAGGGTCC CCGCAGCCTC    8040

TGCTCCAAGC TGGCCTGCTG TGAGTGGTGC AAGCGTTTTA AGAAGTACTT CTGCATGGTC    8100

CCCGATTGTG AGGGCAGTAC CTGGCAGCAG GGCCGCCTCT GCATCCATGT CTACCGCCTG    8160

GATAACTACT CGAGAGTTGT TTTCCCAGTG ACTTTCTTCT TCTTCAATGT GCTCTACTGG    8220

CTTGTTTGCC TTAACTTGTA GGTACCAGCT GGTACCCTGT GGGGCAACCT CTCCAGTTCC    8280

CCAGGAGGTC CAAGCCCCTT GCCAAGGGAG TTGGGGGAAA GCAGCAGCAG CAGCAGGAGC    8340

GACTAGAGTT TTTCCTGCCC CATTCCCCAA ACAGAAGCTT GCAGAGGGTT TGTCTTTGCT    8400

GCCCCTCTCC CCTACCTGGC CCATTCACTG AGTCTTCTCA GCAGACCATT TCAAATTATT    8460

AATAAATGGG CCACCTCCCT CTTCTTCAAG GAGCATCCGT GATGCTCAGT GTTCAAAACC    8520

ACAGCCACTT AGTGATCAGC TCCCTAAAAC CATGCCTAAG TACAGGCGGA TTAGCTATCT    8580

TCCAACAATG CTGACCACCA GACAATTACT GCATTTTTCC AGAAGCCCAC TATTGCCTTT    8640

GCAGTGCTTT CGGCCCAGTT CTGGCCTCAG CCTCAAAGTG CACCGACTAG TTGCTTGCCT    8700

ATACCTGGCA CCTCATTAAG ATGCTGGGCA GCAGTATAAC AGGAGGAAGA GATCCCTCTC    8760

CTTTGGTCAG ATTATTATGT TCTCAGTTCT CTCTCCCTGC TACCCCTTTC TCTGCAGTTA    8820

GATAGACACT GGCATTATCC CTTTAGGAAG AGGGGGGGGC AGCAAGAGAG CCTATTTGGG    8880

ACAGCATTCC TCTCTCTCTG CTGCTGTGAC ATCTCCCTCT CCTTGCTGGC TCCATCTTTC    8940
```

-continued

```
GTCTGCACTA CCAATTCAAT GCCCTTCATC CAATGGGTAT CTATTTTTGT GTGTGATTAT      9000

AGTAACTACT CCCTGCTTTA TATGCCACCC TCTTCCTTCT CTTTGACCCC TGTGACTCTT      9060

TCTGTAACTT TCCCAGTGAC TTCCCCTAGC CCTGACCCAG GCACTAGGCC TTGGTGACTT      9120

CCTGGGGCCA AGAAACTAAG GAAACTCGGC TTTGCAACAG GCATTGCTCG CCATTGATTG      9180

GTGCCCACCC AGGGCACACT GTCGGAGTTC TATCACTTGC TTGACCCCTG GACCCATAAA      9240

CCAGTCCACT GTTATACCCG GGGCACTCTA ACCATCACAA TCAATCAATC AAATTCCCTT      9300

AAATTTGTAT GGCACTGGAA CTTTGGCAAA GCACTTTTGA CAAGTTGTGT CTGATTGGAG      9360

CTTCATGATA GCCTTGTGAC ATCTTTAGGG CAGGATTCTT ATCCCCATTT TGCAGATGAA      9420

AACCCTGAGT CACAGATTTC TGTGGGACTG TGGATCTCAC TGGAAGCTAT CCAAGAGCCC      9480

ACTGTCACCT TCTAGACCAC ATGATAGGGC TAGACAGCTC AGTTCACCAT GATTCTCTTC      9540

TGTCACCTCT GCTGGCACAC CAGTGGCAAG GCCCAGAATG GCGACCTCTC TTTAGCTCAA      9600

TTTCTGGGCC TGAGGTGCTC AGACTGCCCC C                                     9631

(2) INFORMATION FOR SEQ ID NO:6:

(i) SEQUENCE CHARACTERISTICS:
        (A) LENGTH: 7479 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

TTCTACCAGA CCTGGTATGA TGAGCGCCTC TGTTACAATG ACACCTTTGA GACACTTATT        60

CTACATGGCA ACGTGGTGAG CCAGTTGTGG ATCCCGGATA CTTTTTTTAG GAATTCTAAG       120

AGGACCCAAG AGTATGATAT CACCATACCC AACCAGATGG CTCTCATCCA TAAGGATGGA       180

AAAGTGTTGT ACACAGTTAG GTATGTCAAG CCTTTAGTGT CTCACTTTCT AGGGCTCTCT       240

CACTCTTCCA GAAAATTTTA GCTAGGGACT CCTAAGTAAA TATATCATTC TGAATAATAT       300

TCCTAAAACC CTGTGCAGCT TTTCTAGATC AGGAATTCAA CCTCTTCCTG TGCAAATATA       360

AGACACTGAG ATATTAAATA AAAGATTTTA AAGATGCATG CCAAGTGTTT TGGTAATCAT       420

GGAGCTGTAT TTGCCCCACA GTCTAGAAGG TAGGTGCTGG CCTGACTGTA TTAGTAGATA       480

ATTCCATCCC AAATGGGCAT AGTATTTAAA GACACGCCCA CAGTGACAGA ATTGTCCAGG       540

CACAGTATAA ATACATCGGT GGAAAAGTAT TCAGGACTAG GATACATAAA TTGAATGCCT       600

GGAAGGAGAT GCTTGTGTCA GCAATATGGG ATGTGGAGGT GGTGCAAAGT AGCACAGGAC       660

TAGAGCACTG CACGAACAAG AAAGAAAAAT CAATCTAGGC TGGCCCATGT ACTTCTTTGA       720

TGATGTAGCC TAGTAGTCAG ATTTTAGAAG TTCTTCTTCC TCTCTTTGTA TCATTCCTTT       780

GGGCTTTTTG TCTTAAATTC TACTAATGGC ACTCATTAGA TATGATACCT GGTCAATGTT       840

GAGTAGATAT CAGTGCAAAG AGCCAGCCTA ATGAGGCTCC TTTCTCCCTT CCAGGATGAC       900

CATTGATGCA AGATGCTCAC TCCACATGCT CAATTTTCCA ATGGATTCTC ACTCTTGCCC       960

TCTGTCTTTC TCTAGCTGTG AGTACCTTCT TAGGTTTCTG GGGATCCAGA GATATGCTGG      1020

GCCCCACTTT TGCTCATCTT TGCCTTTTAC ATTTTTCTGC TTCTGCTTGT TTCCTGTGAT      1080

GGTGCCAGGG TTGCTATAAG CCTCCATTTT CCATCATCAC CCCTTTTCCT GTAAGCAGTG      1140

CTGTGTGTGT ATTGCTTTGG CTTTATGTTG AATTCTTCCC TCACCCTTGC TCTACCTTAA      1200

GCTAGTCACC TGCTTCTGAA GTATATCTGA AGTATGCCTG CTCCTCTCCA TCTCTGCCTT      1260
```

```
GATGCAGGGC TTTAATCATC TTCTGCTTGG ACTTCTACAG TACCTTCACT TTGAAACAGA    1320

GTGTGTCTTA AGCTAAATTC ATTTTTTTCT TCCCAACACC TGCCTCCAAA GCAAATGTGT    1380

CGCTTCTGTG TTGCCTCATT GAAGGGTGCC ATCATTTACC CAGCTACCCA AGCCAAGAAC    1440

TCTGACAGCC CCATTCATTG ACCTCCTACA TCTACTCAGT TCACACATCC TGTTGGTGTT    1500

CCCTCCAAAT CTCTATTGAT CTCACCTCCA TCTCTGCATT CTGACTATTA TTAGCTTTCA    1560

TTCCTCATTT CAAATGTGTT CTTTGCTCGC CTGGATCAAT TCTAAATGCC TTAAAATGAA    1620

CCTCAAATCC CTTCATGAGC TGACCCTGCT GCTTCCTGCT ATACAACCTA TCTGTGAAAT    1680

AGTCTCCCTA AAGTTTTGCT GTTTCCACAT TCACCTTTCT GTGCTTCCCT TTCACCTTCT    1740

TCAACCTCAT CTCTATTGAG AATGTTTATT TTCAAAACTT AAAGTGAATG CCCCATGCTT    1800

TAGGAAGTGG GTCCCAAGAG ATCTTTCCCT ATTTTGCCAA TTGTTCCATG GGTAGAGATT    1860

TTTCAGAGCA ACCCCCAAAC TCACAATTGT ATATGGCCTT ACTCAATGCA ATGTGAATGC    1920

TGGAGGGTAG GTTCACGCCT TACTCATCTT TGCATCCGAA GCCCAGGGCA AATGTACTTA    1980

TTGAATGCAC TTCAACAACT GGGCCAAAGG CAGGGTCTCA AAGCTGGTGA AGCCAAAGTC    2040

AAAAGTCCAA AACATGGCTC AAGCTAGCAC CATGCTTGTG GGGCCCTCAA CTGGGTTTCC    2100

CAGTCTCATT CATTCCTCTT TTCCACATTG TTTTCAGTTT CCTATGATGA GCATGAGATG    2160

ATATACAAGT GGGAGAATTT CAAACTCAAA ATCGATGCGA AGAACACTTG GAAGCTATTG    2220

GAGTTTGATT TTACAGGAGT GAACAACAAA ACTGAAATCA TCTCCACCCC AGTTGGTAAG    2280

TGTGCAGTGG GAGCTAGAGC TGGGCAGAGT CTGAGGGTGT AGTACCAACA ACTGGAAGTG    2340

GCTATTTGTA CCAATGCTAT GTAAAGAGCT TATGGAAACA CTGTCTAGGA CATCGCTTCT    2400

CTCTCATATA TGCTAAACAC TTACAACTGT TTGCAGAGGA AACTGAGACT TCATAGCTAT    2460

GTCTCAGTCT CATCTGCAAA GAAGTAAGTG CTTTGCCAAG CCCCTTGAAG GACGGGGTAA    2520

GTAGATATAT GTTTGTAACC TTCAGTATGT TAATCTACCT TTTGAGTTTT AGATCTTTTG    2580

TATTTAATTT CTTTCTTATA TCACTGACTA ACTTAGACAA CATTGGGGAG GGGTACTCTG    2640

TGTGATTTTA CCAAATCCTG AACCAGGTCA AGTTGGTTGA GTGGGAAGGA AGACCACCCT    2700

AGCAGGAGGT AGAAGTGGAA ACTAGAGTGA CAATGGCGGC TAGTAGGGAT TGAGGAGTCT    2760

GCAGATGGTT ACTCAGGTGC AATGGCTACA GTAATATTAT CTTAAAGGAG CAACTGTGAA    2820

GAGTACATAT TTTCACCAGA GGCTTCAGAG TGGAATCAAC ATAAACATGT TTTTTCCTCC    2880

TGATCTTGTT CCTGACAAGG ATAATAGGGG CAGATTCTGG GTCTCTTAAC TTGTATCTCC    2940

CAAATAGATG TGAGCATCTT TGCTTGTATT CCTAGGTGAT CTGAATGAGG AGCCAATAAA    3000

TCTTCTCAGG GTACCTCTGA GAGCAACCCT GGACCTTCTT CACATGTACT GACAAGAATG    3060

TGGATGGATC AGGTCACCCA GCCAGACTTT TGACATTTAT TTTGCTTTGC TTCTGTGTGA    3120

TGATGACATA AAAAAATCTG CTATTGCTAC TGTTGGTCAC TCGGTGAGGG GCAGCTTATG    3180

CTAACCCAAC TAAAGCTTTG CTTATACAAT ACTAGGCAGG GATGGGTGCT GCTTGTCCTG    3240

TTCCTGGGAC TCTGAGAAAG CCTTCTTGCT TGCTTTGACT TGGGGTTCTT GTTCTTCTTC    3300

TACATAAATG TGGGCCTGCC TCTTAGTATT CAGTTTGTCC AGATAGGTGG AGCCTCATCA    3360

TCAGAAGTGA CAGAAGAGAC AAGGTTCAGG GGCTTTCAAG TCACTAGTGG TTCCGTTTAG    3420

TAGATGGTTT TTGCATTGTT TCAAAATGGT GCCCTAGTGA CTACAAAGCC CCAGAGCCAG    3480

CATCATCAGT GAAGCAATGT CAGTAGGTAA GCAACATCTC TTACTGTGGA GAAAGAAATA    3540

GGTCTTCTTT TTTCATTGAC TAGAGACTAC TTATTCTGAA TTCATACTGT CTTCACTGTC    3600
```

```
AGTTATTTTT GAGTCAGGTT CCAACTCTCC CAGTTTGACC CTGGGGCACT TCTTTCTAGC    3660

TAGAACACAC ATGTACTCAT TTTTCAGGGT TTAAATGCAG CAGTGCCCTG CAACTTGGGC    3720

CATCTTGGAC CTTACAGCAG AGTTTCTGCT TCAGGAGCTT CTCAGAAAGT GCAGCCTTGT    3780

CTGTAGTAAG TAAACCATCC TTCACTGGTG GCTGTTGAGC CTCTGAGGAA ATCTTGCCAC    3840

GATCAAGAGG TCAGCATCTT ACAAGGAGAT TATTTTCTTC CCTAGACGTC TCTTTCCATC    3900

AGAAAATTCT TCTTGCTCAT CTAAAATGGG AGTTTCTGGA ACATTTACCC ATCAGATCTA    3960

GTTCTTTTTC CCCTATAACT ACCCAGTTTA CATTAATTTA AGGTACTCTT TCAAAAGTCA    4020

AATGTAAAGA TCTAGGGTTA ACATTAGAGC ACACATTTGT ATTCTATTGG GACTCTCCTC    4080

CCTAGTTCCT TTTCTTCTCT TGTTCTTCAG TTCACTAGTC CTCTGGGCAG TCTTTTAATT    4140

GTGTCTTTTG ACAGTGCAGC CATCAACTAT GATCTGGACA AAGCAGGTAA GAACCAAAGT    4200

CATCTTTAAT CCATTTTGTT TTGGTTTGGC TTTCAGTCCT AGATACCTCT CTTCCATTGG    4260

TATTGCTTCT TCAATCATCA GAATGAAAGA AACACTTATT AGTATCCTTC TCTTGTCCAA    4320

TTTCCAGCTT TTAGTAAATA AAACATTTCT TCTTTAATCA GACTGACTAA AATTTAAAGA    4380

ATGAGAAACC CAACAGCACA ATGCATCTTG TGACATACAT ATTAAGGGAG TTTTTAATCA    4440

CAGTCAAGTC TCCAGGACAG AAAGAATAAT AATTTGGTCA TTCTGGCTAG TAGCATAGAA    4500

TGGTTTCTGG TGCAGTGCCG GAGGCATTCT AGTATTCAGG CAGGAAGTTT CCCACTGACC    4560

ATAAGCTACT TATTTGCCTT TCTCTGAAGA ACCTGAGAAG CTTTGTTCCT CCAAGGTCAA    4620

GTCTCCTAAC ACTAGGAGGA AAGGTTGCTC TCGATCTTCA CGGCCCACTC AGACTTGCCA    4680

GGTACATGGT CTGTTTTCTG TATAGTCTAC AGTCTAGACA TTTAGTGTTT ATGTCTGCCT    4740

TCCAAGGTTA TTTTGACCAG GGTATCAAA AGTCACTGAG CACCATTGTT TCCCATGTTA    4800

TGCCAGGCTT GGTTGGCTAG GGCTATGTT AAAGGCTTTA TATGAGCCCT TCCAGGCAGG    4860

AGCTTGAAGG TCCATTTAAT TTAAGGTCAC AGGTGGCTGT TGCATCACAG AACTGGAAAT    4920

TGAGGGCTTA ACTTCACAGA AAAATCCATG GTTGAGACAA TTTAATGTCT AATGACATGG    4980

AGAGTAAAAG TGATCCTCTG GCAAACTAA GCATGGAGTC ATAATATTAT GAAGAGCATT    5040

AGAAGCAACA TTAGGAACAG AATATGCCAG CTGGAAATAC AGGCTTGATC AACTTCTGAA    5100

AGATCCATTT CTATCTAAAG TAAATACATG AGAAGGTCAT TATACCCAAG TGAATGTGAA    5160

GGCCTACACT GCCTTCCGTC TGAATCTTTT GCAAACCTAA CATCTAAAGC TTGACTGACA    5220

AGTTCATATT CATCTACTTC TATTTTCCTA GGACATTGAA TTTAGGTTAA GCAGTAATAG    5280

ATCAAGAAGA GGGAGTCCAG GATTTGCTTA CCAGTATAAA TATATGTGGT ATCTAAACTG    5340

GGAAGCAGTT CAATTAGTTT TAGGTGAGGC ATTCATGTTG TATGTGTGCA TATGTATGAG    5400

TCAAATCCAG TTAGGTCTTA GAATCAGAAT ACATAGTGTA GACACTATTA TGTAGCTCAT    5460

ATATAGCAGA ATATGTCATA TTTGGCTAAC CCAAGTGGGC ATGCTATGAG GACTAACAGG    5520

GCAGATAATG TTGTGACATC ACAAACTATA CATTGCATTT CTGTGGGTCT CAGCTAGCCA    5580

TCAGCTATTA GGTTTTAATA CCATGAAAGT AAAGGTTATG GGGTTGTTTC TTGTTTGTTT    5640

GATTTGTTTT GAACTTTTCT CTCACTACTG CTTCTCTGGG AAAAACAGAT TTGGGAGAA    5700

TGAATCAGTT AACTGAAAGT AGGTTTATTA ATACTCTTGT ACCAGCTTAT CTCTCAATTA    5760

GCAATGGGTC TTACAGTAAA TATCTGAGTT CTACTTTGC TGCACTGAAA TACTGTGCCT    5820

TTATTATAGA ACTTTGAAAG GGTTTCCCAT GAGCTGGATG GTGGGAGCCA CACTATATGT    5880

GCCATGCTGG ACATCAGGCC AGTACTGCAA TGCAGTGGTG TATTTGATGT CTTTCAGGTG    5940

ACTTCATGGT CATGACATTC TTCTTCAATG TAAGCAGGAG GTTTGGCTTC ATTGTCTTTC    6000
```

```
AAAACTATAT CCCTTCATCT GTTACCACAA TGCTTTCCTG GGTGTCCTTC TGGATCAAGA      6060

TAGAAGCTGC TGCTGCCAGG GCCTCTGTAG GTAAGAAAGT ATGGTGATCT TAAATGTGAT      6120

CATATGTCAT AGATTAACAT TGCCTTCTCC TGTTGTCCTG CAGCACTGTC AGGAGCTTAG      6180

CCCACCTTCA CTCCTTGCTC TTATAGGGGT CAGTTCTGTG CTCACCATGG CCACACTGGG      6240

TACCTTTTCT CGTAAGAATT TCCCTCGTGT CTCCTATCTC ACAGCTTTGG ACTTCTATAT      6300

TGCAATTTGT TTCGTCTTGT GCTTCTGTAC TCTACTAGAG TTCACTGTGC TCAACTTCCT      6360

GACCTACAAT AATATTGAAC GACAGGCTTC TCCAAAGTTC TACCAAGTAA GAACCACGTG      6420

TTGGTATGGG AAGCAAAACT TTAGACTGAA GATAGGAGGG TTATGGCACT TGTGTGACTA      6480

CCTTTCCAAG TGATGAGAAT TTCCCTGGGG TTATAGAGGA AATAAACTTG CTGTGATATC      6540

CAGGAAGGCC TAGAACTGAT GTGGAGAGTG TAGTTTCTAG GAAATTCTAG GCAACTTTTC      6600

TTCTTGACTC ACTTTCCCTT GACCATTTTG TTATCTTTAT TTTTCTATTT CAGTTTCCAA      6660

CCAATAGCCG TGCTAATGCA CGTACTCGTG CTCGTGCCCG CACTCGTGCT CGTGCTCGTG      6720

CCCGTGCTCG TCAGCAGCAG GAAGTGTTTG TGTGTGAGAT TGTTACCTAT GAGGAAAATG      6780

CTGAAGAGGG TTACCAGTGG TCTCCAAGAT CAAGAAGACC TCAGTGTCCC TGGAGGCGAT      6840

GTGGCCGAAG CTATGTGTGC TTCAGGGTTC TCAGGAAGTA TTTCTGCATG GTTCCTGGTT      6900

GTGAGGGCAA CAGCTGGCAG CGGGGCCGCA TCTGCATCCA CGTTTATCGC CTGGATAACT      6960

ACTCGCGGGT GCTTTTCCCC ATTACATTCT TCTTCTTTAA TGTGGTCTAC TGGGTGATTT      7020

GCCTTAACCT GTAGGCTCCA GCTGGTAGCT CATGGGCAA TCACCTCAGT TCCCCAGGAG       7080

GTCCTAAGCC CCTTTGTCAA GGGAGTTGGG AGACAATAGC AACAGCAGCA AGCCTGAGGA      7140

GAGTTTGTCT TTGCTGCTCC TCCTTTTGTT GGCCCCTTCA CTCAATCTTT TAAACAGCAC      7200

TTCTCAAGTA ACAGCCCACC TCTCTATTCT TCAAAGAGTA TCCATGATGT TCAGTGTGCC      7260

CACAATTGAG CAGATAAGCT ATCTCTTGGT TGTGTTTGCA GTTACTGTTT TTCCCCAGGA      7320

GGTCATGGTA CCATTTGTGG TGCTAAGGGG CCCAGCTCAA GCTCAGCCCT AGAATGCACA      7380

GAGCAACAAC AGTATAGCAG AAGGAAGGTC CTCATCCTTA AGTCTTTAAG TCAGGCTATT      7440

TGATTTTTTC TCCCTGCTCT CTCTTCCTCT ACACACACA                             7479

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

CGCGACCTCC                                                                10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:
```

TCCAGTCGAG                                                                    10

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

GTGAGTCTCC                                                                    10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

AATGTTATAG                                                                    10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

GGTCGAGGGA                                                                    10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

GGCATTGGAG                                                                    10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

GTGAGGAGCA                                                                    10

(2) INFORMATION FOR SEQ ID NO:14:

```
      (i) SEQUENCE CHARACTERISTICS:
          (A) LENGTH: 10 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:14:

TCCCTTATAG                                                              10

(2) INFORMATION FOR SEQ ID NO:15:

(i) SEQUENCE CHARACTERISTICS:
          (A) LENGTH: 10 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:15:

AGAAGCCCAC                                                              10

(2) INFORMATION FOR SEQ ID NO:16:

(i) SEQUENCE CHARACTERISTICS:
          (A) LENGTH: 10 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:16:

CCTAGACATG                                                              10

(2) INFORMATION FOR SEQ ID NO:17:

(i) SEQUENCE CHARACTERISTICS:
          (A) LENGTH: 10 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:17:

GTGAGTACTA                                                              10

(2) INFORMATION FOR SEQ ID NO:18:

(i) SEQUENCE CHARACTERISTICS:
          (A) LENGTH: 10 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:18:

TTCCCACCAG                                                              10

(2) INFORMATION FOR SEQ ID NO:19:

(i) SEQUENCE CHARACTERISTICS:
          (A) LENGTH: 10 base pairs
          (B) TYPE: nucleic acid
```

```
        (C) STRANDEDNESS: double
        (D) TOPOLOGY: linear (ii) MOLECULE TYPE: cDNA (xi) SEQUENCE DESCRIPTION: SEQ ID NO:19:

GAATACACCA                                                              10

(2) INFORMATION FOR SEQ ID NO:20:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:20:

ACACAATTAG                                                              10

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:21:

GTATGTCAAG                                                              10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:22:

TCCCTTCCAG                                                              10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:23:

GATGACCATT                                                              10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA
```

-continued (xi) SEQUENCE DESCRIPTION: SEQ ID NO:24:

TTCTCTAGCT                                                                    10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:25:

GTGAGTACCT                                                                    10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:26:

TCCTTTCCAG                                                                    10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:27:

TTTCCTATCC                                                                    10

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:28:

ACCCCAGTTG                                                                    10

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:29:

GTAAGCGTGC                                                                    10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:30:

GTCTTTTCAG                                                          10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:31:

GTGACTTCAT                                                          10

(2) INFORMATION FOR SEQ ID NO:32:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:32:

ACCTCTCTAG                                                          10

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:33:

GTAAGAGGAG                                                          10

(2) INFORMATION FOR SEQ ID NO:34:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:34:

GCTCTTGCAG                                                          10

(2) INFORMATION FOR SEQ ID NO:35:

(i) SEQUENCE CHARACTERISTICS:
    (A) LENGTH: 10 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:35:

GGATCACCTC                                                          10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:36:

ACTCCGCCAT                                                          10

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:37:

GTATGAGCTG                                                          10

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:38:

TCCATTTTAG                                                          10

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:39:

CCTCGTATCA                                                          10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO:40:

ATATATCAGC                                                              10

(2) INFORMATION FOR SEQ ID NO:41:

(i) SEQUENCE CHARACTERISTICS:
        (A) LENGTH: 3154 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 41..1558

(ix) FEATURE:
        (A) NAME/KEY: sig_peptide
        (B) LOCATION: 41..94

(ix) FEATURE:
        (A) NAME/KEY: mat_peptide
        (B) LOCATION: 95..1558

(xi) SEQUENCE DESCRIPTION: SEQ ID NO:41:

```
CGCGACCTCC GCGCAGGTGG TCGCGCCGGT CTCCGCGGAA ATG TTG TCC AAA GTT          55
                                           Met Leu Ser Lys Val
                                           -18             -15

CTT CCA GTC CTC CTA GGC ATC TTA TTG ATC CTC CAG TCG AGG GTC GAG         103
Leu Pro Val Leu Leu Gly Ile Leu Leu Ile Leu Gln Ser Arg Val Glu
        -10                  -5                   1

GGA CCT CAG ACT GAA TCA AAG AAT GAA GCC TCT TCC CGT GAT GTT GTC         151
Gly Pro Gln Thr Glu Ser Lys Asn Glu Ala Ser Ser Arg Asp Val Val
     5                   10                  15

TAT GGC CCC CAG CCC CAG CCT CTG GAA AAT CAG CTC CTC TCT GAG GAA         199
Tyr Gly Pro Gln Pro Gln Pro Leu Glu Asn Gln Leu Leu Ser Glu Glu
 20                  25                  30                  35

ACA AAG TCA ACT GAG ACT GAG ACT GGG AGC AGA GTT GGC AAA CTG CCA         247
Thr Lys Ser Thr Glu Thr Glu Thr Gly Ser Arg Val Gly Lys Leu Pro
             40                  45                  50

GAA GCC TCT CGC ATC CTG AAC ACT ATC CTG AGT AAT TAT GAC CAC AAA         295
Glu Ala Ser Arg Ile Leu Asn Thr Ile Leu Ser Asn Tyr Asp His Lys
                 55                  60                  65

CTG CGC CCT GGC ATT GGA GAG AAG CCC ACT GTG GTC ACT GTT GAG ATC         343
Leu Arg Pro Gly Ile Gly Glu Lys Pro Thr Val Val Thr Val Glu Ile
         70                  75                  80

GCC GTC AAC AGC CTT GGT CCT CTC TCT ATC CTA GAC ATG GAA TAC ACC         391
Ala Val Asn Ser Leu Gly Pro Leu Ser Ile Leu Asp Met Glu Tyr Thr
             85                  90                  95

ATT GAC ATC ATC TTC TCC CAG ACC TGG TAC GAC GAA CGC CTC TGT TAC         439
Ile Asp Ile Ile Phe Ser Gln Thr Trp Tyr Asp Glu Arg Leu Cys Tyr
100                 105                 110                 115

AAC GAC ACC TTT GAG TCT CTT GTT CTG AAT GGC AAT GTG GTG AGC CAG         487
Asn Asp Thr Phe Glu Ser Leu Val Leu Asn Gly Asn Val Val Ser Gln
                 120                 125                 130

CTA TGG ATC CCG GAC ACC TTT TTT AGG AAT TCT AAG AGG ACC CAC GAG         535
Leu Trp Ile Pro Asp Thr Phe Phe Arg Asn Ser Lys Arg Thr His Glu
             135                 140                 145

CAT GAG ATC ACC ATG CCC AAC CAG ATG GTC CGC ATC TAC AAG GAT GGC         583
His Glu Ile Thr Met Pro Asn Gln Met Val Arg Ile Tyr Lys Asp Gly
```

```
                    150                 155                 160
AAG GTG TTG TAC ACA ATT AGG ATG ACC ATT GAT GCC GGA TGC TCA CTC         631
Lys Val Leu Tyr Thr Ile Arg Met Thr Ile Asp Ala Gly Cys Ser Leu
        165                 170                 175

CAC ATG CTC AGA TTT CCA ATG GAT TCT CAC TCT TGC CCT CTA TCT TTC         679
His Met Leu Arg Phe Pro Met Asp Ser His Ser Cys Pro Leu Ser Phe
180                 185                 190                 195

TCT AGC TTT TCC TAT CCT GAG AAT GAG ATG ATC TAC AAG TGG GAA AAT         727
Ser Ser Phe Ser Tyr Pro Glu Asn Glu Met Ile Tyr Lys Trp Glu Asn
                200                 205                 210

TTC AAG CTT GAA ATC AAT GAG AAG AAC TCC TGG AAG CTC TTC CAG TTT         775
Phe Lys Leu Glu Ile Asn Glu Lys Asn Ser Trp Lys Leu Phe Gln Phe
            215                 220                 225

GAT TTT ACA GGA GTG AGC AAC AAA ACT GAA ATA ATC ACA ACC CCA GTT         823
Asp Phe Thr Gly Val Ser Asn Lys Thr Glu Ile Ile Thr Thr Pro Val
        230                 235                 240

GGT GAC TTC ATG GTC ATG ACG ATT TTC TTC AAT GTG AGC AGG CGG TTT         871
Gly Asp Phe Met Val Met Thr Ile Phe Phe Asn Val Ser Arg Arg Phe
245                 250                 255

GGC TAT GTT GCC TTT CAA AAC TAT GTC CCT TCT TCC GTG ACC ACG ATG         919
Gly Tyr Val Ala Phe Gln Asn Tyr Val Pro Ser Ser Val Thr Thr Met
260                 265                 270                 275

CTC TCC TGG GTT TCC TTT TGG ATC AAG ACA GAG TCT GCT CCA GCC CGG         967
Leu Ser Trp Val Ser Phe Trp Ile Lys Thr Glu Ser Ala Pro Ala Arg
                280                 285                 290

ACC TCT CTA GGG ATC ACC TCT GTT CTG ACC ATG ACC ACG TTG GGC ACC        1015
Thr Ser Leu Gly Ile Thr Ser Val Leu Thr Met Thr Thr Leu Gly Thr
            295                 300                 305

TTT TCT CGT AAG AAT TTC CCG CGT GTC TCC TAT ATC ACA GCC TTG GAT        1063
Phe Ser Arg Lys Asn Phe Pro Arg Val Ser Tyr Ile Thr Ala Leu Asp
        310                 315                 320

TTC TAT ATC GCC ATC TGC TTC GTC TTC TGC TTC TGC GCT CTG TTG GAG        1111
Phe Tyr Ile Ala Ile Cys Phe Val Phe Cys Phe Cys Ala Leu Leu Glu
325                 330                 335

TTT GCT GTG CTC AAC TTC CTG ATC TAC AAC CAG ACA AAA GCC CAT GCT        1159
Phe Ala Val Leu Asn Phe Leu Ile Tyr Asn Gln Thr Lys Ala His Ala
340                 345                 350                 355

TCT CCT AAA CTC CGC CAT CCT CGT ATC AAT AGC CGT GCC CAT GCC CGT        1207
Ser Pro Lys Leu Arg His Pro Arg Ile Asn Ser Arg Ala His Ala Arg
                360                 365                 370

ACC CGT GCA CGT TCC CGA GCC TGT GCC CGC CAA CAT CAG GAA GCT TTT        1255
Thr Arg Ala Arg Ser Arg Ala Cys Ala Arg Gln His Gln Glu Ala Phe
            375                 380                 385

GTG TGC CAG ATT GTC ACC ACT GAG GGA AGT GAT GGA GAG GAG CGC CCG        1303
Val Cys Gln Ile Val Thr Thr Glu Gly Ser Asp Gly Glu Glu Arg Pro
        390                 395                 400

TCT TGC TCA GCC CAG CAG CCC CCT AGC CCA GGT AGC CCT GAG GGT CCC        1351
Ser Cys Ser Ala Gln Gln Pro Pro Ser Pro Gly Ser Pro Glu Gly Pro
405                 410                 415

CGC AGC CTC TGC TCC AAG CTG GCC TGC TGT GAG TGG TGC AAG CGT TTT        1399
Arg Ser Leu Cys Ser Lys Leu Ala Cys Cys Glu Trp Cys Lys Arg Phe
420                 425                 430                 435

AAG AAG TAC TTC TGC ATG GTC CCC GAT TGT GAG GGC AGT ACC TGG CAG        1447
Lys Lys Tyr Phe Cys Met Val Pro Asp Cys Glu Gly Ser Thr Trp Gln
                440                 445                 450

CAG GGC CGC CTC TGC ATC CAT GTC TAC CGC CTG GAT AAC TAC TCG AGA        1495
Gln Gly Arg Leu Cys Ile His Val Tyr Arg Leu Asp Asn Tyr Ser Arg
            455                 460                 465

GTT GTT TTC CCA GTG ACT TTC TTC TTC TTC AAT GTG CTC TAC TGG CTT        1543
```

-continued

```
Val Val Phe Pro Val Thr Phe Phe Phe Phe Asn Val Leu Tyr Trp Leu
        470               475               480

GTT TGC CTT AAC TTG TAG GTACCAGCTG GTACCCTGTG GGGCAACCTC           1591
Val Cys Leu Asn Leu  *
    485

TCCAGTTCCC CAGGAGGTCC AAGCCCCTTG CCAAGGGAGT TGGGGAAAAG CAGCAGCAGC  1651

AGCAGGAGCG ACTAGAGTTT TTCCTGCCCC ATTCCCCAAA CAGAAGCTTG CAGAGGGTTT  1711

GTCTTTGCTG CCCCTCTCCC CTACCTGGCC CATTCACTGA GTCTTCTCAG CAGACCATTT  1771

CAAATTATTA ATAAATGGGC CACCTCCCTC TTCTTCAAGG AGCATCCGTG ATGCTCAGTG  1831

TTCAAAACCA CAGCCACTTA GTGATCAGCT CCCTAAAACC ATGCCTAAGT ACAGGCGGAT  1891

TAGCTATCTT CCAACAATGC TGACCACCAG ACAATTACTG CATTTTTCCA GAAGCCCACT  1951

ATTGCCTTTG TAGTGCTTTC GGCCCAGTTC TGGCCTCAGC CTCAAAGTGC ACCGACTAGT  2011

TGCTTGCCTA TACCTGGCAC CTCATTAAGA TGCTGGGCAG CAGTATAACA GGAGGAAGAG  2071

ATCCCTCTCC TTTGGTCAGA TTATTATGTT CTCAGTTCTC TCTCCCTGCT ACCCCTTTCT  2131

CTGCAGATAG ATAGACACTG GCATTATCCC TTTAGGAAGA GGGGGGGGCA GCAAGAGAGC  2191

CTATTTGGGA CAGCATTCCT CTCTCTCTGC TGCTGTGACA TCTCCCTCTC CTTGCTGGCT  2251

CCATCTTTCG TCTGCACTAC CAATTCAATG CCCTTCATCC AATGGGTATC TATTTTTGTG  2311

TGTGATTATA GTAACTACTC CCTGCTTTAT ATGCCACCCT CTTCCTTCTC TTTGACCCCT  2371

GTGACTCTTT CTGTAACTTT CCCAGTGACT TCCCCTAGCC CTGACCCAGG CACTAGGCCT  2431

TGGTGACTTC CTGGGGCCAA GAAACTAAGG AAACTCGGCT TTGCAACAGG CATTACTCGC  2491

CATTGATTGG TGCCCACCCA GGGCACACTG TCGGAGTTCT ATCACTTGCT TGACCCCTGG  2551

ACCCATAAAC CAGTCCACTG TTATACCCGG GGCACTCTAA CCATCACAAT CAATCAATCA  2611

AATTCCCTTA AATTTGTATG GCACTGGAAC TTTGGCAAAG CACTTTTGAC AAGTTGTGTC  2671

TGATTGGAGC TTCATGATAG CCTTGTGACA TCTTTAGGGC AGGATTCTTA TCCCCATTTT  2731

GCAGATGAAA ACCCTGAGTC ACAGATTTCT GTGGGACTGT GGATCTCACT GGAAGCTATC  2791

CAAGAGCCCA CTGTCACCTT CTAGACCACA TGATAGGGCT AGACAGCTCA GTTCACCATG  2851

ATTCTCTTCT GTCACCTCTG CTGGCACACC AGTGGCAAGG CCCAGAATGG CGACCTCTCT  2911

TTAGCTCAAT TTCTGGGCCT GAGGTGCTCA GACTGCCCCC AAGATCAAAT CTCTCCTGGC  2971

TGTAGTAACC CAGTGGAATG AATTTGGACA TGCCCCAATG CTTCTATATG CTAAGTGAAA  3031

TCTGTGTCTG TAATTTGTTG GGGGGTGGAT AGGGTGGGGT CTCCATCTAC TTTTTGTCAC  3091

CATCATCTGA AATGGGGAAA TATGTAAATA AATATATCAG CAAAGCAAAA AGAAAAAAAA  3151

AAA                                                              3154

(2) INFORMATION FOR SEQ ID NO:42:

(i) SEQUENCE CHARACTERISTICS:
        (A) LENGTH: 506 amino acids
        (B) TYPE: amino acid
        (D) TOPOLOGY: linear (ii) MOLECULE TYPE: protein (xi) SEQUENCE DESCRIPTION: SEQ ID NO:42:

Met Leu Ser Lys Val Leu Pro Val Leu Leu Gly Ile Leu Leu Ile Leu
-18             -15                 -10                 -5

Gln Ser Arg Val Glu Gly Pro Gln Thr Glu Ser Lys Asn Glu Ala Ser
           1               5                  10
```

-continued

```
Ser Arg Asp Val Val Tyr Gly Pro Gln Pro Gln Pro Leu Glu Asn Gln
 15              20              25              30

Leu Leu Ser Glu Glu Thr Lys Ser Thr Glu Thr Glu Thr Gly Ser Arg
             35              40              45

Val Gly Lys Leu Pro Glu Ala Ser Arg Ile Leu Asn Thr Ile Leu Ser
             50              55              60

Asn Tyr Asp His Lys Leu Arg Pro Gly Ile Gly Glu Lys Pro Thr Val
             65              70              75

Val Thr Val Glu Ile Ala Val Asn Ser Leu Gly Pro Leu Ser Ile Leu
     80              85              90

Asp Met Glu Tyr Thr Ile Asp Ile Ile Phe Ser Gln Thr Trp Tyr Asp
 95             100             105             110

Glu Arg Leu Cys Tyr Asn Asp Thr Phe Glu Ser Leu Val Leu Asn Gly
            115             120             125

Asn Val Val Ser Gln Leu Trp Ile Pro Asp Thr Phe Phe Arg Asn Ser
            130             135             140

Lys Arg Thr His Glu His Glu Ile Thr Met Pro Asn Gln Met Val Arg
            145             150             155

Ile Tyr Lys Asp Gly Lys Val Leu Tyr Thr Ile Arg Met Thr Ile Asp
    160             165             170

Ala Gly Cys Ser Leu His Met Leu Arg Phe Pro Met Asp Ser His Ser
175             180             185             190

Cys Pro Leu Ser Phe Ser Ser Phe Ser Tyr Pro Glu Asn Glu Met Ile
            195             200             205

Tyr Lys Trp Glu Asn Phe Lys Leu Glu Ile Asn Glu Lys Asn Ser Trp
            210             215             220

Lys Leu Phe Gln Phe Asp Phe Thr Gly Val Ser Asn Lys Thr Glu Ile
            225             230             235

Ile Thr Thr Pro Val Gly Asp Phe Met Val Met Thr Ile Phe Phe Asn
    240             245             250

Val Ser Arg Arg Phe Gly Tyr Val Ala Phe Gln Asn Tyr Val Pro Ser
255             260             265             270

Ser Val Thr Thr Met Leu Ser Trp Val Ser Phe Trp Ile Lys Thr Glu
            275             280             285

Ser Ala Pro Ala Arg Thr Ser Leu Gly Ile Thr Ser Val Leu Thr Met
            290             295             300

Thr Thr Leu Gly Thr Phe Ser Arg Lys Asn Phe Pro Arg Val Ser Tyr
            305             310             315

Ile Thr Ala Leu Asp Phe Tyr Ile Ala Ile Cys Phe Val Phe Cys Phe
    320             325             330

Cys Ala Leu Leu Glu Phe Ala Val Leu Asn Phe Leu Ile Tyr Asn Gln
335             340             345             350

Thr Lys Ala His Ala Ser Pro Lys Leu Arg His Pro Arg Ile Asn Ser
            355             360             365

Arg Ala His Ala Arg Thr Arg Ala Arg Ser Arg Ala Cys Ala Arg Gln
            370             375             380

His Gln Glu Ala Phe Val Cys Gln Ile Val Thr Thr Glu Gly Ser Asp
            385             390             395

Gly Glu Glu Arg Pro Ser Cys Ser Ala Gln Gln Pro Ser Pro Gly
            400             405             410

Ser Pro Glu Gly Pro Arg Ser Leu Cys Ser Lys Leu Ala Cys Glu
415             420             425             430

Trp Cys Lys Arg Phe Lys Lys Tyr Phe Cys Met Val Pro Asp Cys Glu
```

```
                    435              440               445
Gly Ser Thr Trp Gln Gln Gly Arg Leu Cys Ile His Val Tyr Arg Leu
            450              455               460

Asp Asn Tyr Ser Arg Val Val Phe Pro Val Thr Phe Phe Phe Phe Asn
            465              470               475

Val Leu Tyr Trp Leu Val Cys Leu Asn Leu
            480              485
```

(2) INFORMATION FOR SEQ ID NO:43:

(i) SEQUENCE CHARACTERISTICS:
        (A) LENGTH: 303 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:43:

```
TAGGTACCAG CTGGTACCCT GTGGGGCAAC CTCTCCAGTT CCCCAGGAGG TCCAAGCCCC     60
TTGCCAAGGG AGTTGGGGGA AAGCAGCAGC AGCAGCAGGA GCGACTAGAG TTTTTCCTGC    120
CCCATTCCCC AAACAGAAGC TTGCAGAGGG TTTGTTTTTG CTGCCCCTCT CCCCTACCTG    180
GCCCATTCAC TGAGTCTTCT CAGCAGACCA TTTCAAATTA TTAATAAATG GGCCACCTCC    240
CTCTTCTTCA AGGAGCATCC GTGATGCTCA GTGTTCAAAA CCACAGCCAC TTAGTGATCA    300
GCT                                                                  303
```

(2) INFORMATION FOR SEQ ID NO:44:

(i) SEQUENCE CHARACTERISTICS:
        (A) LENGTH: 206 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:44:

```
GCTTTGCTGA TATATTTATT TACATATTTC CCCATTTCAG ATGATGGTGA CAAAAAGTAG     60
ATGGAGACCC CACCCTATCC ACCCCCCAAC AAATTACAGA CACAGATTTC ACTTAGCATA    120
TAGAAGCATT GGGGCATGTC CAAATTCATT CCACTGGGTT ACTACAGCCA GGAGAGATTT    180
GATCTTGGGG GCAGTCTGGA GCACCT                                         206
```

(2) INFORMATION FOR SEQ ID NO:45:

(i) SEQUENCE CHARACTERISTICS:
        (A) LENGTH: 3974 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:45:

```
GGTACCTAAG TGAGTAGGGC GTCCGATCGA CGGACGCCTT TTTTTTGAAT TCGTAATCAT     60
GGTCATAGCT GTTTCCTGTG TGAAATTGTT ATCCGCTCAC AATTCCACAC AACATACGAG    120
CCGGAAGCAT AAAGTGTAAA GCCTGGGGTG CCTAATGAGT GAGCTAACTC ACATTAATTG    180
CGTTGCGCTC ACTGCCCGCT TTCCAGTCGG GAAACCTGTC GTGCCAGCTG CATTAATGAA    240
TCGGCCAACG CGCGGGGAGA GGCGGTTTGC GTATTGGGCG CTCTTCCGCT TCCTCGCTCA    300
```

-continued

```
CTGACTCGCT GCGCTCGGTC GTTCGGCTGC GGCGAGCGGT ATCAGCTCAC TCAAAGGCGG      360

TAATACGGTT ATCCACAGAA TCAGGGGATA ACGCAGGAAA GAACATGTGA GCAAAAGGCC      420

AGCAAAAGGC CAGGAACCGT AAAAAGGCCG CGTTGCTGGC GTTTTTCCAT AGGCTCCGCC      480

CCCCTGACGA GCATCACAAA AATCGACGCT CAAGTCAGAG GTGGCGAAAC CCGACAGGAC      540

TATAAAGATA CCAGGCGTTT CCCCCTGGAA GCTCCCTCGT GCGCTCTCCT GTTCCGACCC      600

TGCCGCTTAC CGGATACCTG TCCGCCTTTC TCCCTTCGGG AAGCGTGGCG CTTTCTCATA      660

GCTCACGCTG TAGGTATCTC AGTTCGGTGT AGGTCGTTCG CTCCAAGCTG GGCTGTGTGC      720

ACGAACCCCC CGTTCAGCCC GACCGCTGCG CCTTATCCGG TAACTATCGT CTTGAGTCCA      780

ACCCGGTAAG ACACGACTTA TCGCCACTGG CAGCAGCCAC TGGTAACAGG ATTAGCAGAG      840

CGAGGTATGT AGGCGGTGCT ACAGAGTTCT TGAAGTGGTG GCCTAACTAC GGCTACACTA      900

GAAGAACAGT ATTTGGTATC TGCGCTCTGC TGAAGCCAGT TACCTTCGGA AAAAGAGTTG      960

GTAGCTCTTG ATCCGGCAAA CAAACCACCG CTGGTAGCGG TGGTTTTTTT GTTTGCAAGC     1020

AGCAGATTAC GCGCAGAAAA AAAGGATCTC AAGAAGATCC TTTGATCTTT TCTACGGGGT     1080

CTGACGCTCA GTGGAACGAA AACTCACGTT AAGGGATTTT GGTCATGAGA TTATCGTCGA     1140

CAATTCGCGC GCGAAGGCGA AGCGGCATGC ATTTACGTTG ACACCATCGA ATGGTGCAAA     1200

ACCTTTCGCG GTATGGCATG ATAGCGCCCG GAAGAGAGTC AATTCAGGGT GGTGAATGTG     1260

AAACCAGTAA CGTTATACGA TGTCGCAGAG TATGCCGGTG TCTCTTATCA GACCGTTTCC     1320

CGCGTGGTGA ACCAGGCCAG CCACGTTTCT GCGAAAACGC GGGAAAAAGT GGAAGCGGCG     1380

ATGGCGGAGC TGAATTACAT TCCCAACCGC GTGGCACAAC AACTGGCGGG CAAACAGTCG     1440

TTGCTGATTG GCGTTGCCAC CTCCAGTCTG GCCCTGCACG CGCCGTCGCA AATTGTCGCG     1500

GCGATTAAAT CTCGCGCCGA TCAACTGGGT GCCAGCGTGG TGGTGTCGAT GGTAGAACGA     1560

AGCGGCGTCG AAGCCTGTAA AGCGGCGGTG CACAATCTTC TCGCGCAACG CGTCAGTGGG     1620

CTGATCATTA ACTATCCGCT GGATGACCAG GATGCCATTG CTGTGGAAGC TGCCTGCACT     1680

AATGTTCCGG CGTTATTTCT TGATGTCTCT GACCAGACAC CCATCAACAG TATTATTTTC     1740

TCCCATGAAG ACGGTACGCG ACTGGGCGTG GAGCATCTGG TCGCATTGGG TCACCAGCAA     1800

ATCGCGCTGT TAGCGGGCCC ATTAAGTTCT GTCTCGGCGC GTCTGCGTCT GGCTGGCTGG     1860

CATAAATATC TCACTCGCAA TCAAATTCAG CCGATAGCGG AACGGGAAGG CGACTGGAGT     1920

GCCATGTCCG GTTTTCAACA AACCATGCAA ATGCTGAATG AGGGCATCGT TCCCACTGCG     1980

ATGCTGGTTG CCAACGATCA GATGGCGCTG GGCGCAATGC GCGCCATTAC CGAGTCCGGG     2040

CTGCGCGTTG GTGCGGATAT CTCGGTAGTG GGATACGACG ATACCGAAGA CAGCTCATGT     2100

TATATCCCGC CGTTAACCAC CATCAAACAG GATTTTCGCC TGCTGGGGCA AACCAGCGTG     2160

GACCGCTTGC TGCAACTCTC TCAGGGCCAG GCGGTGAAGG CAATCAGCT GTTGCCCGTC      2220

TCACTGGTGA AAAGAAAAAC CACCCTGGCG CCCAATACGC AAACCGCCTC TCCCCGCGCG     2280

TTGGCCGATT CATTAATGCA GCTGGCACGA CAGGTTTCCC GACTGGAAAG CGGGCAGTGA     2340

GCGCAACGCA ATTAATGTAA GTTAGCGCGA ATTGTCGACC AAAGCGGCCA TCGTGCCTCC     2400

CCACTCCTGC AGTTCGGGGG CATGGATGCG CGGATAGCCG CTGCTGGTTT CCTGGATGCC     2460

GACGGATTTG CACTGCCGGT AGAACTCCGC GAGGTCGTCC AGCCTCAGGC AGCAGCTGAA     2520

CCAACTCGCG AGGGGATCGA GCCCGGGGTG GGCGAAGAAC TCCAGCATGA GATCCCCGCG     2580

CTGGAGGATC ATCCAGCCGG CGTCCCGGAA AACGATTCCG AAGCCCAACC TTTCATAGAA     2640
```

-continued

```
GGCGGCGGTG GAATCGAAAT CTCGTGATGG CAGGTTGGGC GTCGCTTGGT CGGTCATTTC    2700

GAACCCCAGA GTCCCGCTCA GAAGAACTCG TCAAGAAGGC GATAGAAGGC GATGCGCTGC    2760

GAATCGGGAG CGGCGATACC GTAAAGCACG AGGAAGCGGT CAGCCCATTC GCCGCCAAGC    2820

TCTTCAGCAA TATCACGGGT AGCCAACGCT ATGTCCTGAT AGCGGTCCGC CACACCCAGC    2880

CGGCCACAGT CGATGAATCC AGAAAAGCGG CCATTTTCCA CCATGATATT CGGCAAGCAG    2940

GCATCGCCAT GGGTCACGAC GAGATCCTCG CCGTCGGGCA TGCGCGCCTT GAGCCTGGCG    3000

AACAGTTCGG CTGGCGCGAG CCCCTGATGC TCTTCGTCCA GATCATCCTG ATCGACAAGA    3060

CCGGCTTCCA TCCGAGTACG TGCTCGCTCG ATGCGATGTT TCGCTTGGTG GTCGAATGGG    3120

CAGGTAGCCG GATCAAGCGT ATGCAGCCGC CGCATTGCAT CAGCCATGAT GGATACTTTC    3180

TCGGCAGGAG CAAGGTGAGA TGACAGGAGA TCCTGCCCCG GCACTTCGCC CAATAGCAGC    3240

CAGTCCCTTC CCGCTTCAGT GACAACGTCG AGCACAGCTG CGCAAGGAAC GCCCGTCGTG    3300

GCCAGCCACG ATAGCCGCGC TGCCTCGTCC TGCAGTTCAT TCAGGGCACC GGACAGGTCG    3360

GTCTTGACAA AAAGAACCGG GCGCCCCTGC GCTGACAGCC GGAACACGGC GGCATCAGAG    3420

CAGCCGATTG TCTGTTGTGC CCAGTCATAG CCGAATAGCC TCTCCACCCA AGCGGCCGGA    3480

GAACCTGCGT GCAATCCATC TTGTTCAATC ATGCGAAACG ATCCTCATCC TGTCTCTTGA    3540

TCAGATCTTG ATCCCCTGCG CCATCAGATC CTTGGCGGCA AGAAAGCCAT CCAGTTTACT    3600

TTGCAGGGCT TCCCAACCTT ACCAGAGGGC GCCCCAGCTG GCAATTCCGG TTCGCTTGCT    3660

GTCCATAAAA CCGCCCAGTC TAGCTATCGC CATGTAAGCC CACTGCAAGC TACCTGCTTT    3720

CTCTTTGCGC TTGCGTTTTC CCTTGTCCAG ATAGCCCAGT AGCTGACATT CATCCGGGGT    3780

CAGCACCGTT TCTGCGGACT GGCTTTCTAC GTGTTCCGCT TCCTTTAGCA GCCCTTGCGC    3840

CCTGAGTGCT TGCGGCAGCG TGAAGCTTAA AAAACTGCAA AAAATAGTTT GACTTGTGAG    3900

CGGATAACAA TTAAGATGTA CCCAATTGTG AGCGGATAAC AATTTCACAC ATTAAAGAGG    3960

AGAAATTACA TATG                                                      3974
```

(2) INFORMATION FOR SEQ ID NO:46:

(i) SEQUENCE CHARACTERISTICS:
        (A) LENGTH: 112 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:46:

```
AAGCTTAAAA AACTGCAAAA AATAGTTTGA CTTGTGAGCG GATAACAATT AAGATGTACC      60

CAATTGTGAG CGGATAACAA TTTCACACAT TAAAGAGGAG AAATTACATA TG             112
```